United States Patent
Sharma et al.

(10) Patent No.: US 8,828,999 B2
(45) Date of Patent: *Sep. 9, 2014

(54) PYRIMIDINE COMPOUNDS AND THEIR USES

(71) Applicant: Orchid Chemicals and Pharmaceuticals Limited, Chennai (IN)

(72) Inventors: Ganapavarapu Sharma, Vishakhapatnam (IN); Venkatesan Parameswaran, Chennai (IN); Gopalan Balasubramanian, Chennai (IN); Santosh Vishwakarma, Chennai (IN); Sanjeev Saxena, Chennai (IN)

(73) Assignee: Orchid Chemicals & Pharmaceuticals Limited, Chennai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/777,813

(22) Filed: Feb. 26, 2013

(65) Prior Publication Data

US 2013/0172350 A1 Jul. 4, 2013

Related U.S. Application Data

(62) Division of application No. 12/863,796, filed as application No. PCT/IB2009/000157 on Jan. 30, 2009, now Pat. No. 8,420,653.

(30) Foreign Application Priority Data

Feb. 1, 2008 (IN) .............................. 271/CHE/2008

(51) Int. Cl.
| | |
|---|---|
| *A61K 31/535* | (2006.01) |
| *C07D 401/04* | (2006.01) |
| *C07D 239/42* | (2006.01) |
| *C07D 265/28* | (2006.01) |
| *A61K 31/5377* | (2006.01) |

(52) U.S. Cl.
CPC ............ *C07D 239/42* (2013.01); *C07D 401/04* (2013.01); *C07D 265/28* (2013.01); *A61K 31/5377* (2013.01)
USPC ........................................ 514/235.8; 544/122

(58) Field of Classification Search
CPC .......................... C07D 265/28; A61K 31/5377
USPC ................ 544/122, 328, 326; 514/235.8, 256
See application file for complete search history.

(56) References Cited

U.S. PATENT DOCUMENTS

| | | | |
|---|---|---|---|
| 4,698,340 A | 10/1987 | Takaya et al. | |
| 5,166,137 A | 11/1992 | Otterlei et al. | |
| 5,527,546 A | 6/1996 | Penza et al. | |
| 5,580,985 A | 12/1996 | Lee et al. | |
| 5,622,977 A | 4/1997 | Warrellow et al. | |
| 5,712,298 A | 1/1998 | Amschler | |
| 5,728,704 A | 3/1998 | Mylari et al. | |
| 6,004,813 A | 12/1999 | Serlupi-Crescenzi et al. | |
| 6,410,563 B1 | 6/2002 | Deschenes et al. | |
| 6,410,729 B1 | 6/2002 | Spohr et al. | |
| 6,420,385 B1 | 7/2002 | Spohr et al. | |
| 7,317,014 B2 | 1/2008 | Agarwal et al. | |
| 7,399,760 B2 | 7/2008 | Agarwal et al. | |
| 7,863,446 B2 * | 1/2011 | Srinivas et al. | ............... 544/319 |
| 2003/0232813 A1 | 12/2003 | Agarwal et al. | |
| 2004/0009975 A1 | 1/2004 | Agarwal et al. | |
| 2004/0254178 A1* | 12/2004 | Dominguez et al. | ........ 514/227.5 |
| 2005/0107413 A1 | 5/2005 | Agarwal et al. | |
| 2006/0194799 A1 | 8/2006 | Agarwal et al. | |
| 2007/0167413 A1* | 7/2007 | Srinivas et al. | ............... 514/151 |
| 2008/0207606 A1 | 8/2008 | Srinivas et al. | |

FOREIGN PATENT DOCUMENTS

| | | |
|---|---|---|
| WO | WO 96/03385 A1 | 2/1996 |
| WO | WO 99/50262 | 10/1999 |
| WO | WO 02/074298 A1 | 9/2002 |

(Continued)

OTHER PUBLICATIONS

J.H. Poupaert, Drug Design: Basic Principles and Applications, in 2 Encyclopedia of Pharmaceutical Technology 1362-1369, 1367 (James Swarbrick ed., 3rd ed., 2007).*

(Continued)

*Primary Examiner* — James O Wilson
*Assistant Examiner* — Alexander R Pagano
(74) *Attorney, Agent, or Firm* — Oliff PLC

(57) ABSTRACT

Pyrimidine compounds of the general formula (I), their derivatives, analogs, tautomeric forms, stereoisomers, polymorphs, hydrates, solvates, pharmaceutically acceptable salts, pharmaceutical compositions, metabolites and prodrugs thereof, are useful are useful as PDE4 inhibitors and are useful for treating PDE4 mediated diseases and in the treatment of immunological diseases, inflammation, pain disorder, rheumatoid arthritis; osteoporosis; multiple myeloma; uveititis; acute and chronic myelogenous leukemia; atherosclerosis; cancer; cachexia; ischemic-induced cell damage; pancreatic beta cell destruction; osteoarthritis; rheumatoid spondylitis; gouty arthritis; inflammatory bowel disease; ARDS; psoriasis; Crohn's disease; allergic rhinitis; ulcerative colitis; anaphylaxis; contact dermatitis; muscle degeneration; asthma; COPD; bone resorption diseases; multiple sclerosis; sepsis; septic shock; toxic shock syndrome and fever.

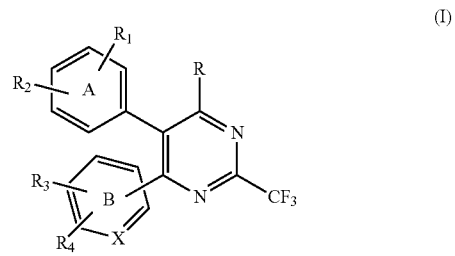

19 Claims, No Drawings

(56) References Cited

FOREIGN PATENT DOCUMENTS

| WO | WO 03/084935 A2 | 10/2003 |
|---|---|---|
| WO | WO 03/084935 A3 | 10/2003 |
| WO | WO 03/084938 A2 | 10/2003 |
| WO | WO 2004/009560 A1 | 1/2004 |
| WO | WO 2007/083182 A2 | 7/2007 |

OTHER PUBLICATIONS

B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
D. Spina 155 British Journal of Pharmacology, 308-315 (2008).*
C. Burnouf et al., 8 Current Pharmaceutical Design 1555-1296 (2002).*
Moser et al., "Interleukin 1 and Tumor Necrosis Factor Stimulate Human Vascular Endothelial Cells to Promote Transendothelial Neutrophil Passage," *The American Society for Clinical Investigation, Inc.*, vol. 83, Feb. 1989, pp. 444-455.
Haworth et al., "Expression of granulocyte-macrophage colony-stimulating factor in rheumatoid arthritis: regulation by tumor necrosis factor-α*," *Eur. J. Immunol.*, vol. 21, 1991, pp. 2575-2579.
Brennan et al., "Inhibitory Effect of the TNFα Antibodies on Synovial Cell Interleukin-1 Production in Rheumatoid Arthritis," *The Lancet*, vol. 2, Jul. 29, 1989, pp. 244-247.
Arend et al., "Inhibition of the Production and Effects of Interleukin-1 and Tumor Necrosis Factor α in Rheumatoid Arthritis," *Arthritis & Rheumatism*, vol. 38, No. 2, Feb. 1995, pp. 151-160.
Goldenberg, "Etanercept, a Novel Drug for the Treatment of Patients with Severe, Active Rheumatoid Arthritis," *Clinical Therapeutics*, vol. 21, No. 1, 1999, pp. 75-87.
Luong et al., "Treatment Options for Rheumatoid Arthritis: Celecoxib, Leflunomide, Etanercept, and Infliximab," *The Annals of Pharmacotherapy*, vol. 34, Jun. 2000, pp. 743-760.
Klein et al., "Murine Anti-Interleukin-6 Monoclonal Antibody Therapy for a Patient With Plasma Cell Leukemia," *Blood*, vol. 78, No. 5, Sep. 1, 1991, pp. 1198-1204.
Lu et al., "High amounts of circulating interleukin (IL)-6 in the form of monomeric immune complexes during anti-IL-6 therapy. Towards a new methodology for measuring overall cytokine production in human in vivo," *Eur. J. Immunol.*, vol. 22, Apr. 18, 1992, pp. 2819-2824.
Chandrasekhar et al., "Arthritis Induced by Interleukin-1 is Dependent on the Site and Frequency of Intraarticular Injection," *Clinical Immunology and Immunopathology*, vol. 55, 1990, pp. 382-400, Academic Press Inc.
Firestein et al., "Stromelysin and tissue inhibitor of metalloproteinases gene expression in rheumatoid arthritis Synovium," *American Journal of Pathology*, vol. 140, No. 6, Jun. 1992, pp. 1309-1314.
Dinarello, "The biological properties of interleukin-1," *Eur. Cytokine Netw.*, vol. 5; No. 6, Nov.-Dec. 1994, pp. 517-531.
Brahn et al., "Effects of Tumor Necrosis Factor Alpha (TNF-α) on Collagen Arthritis," *Lymphokine and Cytokine Research*, vol. 11, No. 5, Nov. 5, 1992, pp. 253-256.
Cooper et al, "Acceleration of onset of collagen-induced arthritis by intra-articular injection of tumour necrosis factor or transforming growth factor-beta," *Clinical and Experimental Immunology*, vol. 89, No. 2, Aug. 1992, pp. 244-250.
Kakazu et al., "Type 1 T-Helper Cell Predominance in Granulomas of Crohn's Disease," *The American Journal of Gastroenterology*, vol. 94, No. 8, 1999, pp. 2149-2155.
Colpaert et al., "In vitro analysis of IGN-gamma and IL-12 production and their effects in ileal Crohn's disease," *European Cytokine Network*, vol. 13, No. 4, Dec. 2002, pp. 431-437.
Berrebi et al., "Interleukin-12 Expression is Focally Enhanced in the Gastric Mucosa of Pediatric Patients with Crohn's Disease," *American Journal of Pathology*, vol. 152, No. 3, Mar. 1998, pp. 667-672.

Parronchi et al., "Type 1 T-Helper Cell Predominance and Interleukin-12 Expression in the Gut of Patients with Crohn's Disease," *American Journal of Pathology*, vol. 150, No. 3, Mar. 1997, pp. 823-832.
Monteleone et al., "Interleukin 12 is expressed and actively released by Crohn's disease intestinal lamina propria mononuclear cells," *Gastroenterology*, vol. 112, Issue 4, Apr. 1997, pp. 1169-1178.
Nielsen et al., "Upregulation of Interleukin-12 and -17 in Active Inflammatory Bowel Disease;" *Scand J Gastroenterol*, 2003, pp. 180-185.
Patrignani et al., "Biochemical and Pharmacological Characterization of the Cyclooxgygenase Activity of Human Blood Prostaglandin Endoperoxide Synthases," *Journal of Pharmacology and Experimental Therapeutics*, vol. 271, No. 3, 1994, pp. 1705-1712, The American Society for Pharmacology and Experimental Therapeutics.
Warner et al., "Nonsteroid drug selectivities for cyclo-oxygenase-1 rather than cyclo-oxygenase-2 are associated with human gastrointestinal toxicity: A full in vitro analysis," *Proceedings of the National Academy of Sciences of the United States of America*, vol. 96, Jun. 1999, pp. 7563-7568.
Xie et al., 1991, "Expression of a Mitogen-Responsive Gene Encoding Prostaglandin Synthase is Regulated by mRNA splicing," *Proceedings of the National Academy of Sciences of the United States of America*, vol. 88, 1991, pp. 2692-2696.
Maxey et al., "Interference in Enzyme Immunoassays," *Journal of Clinical Immunoassay*, vol. 15, No. 2, Summer 1992, pp. 116-120.
Jansky et al., "Dynamics of Cytokine Production in Human Peripheral Blood Mononuclear Cells Stimulated by LPS or Infected by Borrelia," *Physiological Research*, vol. 52, 2003, pp. 593-598.
Dauksas et al., "Synthesis and Anti-inflammatory Properties of Benzoyl, Halogenbenzoyl or Cinnamoyl Substituted1-Benzoxepanes and 2-methyl-benzoxolanes," *Arzneim-Forsch/Drug Res.*, vol. 43, No. 1, 1993, pp. 44-50.
Romano et al., "Transforming Growth Factor α Protection against Drug-induced Injury to the Rat Gastric Mucosa in Vivo," *The Journal of Clinical Investigation, Inc.*, vol. 90, Dec. 1992, pp. 2409-2421.
Theisen-Popp et al., "Antirheumatic drug profiles evaluated in the adjuvant arthritis of rats by multiparameter analysis," *Agent Actions*, vol. 42, 1994, pp. 50-55.
Fletcher et al., "Therapeutic Administration of a Selective Inhibitor of Nitric Oxide Synthase Does Not Ameliorate the Chronic Inflammation and Tissue Damage Associated with Adjuvant-Induced Arthritis in Rats," *The Journal of Pharmacology and Experimental Therapeutics*, vol. 284, No. 2, 1998, pp. 714-721.
Sekut et al., "Evaluation of the significance of elevated levels of systematic and localized tumor necrosis factor in different animal models of inflammation," *J Lab Clin Med*, vol. 124, No. 6, Dec. 1994, pp. 813-820.
Taylor et al., "Tumour Necrosis Factor α as a Therapeutic Target for Immune-Mediated Inflammatory Diseases", *Current Opinion in Biotechnology*, vol. 15, 2004, pp. 557-563, Elsevier Ltd.
Sommer et al., "Mechanisms of Neuropathic Pain: The Role of Cytokines", *Drug Discovery Today: Disease Mechanisms*, vol. 1, No. 4, 2004, pp. 441-448, Elsevier Ltd.
Link et al., "Phosphodiesterase 4 Inhibition But Not Beta-adrenergic Stimulation Suppresses Tumor Necrosis Factor-alpha Release in Peripheral Blood Mononuclear Cells in Septic Shock", *Critical Care*, vol. 12, No. 6, 2008, pp. 1-9.
Sturton et al., "Phosphodiesterase 4 Inhibitors for the Treatment of COPD", *Chest*, vol. 121, No. 5, May 2002, pp. 192S-196S.
Bielekova et al., "Therapeutic Potential of Phosphodiesterase-4 and -3 Inhibitors in Th1-Mediated Autoimmune Diseases", *The Journal of Immunology*, 2000, pp. 1117-1124.
Burger's Medicinal Chemistry, edited by Wolff, 5th Edition, vol. 1, 1995, pp. 975-977, John Wiley and Sons, Inc.
Modern Pharmaceutics, edited by Banker et al., 3rd Edition., 1996, pp. 451 and 596, Marcel Dekker, Inc.
Solid State Chemistry and its Applications, edited by West, 1988, pp. 358 & 365, John Wiley & Sons.
Vippagunta et al., "Crystalline solids," *Advanced Drug Delivery Reviews*, vol. 48, 2001, pp. 3-26, Elsevier Science B.V.

(56) References Cited

OTHER PUBLICATIONS

Textbook of Medicine edited by Bennett et al., vol. 1, pp. 1004-1010, W.B. Saunders Company.
Wang et al., "Structures of the four subfamilies of phosphodiesterase-4 provide insight into the selectivity of their inhibitors," *Biochemistry Journal*, vol. 408, 2007, pp. 193-201, Biochemical Society.
Boswell-Smith et al., "Phosphodiesterase inhibitors," *British Journal of Pharmacology*, vol. 147, 2007, pp. S252-S257.
Tracey et al., "Tumor necrosis factor antagonist mechanisms of action: A comprehensive review," *Pharmacology & Therapeutics*, vol. 117, 2008, pp. 244-279, Elsevier Inc.
Cortijo et al., "Investigation into the role of phosphodiesterase IV in bronchorelaxation, including studies with human bronchus," *Br. J. Pharmacol.*, vol. 108, 1993, pp. 562-568, Macmillan Press Ltd.
Otuki et al., "Topical antiinflammatory effects of the ether extract from *Protium kleinii* and α-amyrin pentacyclic triterpene," *European Journal of Pharmacology*, vol. 507, 2005, pp. 253-259, Elsevier Ltd.
Spond et al., "The role of neutrophils in LPS-induced changes in pulmonary function in conscious rats," *Pulmonary Pharmacology & Therapuetics*, vol. 17, 2004, pp. 133-140, Elsevier Ltd.
Office Action mailed on Oct. 2, 2008 in U.S. Appl. No. 12/068,668.
Office Action mailed on Jun. 12, 2009 in U.S. Appl. No. 12/068,668.
International Search Report dated Mar. 3, 2010 in International Patent Application No. PCT/IB2009/000157.
Written Opinion of the International Searching Authority dated Mar. 3, 2010 in International Patent Application No. PCT/IB2009/000157.
Nov. 20, 2009 Advisory Action issued in U.S. Appl. No. 12/068,668.
Tisdale; (1997) "Biology of Cachexia"; Journal of the National Cancer Institute; vol. (89); No. 23; pp. 1763-1773.
Winter, et al.; (1962); "Carrageenin-induced edema in hind paw of rat as an assay for antiinflammatory drugs"; Proceedings of the Society for Experimental Biology and Medicine; vol. (3); No. 3; pp. 544-547.
Oct. 7, 2008 Office Action issued in U.S. Appl. No. 11/633,053.
International Preliminary Report on Patentability dated Aug. 12, 2010 in International Patent Application No. PCT/IB2009/000157.
Notice of Allowance issued Oct. 22, 2010 in U.S. Appl. No. 12/068,668.
Chung, 533 European Journal of Pharmacology, 110-117, 111 (2006).
Traynor et al., Drugs Today, 40(80), 697-710, 698 (2004).
De Arruda et al., Int. J. Radiation Oncology Biol. Phys., 64(2), 363-373 (2006).
Rustgi, Molecular Biology of the Esophagus and Stomach, in 1 Cancer Principles & Practice of Oncology 989-993, 991 (V.T. DeVita, Jr. et al. eds., 8th ed., 2008).
Bastian, Genetic Progression, in From Melanocytes to Melanoma the Progression to Malignancy 197, 201 (V.J. Hearing et al., eds., 2006).
Pusztai, Histopathologic and Molecular Markers of Prognosis and Response to Therapy, in Breast Cancer 324, 326-328 (Kelly K. Hunt et al., ed., 2nd ed., 2008).
Cannistra et al., Ovarian Cancer, Fallopian Tube Carcinoma and Peritoneal Carcinoma in, 2 Cancer Principles & Practice of Oncology 1568 (V.T. DeVita, Jr. et al. eds., 8th ed., 2008).
Odunsi et al., Molecular Biology of Gynecological Cancers, in 2 Cancer Principles & Practice of Oncology 1487, 1492 (V.T. DeVita, Jr. et al. eds., 8th ed., 2008).
Libutti, Colon Cancer in, 1 Cancer Principles & Practice of Oncology 1232, 1243 (V.T. DeVita, Jr. et al. eds., 8th ed., 2008).
Kamb, Nature Reviews Drug Discovery 2, 161-165 (2005).
Smith, Molecular Cancer Therapeutics, 6, 428-440, 428 (2007).
Sharpless et al., Nature Reviews Drug Discovery 5, 741-754, 742 (2006).
Abad-Zapatero, Drug Discovery Today, 1-8 (2010).
Olive et al., Clinical Cancer Research 12, 5277-5287 (2006).
Song et al., Cancer a Conceptual Framework in, 1 Cancer Principles & Practice of Oncology 1, 5-6 (V.T. DeVita, Jr. et al. eds., 8th ed., 2008).
Hann et al., Current Opinion in Cell Biology, 13, 778-784 (2001).
Mirozoeva et al., J. Med. Chem. 45, 563-566 (2002).
Byrn et al., Solid-State Chemistry of Drugs, 516 (2nd ed., 1999).
Brittain, Preperation and Identification of Polumorphs and Solvatemorphs, in Preformulation in Solid Dosage Form Development, 185-228, 194 (Moji Christianah Adeyeye and Harry G. Brittain eds., 2008).

Office Action mailed on Apr. 13, 2012 in U.S. Appl. No. 12/863,796.
Office Action mailed on Aug. 27, 2012 in U.S. Appl. No. 12/863,796.
Notice of Allowance issued Dec. 10, 2012 in U.S. Appl. No. 12/863,796.
Taylor et al.; "Tumour necrosis factor α as a therapeutic target for immune-mediated inflammatory diseases;" *Current Opinion in Biotechnology*; 2004; pp. 557-563; vol. 15.
Takami et al.; "Phosphodiesterase inhibitors stimulate osteoclast formation via TRANCE/RANKL expression in osteoblasts: possible involvement of ERK and p38 MAPK pathways;" *FEBS Letters*; 2005; pp. 832-838; vol. 579.
Jourdan et al.; "Tumor necrosis factor is a survival and proliferation factor for human myeloma cells;" *Eur Cytokine Netw.*; Mar. 1999; pp. 65-70; vol. 10, No. 1.
Hirsh et al.; "Phosphodiesterase inhibitors as anti-cancer drugs;" *Biochemical Pharmacology*; 2004; pp. 981-988; vol. 68.
Oster et al.; "Participation of the Cytokines Interleukin 6, Tumor Necrosis Factor-alpha, and Interleukin 1-beta Secreted by Acute Myelogenous Leukemia Blasts in Autocrine and Paracrine Leukemia Growth Control;" *J. Clin. Invest.*; Aug. 1989; pp. 451-457; vol. 84.
Zhang et al.; "Pentoxifylline attenuates cardiac dysfunction and reduces TNF-α level in ischemic-reperfused heart;" *Am J Physiol Heart Circ Physiol*; 2005; pp. H832-H839; vol. 289.
Campos-Toimil et al.; "Short-term or long-term treatments with a phosphodiesterase-4 (PDE4) inhibitor result in opposing agonist-induced $Ca^{2+}$ responses in endothelial cells;" *British Journal of Pharmacology*; 2008; pp. 82-92; vol. 154.
Souza et al.; "Increased Mortality and Inflammation in Tumor Necrosis Factor-Stimulated Gene-14 Transgenic Mice after Ischemia and Reperfusion Injury;" *American Journal of Pathology*; May 2002; pp. 1755-1765; vol. 160, No. 5.
Cardozo et al.; "A Comprehensive Analysis of Cytokine-induced and Nuclear Factor-κB-dependent Genes in Primary Rat Pancreatic β-Cells;" *The Journal of Biological Chemistry*; Dec. 28, 2001; pp. 48879-48886; vol. 276, No. 52.
Sharma et al.; "Tumor Necrosis Factor Alpha (TNF-α) and Estrogen Hormone in Osteoarthritic Female Patients;" *Indian Journal of Clinical Biochemistry*; 2006; pp. 205-207; vol. 21, No. 1.
Banner et al.; "PDE4 inhibition: a novel approach for the treatment of inflammatory bowel disease;" *TRENDS in Pharmacological Sciences*; Aug. 2004; pp. 430-436; vol. 25, No. 8.
Di Giovine et al.; "Urate Crystals Stimulate Production of Tumor Necrosis Factor Alpha from Human Blood Monocytes and Synovial Cells, Cytokine mRNA and Protein Kinetics, and Cellular Distribution;" *The Journal of Clinical Investigation*; Apr. 1991; pp. 1375-1381; vol. 87.
Víctor et al.; "Several Functions of Immune Cells in Mice Changed by Oxidative Stress Caused by Endotoxin;" *Physiol. Res.*; 2003; pp. 789-796; vol. 52.
Hölscher et al.; "Tumor Necrosis Factor Alpha-Mediated Toxic Shock in *Trypanosoma cruzi*-Infected Interleukin 10-Deficient Mice;" *Infection and Immunity*; Jul. 2000; pp. 4075-4083; vol. 68, No. 7.
Tang et al.; "Upregulation of Phosphodiesterase-4 in the Lung of Allergic Rats;" *Am J Respir Crit Care Med.*; 2005; pp. 823-828; vol. 171.
Bäumer et al.; "Highly Selective Phosphodiesterase 4 Inhibitors for the Treatment of Allergic Skin Diseases and Psoriasis;" *Inflammation & Allergy—Drug Targets*; 2006; pp. 17-26; vol. 6.
Reid et al.; "Tumor necrosis factor-α and muscle wasting: a cellular perspective;" *Respir Res*; 2001; pp. 269-272; vol. 2.
Tisdale; "Biology of Cachexia;" *Journal of National Cancer Institute*; Dec. 3, 1997; pp. 1763-1773; vol. 89, No. 23.
Vitale et al.; "The role of Tumor-Necrosis Factor-Alpha (TNF-α) in bone resorption present in middle ear cholesteatoma;" *Rev Bras Otorrinolaringol*; 2007; pp. 117-121; vol. 73, No. 1.
Schmidt et al.; "Closed head injury—an inflammatory disease?" *Brain Research Reviews*; 2005; pp. 388-399; vol. 48.
Sommer et al.; "Mechanisms of neuropathic pain: the role of cytokines;" *Drug Discovery Today: Disease Mechanisms*; 2004; pp. 441-448; vol. 1, No. 4.
Böhm et al.; "Fluorine in Medicinal Chemistry;" *ChemBioChem*; 2004; pp. 637-643; vol. 5.

* cited by examiner

PYRIMIDINE COMPOUNDS AND THEIR USES

RELATED APPLICATIONS

This application is a divisional application of application Ser. No. 12/863,796 filed Sep. 2, 2010, which in turn is a U.S. national stage application of PCT/IB2009/000157 filed Jan. 30, 2009, which claims priority to Indian Application No. 271/CHE/2008 filed Feb. 1, 2008. Each of the prior applications is incorporated herein by reference in its entirety.

FIELD

Described are novel heterocyclic compounds of the general formula (I), their derivatives, analogs, tautomeric forms, stereoisomers, polymorphs, hydrates, solvates, pharmaceutically acceptable salts and compositions, metabolites and prodrugs thereof.

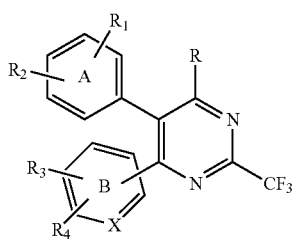

(I)

The present invention also relates to a process for the preparation of the above said novel heterocyclic compounds of the general formula (I).

The novel heterocyclic compounds of the present invention are useful for the treatment of inflammation and immunological diseases. Particularly the compounds of the present invention are useful for the treatment of cancer, inflammation and immunological diseases those mediated by cytokines such as TNF-α, IL-1, IL-6, IL-1β, IL-8, IL-12 and cyclooxygenases such as COX-1, COX-2 and COX-3. More particularly, the compounds of the present invention are useful as PDE4 inhibitors, and are useful for treating PDE4 mediated diseases such as asthma, COPD, IBD, arthritis, psoriasis and the like. They are also useful for the treatment of rheumatoid arthritis; osteoporosis; multiple myeloma; uveititis; acute and chronic myelogenous leukemia; ischemic heart disease, atherosclerosis, cancer, ischemic-induced cell damage, pancreatic β cell destruction; osteoarthritis; rheumatoid spondylitis; gouty arthritis; IBD; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; brain trauma; multiple sclerosis; cerebral malaria; sepsis; septic shock; toxic shock syndrome; fever; myalgias due to infection and diseases mediated by HIV-1; HIV-2; HIV-3; cytomegalovirus (CMV); influenza; adenovirus; the herpes viruses (including HSV-1, HSV-2) and herpes zoster viruses.

BACKGROUND

The present invention is concerned with the treatment of immunological diseases or inflammation, notably such diseases are mediated by cytokines or cyclooygenases. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and provide the necessary "help" for T cell stimulation and proliferation. Most importantly macrophages make IL-1, IL-12 and TNF-α, all of which are potent pro-inflammatory molecules and also provide help for T cells. In addition, activation of macrophages results in the induction of enzymes, such as cyclooxygenase-2 (COX-2) and cyclooxygenase-3 (COX-3), inducible nitric oxide synthase (iNOS) and production of free radicals capable of damaging normal cells. Many factors activate macrophages, including bacterial products, superantigens and interferon gamma (IFN γ). It is believed that phosphotyrosine kinases (PTKs) and other undefined cellular kinases are involved in the activation process.

Cytokines are molecules secreted by the immune cells, large number of chronic and acute conditions have been recognized to be associated with perturbation of the inflammatory responses. A large number of cytokines participate in this response, including IL-1, IL-6, IL-8 and TNF. It appears that the activity of these cytokines in the regulation of inflammation relies at least in part on the activation of an enzyme on the cell-signaling pathway, a member of the MAP known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

Cytokines are molecules secreted by the immune cells that are important in mediating immune responses. Cytokine production may lead to the secretion of other cytokines, altered cellular function, cell division or differentiation. Inflammation is the normal response of the body to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory diseases. TNF-α is a polypeptide hormone released by activated macrophages and other cells. At low concentrations, TNF-α participates in the protective inflammatory response by activating leukocytes and promoting their migration to extravascular sites of inflammation (Moser et al., J Clin Invest, 83, 444-55, 1989). At higher concentrations, TNF-α can act as a potent pyrogen and induce the production of other pro-inflammatory cytokines (Haworth et al., Eur J Immunol, 21, 2575-79, 1991; Brennan et al., Lancet, 2, 244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., Arthritis Rheum, 38, 151-60, 1995). Inhibitors of TNF-α, including soluble TNF receptors, Etanercept (Goldenberg, Clin Ther, 21, 75-87, 1999 and anti-TNF-α antibody) and Infliximab (Luong et al., Ann Pharmacother, 34, 743-60, 2000), are recently approved by the U.S. FDA for the treatment of rheumatoid arthritis.

Elevated levels of TNF-α have also been implicated in many other disorders and disease conditions, including cachexia, septic shock syndrome, osteoarthritis, inflammatory bowel disease (IBD) such as Crohn's disease and ulcerative colitis etc.

Elevated levels of TNF-α and/or IL-1 over basal levels have been implicated in mediating or exacerbating a number of disease states including rheumatoid arthritis; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; type I and type II diabetes; bone resorption diseases; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It can be seen that inhibitors of TNF-α are potentially useful in the treatment of a wide variety of diseases. Compounds that inhibit TNF-α have been described in several patents.

Cytokines play an important role in the communication between cells of multicellular organisms. Early studies indicate that B cells lineage tend to secrete IL-6 in response to host immune defense mechanisms, but in recent decades studies have indicated elevated levels of IL-6 in various cancer phenotypes.

IL-6 has been found to be a growth factor for multiple myeloma cells; anti IL-6 antibodies were shown to block myeloma cell proliferation in leukemic patients Klein et al., Blood, 78, 5, 1198-1204, 1991 and Lu et al., Eur. J. Immunol., 22. 2819-24, 1992.

Elevation of inflammatory cytokine levels, particularly IL-6 and TNF-α also appears to be associated with the cancer-related cachexia, a syndrome involving loss of adipose and skeletal muscle tissue and one that is not responsive to increased caloric intake. Cachexia may also be related to the role of acute phase proteins. The acute phase response and production of acute phase proteins e.g., C-reactive protein (CRP) are mediated by IL-6. Studies correlate elevated levels of IL-6 to elevated acute phase proteins, which interestingly are also associated with increased weight loss and decreased survival. Thus, with elevated IL-6 levels, amino acid metabolism is directed away from peripheral tissues to the liver for production of acute phase proteins, this in turn leads to muscle wasting, which is a component of cachexia. Accordingly, the cytokine-induced acute phase response may be a primary component of cancer-related cachexia. Moreover, diminishing or blocking IL-6 activity in animal models attenuates cachexia, further demonstrating the essential role IL-6 plays in the development of this syndrome.

Thus, having a compound with IL-6 inhibitory activity may be useful for various inflammatory diseases, sepsis, multiple myeloma, plasmacytoid leukemia, osteoporosis, cachexia, psoriasis, Nephritis, Kaposi's sarcoma, rheumatoid arthritis autoimmune disease, endometriosis and solid cancer (WO02/074298 A1). Compounds that inhibit IL-6 have been described in U.S. Pat. Nos. 6,004,813; 5,527,546 and 5,166,137.

The cytokine IL-1β also participates in the inflammatory response. It stimulates thymocyte proliferation, fibroblast growth factor activity and the release of prostaglandins from synovial cells. Elevated or unregulated levels of the cytokine IL-1β have been associated with a number of inflammatory diseases and other disease states, including but not limited to adult respiratory distress syndrome, allergy, Alzheimer's disease etc. Since overproduction of IL-1β is associated with numerous disease conditions, it is desirable to develop compounds that inhibit the production or activity of IL-1β.

In rheumatoid arthritis models in animals, multiple intra-articular injections of IL-1 have led to an acute and destructive form of arthritis (Chandrasekhar et al., Clinical Immunol Immunopathol. 55, 382, 1990). In studies using cultured rheumatoid synovial cells, IL-1 is a more potent inducer of stromelysin than TNF-α. (Firestein, Am. J. Pathol. 140, 1309, 1992). At sites of local injection, neutrophil, lymphocyte and monocyte emigration has been observed. The emigration is attributed to the induction of chemokines (e.g., IL-8) and the up-regulation of adhesion molecules (Dinarello, Eur. Cytokine Netw. 5, 517-531, 1994).

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis, CIA in rats and mice) intra-articular administration of TNF-α either prior to or after the induction of CIA led to an accelerated onset of arthritis and a more severe course of the disease (Brahn et al., Lymphokine Cytokine Res. 11, 253, 1992; and Cooper, Clin. Exp. Immunol. 898, 244, 1992).

IL-8 has been implicated in exacerbating and/or causing many disease states in which massive neutrophil infiltration into sites of inflammation or injury (e.g., ischemia) is mediated; chemotactic nature of IL-8, including, but is not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has ability to activate neutrophils. Thus, reduction in IL-8 levels may lead to diminish neutrophil infiltration.

IL-12 is a heterodimeric cytokine. Consisting of a p40 and a p35 subunit with potent immunoregulatory properties, primarily released by antigen-presenting cells, dendritic cells and monocytes/macrophages in response to bacterial product and immune signals. It enhances natural killer (NK)-mediated cytotoxicity and induces interferon-gamma (IFN-g) production by NK cells and T lymphocytes. IL-12 plays a key role in promoting Th1 immune responses, as demonstrated both in vitro and in vivo. Accordingly, antibodies against IL-12 have been used to beneficial effect in experimental models for auto immune diseases that are Th1-driven, such as experimental allergic encephalomyelitis (EAE) and 2,4,6-trinitrobenzene sulphonic acid (TNBS)-induced chronic intestinal inflammation in mice, a model for human inflammatory bowel disease. In TNBS treated mice, administration of anti-IL-12 after induction of colitis let to a striking improvement of established disease, clinically and histopathologically, associated with a decrease in IFN-g production by ex vivo stimulated lamina propria CD4+ cells. Similarly, anti-IL-12 treatment in C3H mice infected with *Borrelia burgorferi* significantly reduced the severity of Lyme arthritis, accompanied by a decrease in IFN-g serum levels. Several lines of evidence support the critical role of IL-12 in the pathogenesis of CD, including IL-12 expression by mononuclear cells also increased in CD patients versus controls (Kakazu T et al. Am J Gastroenterol. 1999, 94, 2149-2155).

IL-12 production was increased in surgical specimens from CD patients compared with specimens from control patients with cecum cancer (Colpaert S et al. Eur Cytokine Netw. 2002, 13, 431-437). Many clusters of IL-12-positive cells were found in pediatric CD ileal specimens and gastric mucosa, compared with few or no clusters in *H. pylori* gastritis specimens and normal gastric mucosa (Berrebi D et al. Am J Pathol. 1998, 152, 667-672). Substantial proportions of IL-12-containing macrophages were present in the intestinal lamina propria and muscularis propria in active CD, whereas these cells were rarely detected or were undetectable in controls with non-inflammatory gut disorders (Parronchi P et al. Am. J. Pathol. 1997, 150, 823-832). IL-12 p40 mRNA was detected in lamina propria mononuclear cells isolated from 11/13 patients with CD compared with 1/13 healthy controls (P<0.001) (Monteleone G et al. Gastroenterology. 1997, 112, 1169-1178). IL-12 mRNA expression was significantly increased in colonic biopsy specimens from patients with active CD compared with healthy controls (P<0.04) (Nielsen O H et al. Scand. J. Gastroenterol. 2003, 38, 180-185)

It has been reported that the cyclooxygenase enzyme exists in three isoforms, namely, COX-1, COX-2 and COX-3. COX-1 enzyme is essential and primarily responsible for the regulation of gastric fluids whereas COX-2 enzyme is present at the basal levels and is reported to have a major role in the prostaglandin synthesis for inflammatory response. These prostaglandins are known to cause inflammation in the body; hence, if the synthesis of these prostaglandins is stopped by way of inhibiting COX-2 enzyme, inflammation and its related disorders can be treated. COX-3 possesses glycosylation-dependent cyclooxygenase activity. Comparison of canine COX-3 activity with murine COX-1 and COX-2 demonstrated that this enzyme is selectively inhibited by analgesic/antipyretic drugs such as acetaminophen, phenacetin, antipyrine and dipyrone and is potently inhibited by some nonsteroidal anti-inflammatory drugs. Thus, inhibition of COX-3 could represent a primary central mechanism by which these drugs decrease pain and possibly fever. Earlier reports prior to Coxib's development show that inhibitors of COX-1 enzyme causes gastric ulcers, whereas selective COX-2 and COX-3 enzyme inhibitors are devoid of this function and hence are found to be safe. But, recent reports show that the selective COX-2 inhibitors (COXIB's) are associated with cardiovascular risks. So, inhibition of COX-2 without causing cardiovascular risks and gastric ulcers due to inhibition of COX-1 are shown to be safe.

Phosphodiesterases ("PDE") are a family of enzymes that metabolise 3'5' cyclic nucleotides to 5' nucleoside monophosphates thereby terminating camp second messenger activity. A particular phosphodiesterase, phosphodiesterase-4 ("PDE4" also known as "PDE IV"), which is a high affinity, cAMP specific, type IV PDE, has generated interest as potential target for the development of novel anti-asthmatic and anti-inflammatory compounds. PDE4 is known to exist as at least four isoenzymes, each of which is encoded by a distinct gene. Each of the four known PDE4 gene products is believed to play varying roles in allergic and/or inflammatory responses. Thus it is believed that inhibition of PDE4, particularly the specific PDE4 isoforms that produce detrimental responses, can beneficially affect allergy and inflammation symptoms. It would be desirable to provide a method of treatment of rheumatoid arthritis by administering compounds and compositions that inhibit PDE4 activity.

A major concern with the use of PDE4 inhibitors is the side effect of emesis which has been observed for several candidate compounds as described in the patents U.S. Pat. No. 5,622,977, WO 99/50262, U.S. Pat. Nos. 6,410,563 and 5,712,298. It was also described the wide variation of the severity of the undesirable side effects exhibited by various compounds. There is a great interest and research of therapeutic PDE4 inhibitors as described in the above mentioned patents and references cited therein.

PRIOR ART

I) U.S. Pat. No. 6,420,385 discloses novel compounds of the formula (IIa),

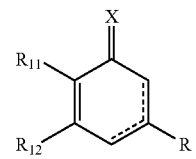

(IIa)

wherein:

represents

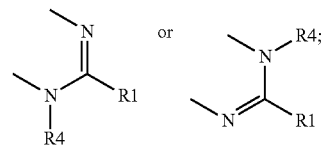

X is O, S or $NR_5$; each of $R_1$ and $R_2$ independently represent —Y or —Z—Y and $R_3$ and $R_4$ each independently represent —Z—Y or $R_3$ is a hydrogen radical; provided that $R_4$ is other than a substituted-aryl, (substituted-aryl)methyl or (substituted-aryl)ethyl radical, wherein each Z is independently optionally substituted alkyl, alkenyl, alkynyl, heterocyclyl, aryl or heteroaryl; Y is independently a hydrogen; halo, cyano, nitro, etc., $R_5$ is independently a hydrogen, optionally substituted alkyl, alkenyl, alkynyl etc., each of $R_{11}$ and $R_{12}$ independently represent optionally substituted aryl or heteroaryl. An example of these compounds is shown in the formula (IIb),

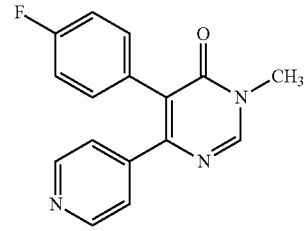

(IIb)

II) U.S. Pat. No. 5,728,704 discloses novel pyrimidines of the formula (I),

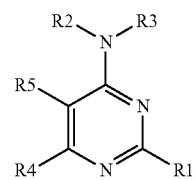

(I)

wherein $R^1$ is hydrogen, $CF_3$, $(C_1$-$C_6)$alkyl, $(C_1$-$C_6)$alkyl-S—$(C_1$-$C_6)$alkyl, $(C_1$-$C_6)$alkyl-SO—$(C_1$-$C_6)$alkyl, $(C_1$-$C_6)$ alkyl-SO$_2$—(C$_1$-C$_6$)alkyl, hydroxy-(C$_1$-C$_6$)alkyl, dihydroxy-(C$_1$-C$_6$)alkyl, C$_1$-C$_6$)alkoxy, (C$_1$-C$_6$)alkoxycarbonyl-(C$_1$-C$_6$)alkyl, aryl selected from phenyl and naphthyl, aryl-(C$_1$-C$_6$)alkyl; R$^2$ and R$^3$ are independently selected from hydrogen, (C$_1$-C$_6$)alkyl, phenyl and phenyl-(C$_1$-C$_4$)alkyl, or R$^2$ and R$^\square$ form, together with the nitrogen to which they are attached, a cyclic group selected from azetidino, pyrrolidino, piperidino, piperazino and morpholino, wherein said cyclic group may optionally be substituted; R$^4$ is hydrogen, chloro, bromo, cyano, nitro, trifluoromethyl, amino, (C$_1$-C$_6$)alkyl, (C$_1$-C$_6$)hydroxyalkyl, (C$_1$-C$_6$)alkoxy, phenyl, naphthyl or furyl, wherein said phenyl, naphthyl and furyl may optionally be substituted; R$^5$ is hydrogen, (C$_1$-C$_6$)alkyl, (C$_1$-C$_6$)alkoxy, trifluoromethyl, (C$_1$-C$_6$)hydroxyalkyl, —S—(C$_1$-C$_6$)alkyl, —SO—(C$_1$-C$_6$)alkyl, —SO$_2$—(C$_1$-C$_6$)alkyl, phenyl or furyl.

III) U.S. Pat. Nos. 6,420,385 and 6,410,729 discloses novel compounds of the formula (IIe),

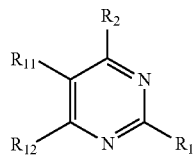

(IIe)

wherein R$_1$ and R$_2$ are each independently —Z—Y, preferably R$_2$ is a radical of hydrogen, C$_1$-C$_4$ alkyl, halo, hydroxy, amino, etc., Z is independently a bond, alkyl, alkenyl etc., Y is independently a hydrogen radical, halo, nitro radical; R$_{20}$ is independently (1) alkyl, alkenyl, heterocyclyl radical, aryl, heteroaryl; R$_{21}$ is independently hydrogen radical, R$_{20}$; R$_{22}$ is independently hydrogen, heterocyclyl, aryl or heteroaryl.

IV) U.S. Pat. No. 7,317,014 discloses novel compounds of the formula (I),

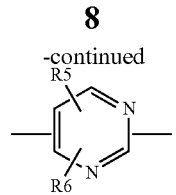

(I)

wherein R1, R2, R3 and R4 may be same or different and independently represent hydrogen, hydroxy, nitro, nitroso, formyl, azido, halo or substituted or unsubstituted groups selected from alkyl, haloalkyl, alkoxy, aryl, aryloxy, aralkyl, aralkoxy, heteroaryl, heterocyclyl, acyl, acyloxy, cycloalkyl, amino, hydrazine, monoalkylamino, dialkylamino, acylamino, alkylsulfonyl, arylsulfonyl, alkylsulfinyl, arylsulfinyl, alkylthio, arylthio, alkoxycarbonyl, aryloxycarbonyl, alkoxyalkyl, sulfamoyl, carboxylic acid and its derivatives; A represents pyrimidine derivative of the formula.

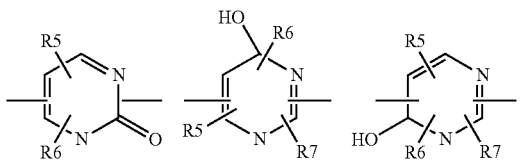

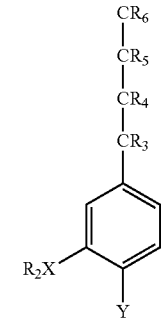

Wherein R5, R6, R7 may be same or different and represent, hydrogen, nitro, nitroso, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsulfonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid and its derivatives; the pyrimidine group may be attached to the phenyl ring through carbon or nitrogen atom.

V) U.S. Pat. No. 5,622,977 describes tri-substituted aryl derivative PDE IV inhibitors with the following general structure.

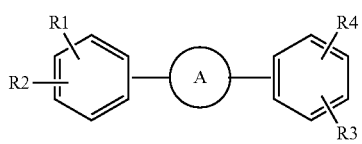

Wherein Y is halogen or OR$_1$, where R$_1$ is a substituted or unsubstituted alkyl; X is —O—, —S—, or —N(R$_8$)—, where R$_8$ is hydrogen or alkyl; R$_2$ is substituted or unsubstituted alkyl, alkenyl, cycloalkyl or cycloakenyl; R$_3$ hydrogen, halogen or OR$_9$, where R$_9$ is hydrogen or substituted or unsubstituted alkyl, alkenyl, alkoxyalkyl, or alkanoyl, formyl carboxamide or thiocarboxamido; R$_4$ and R$_5$ which may be same or different, are each —(CH$_3$)$_n$Ar, where Ar is a monocyclic or bicyclic aryl group or monocyclic or bicyclic heteroaryl and n is integer of 0 to 3; R$_6$ is hydrogen or substituted or unsubstituted alkyl; R$_7$ is hydrogen or substituted or unsubstituted alkyl.

VI) WO 99/50262 describes PDE IV inhibitors, tri-aryl ethane derivatives of the following general structure.

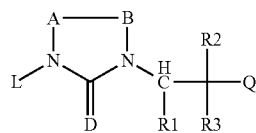

Wherein, L represents hydrogen or substituted or unsubstituted alkyl or aryl; A and B represent independently substituted or unsubstituted carbons joined together by single or double bond; D is oxygen or substituted or unsubstituted nitrogen; Q is substituted or unsubstituted aryl; R1, R2, R3 each independently represent hydrogen, halo, hydroxy, substituted or unsubstituted alkyl, alkoxy and the like.

VII) U.S. Pat. No. 6,410,563 describes 8-arylquinoline compounds that are PDE4 inhibitors.

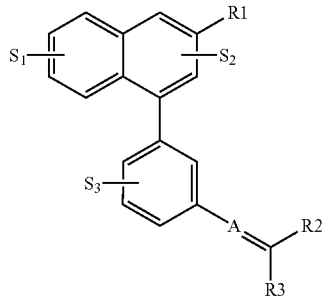

Wherein, $S_1$, $S_2$ and $S_3$ each independently represent hydrogen, halo, hydroxy, substituted or unsubstituted alkyl, alkoxy, and the like; R1, R2, R3 each independently represent hydrogen, halogen, substituted or unsubstituted alkyl, alkoxy, aryl, heteroaryl, substituted or unsubstituted sulfonamide, and the like; A represent substituted or unsubstituted carbon.

VIII) U.S. Pat. No. 5,712,298 describes other PDE4 inhibitors as follows.

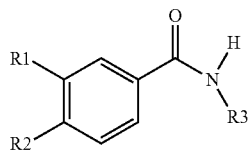

Wherein, R1, R2 each independently represent substituted or unsubstituted hydroxy, alkoxy, and the like, R3 represently substituted or unsubstituted phenyl or aryl, and the like.

IX) WO2007/083182 discloses novel heterocyclic compounds of the formula (I), used for treatment of pain disorder, inflammation and immunological diseases, those mediated by cytokines such as TNF-α, IL-1β and IL-6.

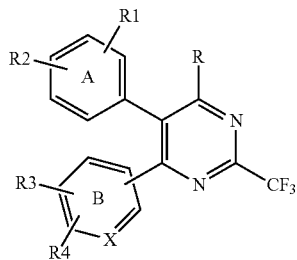

Wherein, A represents substituted or unsubstituted groups selected from aryl; wherein B represents substituted or unsubstituted groups selected from aryl or pyridyl. When B is aryl or pyridyl then R represents substituted or unsubstituted groups selected from aryl, heteroaryl groups, the heteroaryl groups may be selected from pyridyl, thienyl, furyl, pyrrolyl, oxazolyl, thiazolyl, imidazolyl, thiadiazolyl, tetrazolyl, pyrimidinyl, pyrazine, benzofuranyl, benzimidazolyl, benzothiazolyl and the like, aryloxy and heterocyclyl groups such as morpholine, piperazine, piperidine, pyrrolidine, thiazolidine and the like; R1, R2, R3 and R4 represents hydrogen, hydroxy, nitro, azido, halogens, substituted or unsubstituted groups selected from alkyl, haloalkyl, alkoxy, aryl, aryloxy, acyloxy, amino, hydrazine, alkylthio, alkoxycarbonyl, alkoxyalkyl, sulfamoyl, —SO2NHNH2, —SO2Cl, carboxylic acid and its derivatives.

OBJECTIVES

We have focused our research to identify cytokine inhibitors predominantly acting through the inhibition of the TNF-α, which are devoid of any side effects normally associated with TNF-α inhibitors and to identify novel small molecule anticancer agents. Our sustained efforts have resulted in novel heterocyclic compounds of the formula (I). The derivatives may be useful in the treatment of inflammation, cancer and immunological diseases. Particularly the compounds of the present invention are useful for the treatment of immunological diseases those mediated by cytokines such as TNF-α, IL-1, IL-6, IL-1β, IL-8, IL-12 and inflammation. More particularly, the compounds of the present invention are useful as PDE4 inhibitors, and are useful for treating PDE4 mediated diseases. The compounds of the present invention are also useful in the treatment of rheumatoid arthritis; osteoporosis; multiple myeloma; uveititis; acute and chronic myelogenous leukemia; ischemic heart disease; atherosclerosis; ischemic-induced cell damage; pancreatic β-cell destruction; osteoarthritis; rheumatoid spondylitis; gouty arthritis; inflammatory bowel disease; adult respiratory distress syndrome (ARDS); asthma, chronic obstructive pulmonary disorder (COPD); psoriasis; Crohn's disease; allergic rhinitis; ulcerative colitis; anaphylaxis; contact dermatitis; asthma; muscle degeneration; cachexia; bone resorption diseases; ischemia reperfusion injury; brain trauma; multiple sclerosis; sepsis; septic shock; toxic shock syndrome; fever and myalgias due to infection.

SUMMARY

Described are novel heterocyclic compounds of the formula (I),

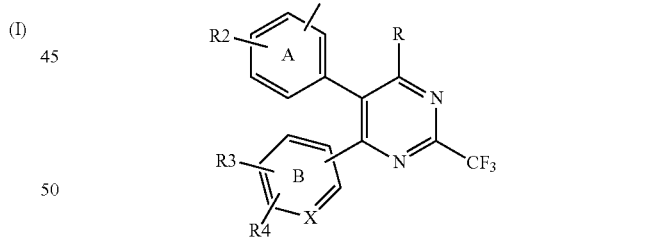

(I)

their derivatives, analogs, tautomeric forms, stereoisomers, polymorphs, solvates, pharmaceutically acceptable salts and pharmaceutical compositions, metabolites and prodrugs thereof, wherein, A represents substituted or unsubstituted aryl groups; B represents substituted or unsubstituted groups selected from aryl or pyridyl; X represents carbon or nitrogen; R represents substituted or unsubstituted groups selected from azido, halogens, alkyl, alkoxy, acyl, cycloalkyl, haloalkyl, amino, hydrazine, monoalkylamino, dialkylamino, acylamino, alkylsulfonyl, alkylsulfinyl, arylsulfonyl, arylsulfinyl, alkoxycarbonyl, aryloxycarbonyl, alkoxyalkyl, sulfamoyl, aryl, heteroaryl, aryloxy, —OSO$_2$R' and heterocyclyl groups; wherein R' represents substituted or unsubstituted groups selected from alkyl, aryl, alkyldialkylamino, haloalkyl, heterocyclyl and heteroaryl groups; $R_1$ represents hydrogen, hydroxy, nitro, formyl, azido, halogens, substituted or unsubstituted groups selected from alkyl, haloalkyl, alkoxy, aryl, aryloxy, acyloxy, amino, hydrazine, monoalkylamino, dialkylamino, acylamino, alkylsulfonyl, alkylsulfinyl, heterocyclylsulfonyl, alkylthio, alkoxycarbonyl, alkoxyalkyl, sulfamoyl, —$SO_2NHNH_2$, —$SO_2Cl$, carboxylic acid and its derivatives; $R_2$ represents hydrogen, hydroxy, nitro, formyl, azido, halogens, substituted or unsubstituted groups selected from alkyl, haloalkyl, alkoxy, aryl, aryloxy, acyloxy, amino, hydrazine, monoalkylamino, dialkylamino, acylamino, alkylsulfonyl, alkylsulfinyl, alkylthio, alkoxycarbonyl, alkoxyalkyl, sulfamoyl, —$SO_2NHNH_2$, —$SO_2Cl$, carboxylic acid and its derivatives; $R_3$ represents hydrogen, hydroxy, nitro, formyl, azido, halogens, substituted or unsubstituted groups selected from alkyl, haloalkyl, alkoxy, aryl, aryloxy, acyloxy, amino, hydrazine, monoalkylamino, dialkylamino, acylamino, alkylsulfonyl, alkylsulfinyl, alkylthio, alkoxycarbonyl, alkoxyalkyl, sulfamoyl, —$SO_2NHNH_2$, —$SO_2Cl$, carboxylic acid and its derivatives; $R_4$ represents hydrogen, hydroxy, nitro, formyl, azido, halogens, substituted or unsubstituted groups selected from alkyl, haloalkyl, alkoxy, aryl, aryloxy, acyloxy, amino, hydrazine, monoalkylamino, dialkylamino, acylamino, alkylsulfonyl, alkylsulfinyl, alkylthio, alkoxycarbonyl, alkoxyalkyl, sulfamoyl, —$SO_2NHNH_2$, —$SO_2Cl$, carboxylic acid and its derivatives.

DETAILED DESCRIPTION

Described are novel heterocyclic compounds of the formula (I),

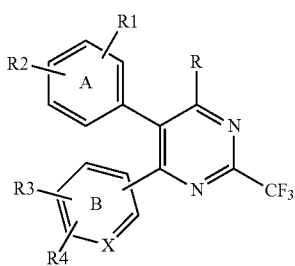

(I)

their derivatives, analogs, tautomeric forms, stereoisomers, polymorphs, solvates, pharmaceutically acceptable salts, compositions, metabolites and prodrugs thereof, wherein A represents substituted or unsubstituted aryl group;

B represents substituted or unsubstituted groups selected from aryl or pyridyl;

X represents carbon or nitrogen atom;

R represents substituted or unsubstituted groups selected from azido; halogens; linear or branched alkyl groups such as methyl, ethyl, n-propyl, isopropyl, n-butyl, isobutyl, t-butyl, n-pentyl, isopentyl, hexyl and the like; alkoxy groups such as methoxy, ethoxy, n-propoxy, isopropoxy, n-butoxy, isobutoxy, t-butoxy and the like; haloalkyl groups such as dichloromethyl, difluoromethyl, trifluoromethyl, trichloromethyl and the like; acyl groups such as acetyl, propanoyl and the like; cycloalkyl groups such as cyclopropyl, cyclobutyl, cyclopentyl and the like; amino; hydrazine; monoalkylamino; dialkylamino; acylamino groups such as acetylamino, propanoylamino and the like; alkylsulfonyl groups such as methylsulfonyl, ethylsulfonyl, propylsulfonyl and the like; alkylsulfinyl; arylsulfonyl; arylsulfinyl; alkoxycarbonyl such as methoxycarbonyl, ethoxycarbonyl and the like; aryloxycarbonyl; alkoxyalkyl; sulfamoyl; aryl groups such as phenyl, naphthyl and the like; heteroaryl groups such as pyridyl, thienyl, furyl, pyrrolyl, pyrazolyl, oxazolyl, thiazolyl, imidazolyl, thiadiazolyl, triazolyl, tetrazolyl, pyrimidinyl, pyrazinyl, benzofuranyl, benzimidazolyl and benzothiazolyl; aryloxy; —$OSO_2R'$ and heterocyclyl groups such as morpholine, thiomorpholine, piperazine, piperidine, piperidin-4-one, pyrrolidine, pyrrol-2,5-dione, thiazolidine, 1-oxido-thiazolidine and 1,1-dioxido-1,3-thiazolidine; the heterocyclyl group is optionally substituted with substitutents independently selected from substituted or unsubstituted alkyl, aryl, heteroaryl, aralkyl (—$CH_2$-aryl), alkylheteroaryl (—$CH_2$-heteroaryl), substituted arylcarbonyl (—CO—Ar), heteroarylcarbonyl (—CO-heteroaryl), heteroarylthiocarbonyl (—CS-heteroaryl), cycloalkylcarbonyl (—CO-cycloalkyl), cyanoalkyl, —O-methyloxime, alkylsulfonyl, haloalkylsulfonyl, haloacyl, —$SO_2Cl$, formyl, hydroxamic acid and another substituted or unsubstituted heterocyclyl group; the attachment of the heterocyclyl group to the pyrimidine ring is through carbon or nitrogen; wherein R' represents substituted or unsubstituted groups selected from alkyl, aryl, alkyldialkylamino, haloalkyl, heterocyclyl and heteroaryl groups;

$R_1$ represents hydrogen; hydroxy; nitro; formyl; azido; halogens; substituted or unsubstituted groups are selected from alkyl; haloalkyl; alkoxy; aryl; aryloxy groups selected from phenoxy and naphthoxy; acyloxy groups such as MeCOO—, EtCOO— and PhCOO—; amino; hydrazine; monoalkylamino; dialkylamino; acylamino; alkylsulfonyl; alkylsulfinyl; alkylthio; alkoxycarbonyl; alkoxyalkyl; sulfamoyl; —$SO_2NHNH_2$; —$SO_2Cl$; carboxylic acid and its derivatives;

$R_2$ represents hydrogen; hydroxy; nitro; formyl; azido; halogens; substituted or unsubstituted groups selected from alkyl; haloalkyl; alkoxy; aryl; aryloxy; acyloxy; amino; hydrazine; monoalkylamino; dialkylamino; acylamino; alkylsulfonyl; alkylsulfinyl; alkylthio; alkoxycarbonyl; alkoxyalkyl; sulfamoyl; —$SO_2NHNH_2$; —$SO_2Cl$; carboxylic acid and its derivatives;

$R_3$ represents hydrogen; hydroxy; nitro; formyl; azido; halogens; substituted or unsubstituted groups selected from alkyl; haloalkyl; alkoxy; aryl; aryloxy; acyloxy; amino; hydrazine; monoalkylamino; dialkylamino; acylamino; alkylsulfonyl; alkylsulfinyl; alkylthio; alkoxycarbonyl; alkoxyalkyl; sulfamoyl; —$SO_2NHNH_2$; $SO_2Cl$; carboxylic acid and its derivatives;

$R_4$ represents hydrogen; hydroxy; nitro; formyl; azido; halogens; substituted or unsubstituted groups selected from alkyl; haloalkyl; alkoxy; aryl; aryloxy; acyloxy; amino; hydrazine; monoalkylamino; dialkylamino; acylamino; alkylsulfonyl; alkylsulfinyl; alkylthio; alkoxycarbonyl; alkoxyalkyl; sulfamoyl; —$SO_2NHNH_2$; —$SO_2Cl$; carboxylic acid and its derivatives;

the groups R, $R_1$, $R_2$, $R_3$, $R_4$ and R' are optionally substituted by one or more substituents selected from halogens; hydroxy; nitro; cyano; ureas; azido; amino; imino-1-phenyl butanone; amide groups such as acetamide, benzamide and the like; thioamide; hydrazine; linear or branched alkyl groups such as methyl, ethyl, n-propyl, isopropyl, n-butyl, isobutyl, t-butyl, n-pentyl, isopentyl, hexyl and the like; alkoxy groups such as methoxy, ethoxy, n-propoxy, isopropoxy, n-butoxy, isobutoxy, t-butoxy and the like; haloalkyl groups such as dichloromethyl, difluoromethyl, trifluoromethyl, trichloromethyl and the like; acyl groups such as acetyl, propanoyl, benzoyl and the like; haloalkoxy groups such as trifluoromethoxy, trifluoroethoxy, trichloromethoxy and the like; cycloalkyl groups such as cyclopropyl, cyclobutyl and the like; haloacyl groups such as trifluoroacetyl, trichloroacetyl and the like; acyloxyacyl; heterocyclyl; aryl; heteroaryl; monoalkylamino; dialkylamino; acylamino; aryloxy groups such as phenoxy, naphthoxy and the like; alkoxycarbonyl groups such as methoxycarbonyl and ethoxycarbonyl; aryloxycarbonyl; alkylsulfonyl; haloalkylsulfonyl; —$SO_2Cl$; arylsulfonyl; alkylsulfinyl; arylsulfinyl; thioalkyl; thioaryl; sulfamoyl; alkoxyalkyl groups; carboxylic acids and its derivatives such as hydroxamic acid, hydroxamates, esters, amides and acid halides; these substituents are further optionally substituted with substituents selected from hydroxy; alkoxy; halogens; alkylsulfonyl; haloalkyl; alkyl and aryl group which in turn is optionally further substituted by halogens and alkyl;

Pharmaceutically acceptable salts include alkali metals like Li, Na, and K, alkaline earth metals like Ca and Mg, salts of organic bases such as diethanolamine, α-phenylethylamine, benzylamine, piperidine, morpholine, pyridine, hydroxyethylpyrrolidine, choline hydroxyethylpiperidine and the like, ammonium or substituted ammonium salts and aluminum salts. Salts also include amino acid salts such as glycine, alanine, cystine, cysteine, lysine, arginine, phenylalanine, guanidine etc. Salts may include acid addition salts where appropriate, which are, sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

The term analog includes a compound, which differs from the parent structure by one or more C, N, O or S atoms. Hence, a compound in which one of the N atoms in the parent structure is replaced by an S atom is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomers include readily interconvertible isomeric forms of a compound in equilibrium. The enol-keto tautomerism is an example.

The term polymorphs include crystallographically distinct forms of compounds with chemically identical structures.

The term pharmaceutically acceptable solvates includes combinations of solvent molecules with molecules or ions of the solute compound.

The term derivative refers to a compound obtained from a compound according to formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation, and the like.

A term once described, the same meaning applies for it, throughout the patent

Representative compounds include:
1. N-({4-[4-Amino-6-[4-(methylsulfonyl)phenyl]-2-(trifluoromethyl)pyrimidin-5-yl]phenyl}sulfonyl)acetamide;
2. 4-{4-Amino-6-[4-(methylsulfonyl)phenyl]-2-(trifluoromethyl)pyrimidin-5-yl}-N-methylbenzenesulfonamide;
3. 4-{4-Chloro-6-[4-(methylsulfonyl)phenyl]-2-(trifluoromethyl)pyrimidin-5-yl}benzenesulfonyl chloride;
4. 4-{4-Chloro-6-[4-(methylsulfonyl)phenyl]-2-(trifluoromethyl)pyrimidin-5-yl}-N-methylbenzenesulfonamide;
5. 4-{4-(Methylamino)-6-[4-(methylsulfonyl)phenyl]-2-(trifluoromethyl)pyrimidin-5-yl}-N-methylbenzenesulfonamide;
6. N-[(4-{4-(Methylamino)-6-[4-(methylsulfonyl)phenyl]-2-(trifluoromethyl)pyrimidin-5-yl}phenyl)sulfonyl]acetamide;
7. 4-{4-Hydrazino-6-[4-(methylsulfonyl)phenyl]-2-(trifluoromethyl)pyrimidin-5-yl}benzenesulfonohydrazide;
8. 4-[4-(4-Fluorophenyl)-6-hydrazino-2-(trifluoromethyl)pyrimidin-5-yl]benzenesulfonohydrazide;
9. N-[(4-{4-Hydrazino-6-[4-(methylsulfonyl)phenyl]-2-(trifluoromethyl)pyrimidin-5-yl}phenyl)sulfonyl]acetamide;
10. 4-{4-Hydrazino-6-[4-(methylsulfonyl)phenyl]-2-(trifluoromethyl)pyrimidin-5-yl}-N-methylbenzenesulfonamide;
11. 4-Hydrazino-5-phenyl-6-pyridin-3-yl-2-(trifluoromethyl)pyrimidine;
12. 4-Hydrazino-5-phenyl-6-pyridin-4-yl-2-(trifluoromethyl)pyrimidine;
13. 5-(4-Fluorophenyl)-4-hydrazino-6-pyridin-4-yl-2-(trifluoromethyl)pyrimidine;
14. 2,2,2-Trifluoro-N'-[5-(4-fluorophenyl)-6-pyridin-4-yl-2-(trifluoromethyl)pyrimidin-4-yl]acetohydrazide;
15. N'-[5-Phenyl-6-pyridin-4-yl-2-(trifluoromethyl)pyrimidin-4-yl]aceto hydrazide;
16. 2,2,2-Trifluoro-N'-[5-phenyl-6-pyridin-4-yl-2-(trifluoromethyl)pyrimidin-4-yl]acetohydrazide;
17. N-[(4-{4-Chloro-6-[4-(methylsulfonyl)phenyl]-2-(trifluoromethyl)pyrimidin-5-yl}phenyl)sulfonyl]acetamide;
18. 6-[4-(Methylsulfonyl)phenyl]-5-phenyl-2-(trifluoromethyl)pyrimidin-4-ylnapthalenesulfonate;
19. 6-[4-(Methylsulfonyl)phenyl]-5-phenyl-2-(trifluoromethyl)pyrimidin-4-yl-3-chloropropane-1-sulfonate;
20. 6-[4-(Methylsulfonyl)phenyl]-5-phenyl-2-(trifluoromethyl)pyrimidin-4-yl-3-(trifluoromethyl)benzenesulfonate;
21. 6-[4-(Methylsulfonyl)phenyl]-5-phenyl-2-(trifluoromethyl)pyrimidin-4-yl-2-(trifluoromethyl)benzenesulfonate;
22. 6-[4-(Methylsulfonyl)phenyl]-5-phenyl-2-(trifluoromethyl)pyrimidin-4-yl-4-methylbenzenesulfonate;
23. 6-[4-(Methylsulfonyl)phenyl]-5-phenyl-2-(trifluoromethyl)pyrimidin-4-yl-4-nitrobenzenesulfonate;
24. 6-[4-(Methylsulfonyl)phenyl]-5-phenyl-2-(trifluoromethyl)pyrimidin-4-yl-4-trifluoromethoxybenzenesulfonate;
25. 6-[4-(Methylsulfonyl)phenyl]-5-phenyl-2-(trifluoromethyl)pyrimidin-4-yl thiophene-2-sulfonate;
26. 6-[4-(Methylsulfonyl)phenyl]-5-phenyl-2-(trifluoromethyl)pyrimidin-4-yl-4-fluorobenzenesulfonate;
27. 6-[4-(Methylsulfonyl)phenyl]-5-phenyl-2-(trifluoromethyl)pyrimidin-4-yl-2-fluorobenzenesulfonate;
28. 6-[4-(Methylsulfonyl)phenyl]-5-phenyl-2-(trifluoromethyl)pyrimidin-4-yl-(dimethylamino)propanesulfonate;
29. 6-[4-(Methylsulfonyl)phenyl]-5-phenyl-4-(N-benzylpiperazin-1-yl)-2-(trifluoromethyl)pyrimidine;
30. 4-[4-(4-Fluorophenyl)-6-piperazin-1-yl-2-(trifluoromethyl)pyrimidin-5-yl]benzenesulfonamide;
31. 4-[5-(4-Fluorophenyl)-6-piperazin-1-yl-2-(trifluoromethyl)pyrimidin-4-yl]benzenesulfonamide;
32. N-Methyl-4-[4-(methylsulfonyl)phenyl]-6-piperazin-1-yl-2-(trifluoromethyl)pyrimidin-5-yl]benzenesulfonamide;
33. 4-[4-(Methylsulfonyl)phenyl]-6-piperazin-1-yl-2-(trifluoromethyl)pyrimidin-5-yl]benzenesulfonamide;

34. 4-{4-(Morpholin-4-yl)-6-[4-(methylsulfonyl)phenyl]-2-(trifluoromethyl)pyrimidin-5-yl}-N-methylbenzenesulfonamide;
35. 5-{4-[4-(Methylsulfonyl)phenyl]-6-piperidin-1-yl-2-(trifluoromethyl)pyrimidin-5-yl}-N-methylbenzenesulfonamide;
36. 4-(4-(Methylsulfonyl)phenyl]-6-{4-[(5-methylpyrazin-2-yl)carbonyl]piperazin-1-yl}-5-phenyl-2-(trifluoromethyl)pyrimidine;
37. 6-[4-(Methylsulfonyl)phenyl]-5-phenyl-4-{4-[(1-methyl-1H-pyrrol-2-yl)carbonyl]piperazin-1-yl}-2-(trifluoromethyl)pyrimidine;
38. 6-[4-(Methylsulfonyl)phenyl]-4-[4-(5-nitro-2-furoyl)piperazin-1-yl]-5-phenyl-2-(trifluoromethyl)pyrimidine;
39. N-Methyl-4-{4-[4-(5-nitro-2-furoyl)piperazin-1-yl]-6-[4-(methylsulfonyl)phenyl]-2-(trifluoromethyl)pyrimidin-5-yl}benzenesulfonamide;
40. 4-{5-[4-Fluorophenyl]-4-[4-(5-nitro-2-furoyl)piperazin-1-yl]-2-(trifluoromethyl)pyrimidin-6-yl}benzenesulfonamide;
41. 4-{6-[4-Fluorophenyl]-4-[4-(5-nitro-2-furoyl)piperazin-1-yl]-2-(trifluoromethyl)pyrimidin-5-yl}benzenesulfonamide;
42. 6-[4-(Methylsulfonyl)phenyl]-4-{4-[(5-nitro-1H-pyrazol-3-yl)carbonyl]piperazin-1-yl}-5-phenyl-2-(trifluoromethyl)pyrimidine;
43. 5,6-Diphenyl-4-[4-(5-nitro-2-furoyl)piperazin-1-yl]-2-(trifluoromethyl)pyrimidine;
44. 5-[4-Fluorophenyl]-4-[4-(5-nitro-2-furoyl)piperazin-1-yl]-6-pyridin-4-yl-2-(trifluoromethyl)pyrimidine;
45. 6-[4-(Methylsulfonyl)phenyl]-5-phenyl-4-[4-(1,3-thiazol-2-ylmethyl)piperazin-1-yl]-2-(trifluoromethyl)pyrimidine;
46. 4-[4-(Methylsulfonyl)phenyl]-5-phenyl-6-[4-(pyridin-4-ylmethyl)piperazin-1-yl]-2-(trifluoromethyl)pyrimidine;
47. 6-[4-(Methylsulfonyl)phenyl]-4-{4-[(5-nitro-2-thienyl)methyl]piperazin-1-yl}-5-phenyl-2-(trifluoromethyl)pyrimidine;
48. 4,5-Diphenyl-6-(4-pyridin-2-yl-piperazin-1-yl)-2-(trifluoromethyl)pyrimidine;
49. 4-[4-(Methylsulfonyl)phenyl]-5-phenyl-6-(4-pyridin-2-yl-piperazin-1-yl)-2-(trifluoromethyl)pyrimidine;
50. 3-[4-(4-Fluorophenyl)-6-piperazin-1-yl-2-(trifluoromethyl)pyrimidin-5-yl]benzenesulfonamide;
51. 3-[4-Phenyl-6-piperazin-1-yl-2-(trifluoromethyl)pyrimidin-5-yl]benzenesulfonamide;
52. 3-[5-(3-Aminosulfonylphenyl)]-6-piperazin-1-yl-2-(trifluoromethyl)pyrimidin-4-yl]benzenesulfonamide;
53. 3-[4-(4-Fluorophenyl)-6-(4-pyridin-2-ylpiperazin-1-yl)-2-(trifluoromethyl)pyrimidin-5-yl]benzenesulfonamide;
54. 3-[4-(4-Fluorophenyl)-6-(4-pyrimidin-2-ylpiperazin-1-yl)-2-(trifluoromethyl)pyrimidin-5-yl]benzenesulfonamide;
55. 3-[5-Phenyl-6-(1,3-thiazolidin-3-yl)-2-(trifluoromethyl)pyrimidin-4-yl]benzenesulfonamide;
56. 3-[6-[(4-Hydroxycyclohexyl)amino]-5-(3-aminosulfonylphenyl)-2-(trifluoromethyl)pyrimidin-4-yl]benzenesulfonamide;
57. 3-[6-(2-Pyrimidin-2-ylpiperazin-1-yl)]-4-phenyl-2-(trifluoromethyl)pyrimidin-5-yl]benzenesulfonamide;
58. 3-[6-(4-Pyridin-2-ylpiperazin-1-yl)]-4-phenyl-2-(trifluoromethyl)pyrimidin-5-yl]benzenesulfonamide;
59. Ethyl-1-[5-(3-aminosulfonylphenyl)-6-(4-fluorophenyl)-2-(trifluoromethyl)pyrimidin-4-yl]piperidine-4-carboxylate;
60. 3-[4-[(4-Hydroxycyclohexyl)amino]-6-(4-fluorophenyl)-2-(trifluoro methyl)pyrimidin-5-yl]benzenesulfonamide;
61. Ethyl 1-[6-phenyl-5-(3-aminosulfonylphenyl)1-2-(trifluoromethyl)pyrimidin-4-yl]piperidine-4-carboxylate;
62. 4-[6-Phenyl-5-(3-morpholinosulfonylphenyl)-2-(trifluoromethyl)pyrimidin-4-yl]morpholine;
63. 3-[4-(4-Fluorophenyl)-6-morpholin-4-yl-2-(trifluoromethyl)pyrimidin-5-yl]benzenesulfonamide;
64. (3R)-1-[6-(4-Fluorophenyl)-5-(3-aminosulfonylphenyl)-2-(trifluoro methyl)pyrimidin-4-yl]pyrrolidin-3-ol;
65. Ethyl (2S,4R)-4-hydroxy-1-[6-(4-fluorophenyl)-5-(3-aminosulfonyl phenyl)-2-(trifluoromethyl)pyrimidin-4-yl]pyrrolidine-2-carboxylate;
66. 4-[4-(2,6-Dimethoxypyrimidin-4-yl)piperazin-1-yl]-5-(3-aminosulfonyl phenyl)-6-(4-fluorophenyl)-2-(trifluoromethyl)pyrimidine;
67. 5-(4-Fluorophenyl)-4-(4-pyridin-2-ylpiperazin-1-yl)-6-[4-(methylsulfonyl)phenyl]-2-(trifluoromethyl)pyrimidine;
68. 4-(4-Methylsulfonylphenyl)-5-(4-fluorophenyl)-6-(4-pyrimidin-2-yl piperazin-1-yl)-2-(trifluoromethyl)pyrimidine;
69. 4-[5-(4-Fluorophenyl)-6-[4-(methylsulfonyl)phenyl]-2-(trifluoromethyl)pyrimidin-4-yl]piperazine-1-carbaldehyde;
70. 1'-[5-(4-Fluorophenyl)-6-(4-methylsulfonylphenyl)-2-(trifluoromethyl)pyrimidin-4-yl]-1,4'-bipiperidine;
71. 3-[4-(4-Fluorophenyl)-6-(1,4'-bipiperidin-1'-yl)-2-(trifluoromethyl)pyrimidin-5-yl]benzenesulfonamide;
72. 3-[4-(2-Furoyl)piperazin-1-yl]-6-(4-fluorophenyl)-2-(trifluoromethyl)pyrimidin-5-yl]benzenesulfonamide;
73. 5-(3-Aminosulfonylphenyl)-4-(4-fluorophenyl)-2-(trifluoromethyl)-6-{4-[3-(trifluoromethyl)phenyl]piperazin-1-yl}pyrimidine;
74. 5-(4-Fluorophenyl)-4-(4-methylsulfonylphenyl)-2-(trifluoromethyl)-6-{4-[3-(trifluoromethyl)phenyl]piperazin-1-yl}pyrimidine;
75. 3-[4-(4-Fluorophenyl)-6-(1,3-thiazolidin-3-yl)-2-(trifluoromethyl)pyrimidin-5-yl]benzenesulfonamide;
76. 1-[5-[3-(Aminosulfonyl)phenyl]-6-(4-fluorophenyl)-2-(trifluoromethyl)pyrimidin-4-yl]pyrrolidine-2-carboxamide;
77. 5-(3-Aminosulfonylphenyl)-4-(4-fluorophenyl)-2-(trifluoromethyl)-6-{4-[(trifluoromethyl)sulfonyl]piperazin-1-yl}pyrimidine;
78. 3-[4-[4-(Methylsulfonyl)piperazin-1-yl]-6-(4-fluorophenyl)-2-(trifluoro methyl)pyrimidin-5-yl]benzenesulfonamide;
79. 3-[4-[4-(Cyanomethyl)piperazin-1-yl]-6-(4-fluorophenyl)-2-(trifluoro methyl)pyrimidin-5-yl]benzenesulfonamide;
80. 3-[4-(4-Fluorophenyl)-6-(1H-imidazol-1-yl)-2-(trifluoromethyl)pyrimidin-5-yl]benzenesulfonamide;
81. 5-(6-(4-Fluorophenyl)-4-(1H-imidazol-1-yl)-6-[4-(methylsulfonyl)phenyl]-2-(trifluoromethyl)pyrimidine;
82. N-({3-[6-(4-Fluorophenyl)-4-(4-pyridin-2-ylpiperazin-1-yl)-2-(trifluoro methyl)pyrimidin-5-yl]phenyl}sulfonyl)propanamide;
83. 3-[6-(4-Fluorophenyl)-4-(morpholin-4-yl)-2-(trifluoromethyl)pyrimidin-5-yl]-N-cyclopropylbenzenesulfonamide;
84. 3-[6-(4-Fluorophenyl)-4-(4-methylpiperazin-1-yl)-2-(trifluoromethyl)pyrimidin-5-yl]benzenesulfonamide;
85. 3-[6-(4-Fluorophenyl)-4-(2-methyl-5-nitro-1H-imidazol-1-yl)-2-(trifluoro methyl)pyrimidin-5-yl]benzenesulfonamide;

86. 3-[6-(4-Fluorophenyl)-4-(4-oxopiperidin-1-yl)-2-(trifluoromethyl)pyrimidin-5-yl]benzenesulfonamide;
87. 3-[4-(Cyclopropylamino)-6-(4-fluorophenyl)-2-(trifluoromethyl)pyrimidin-5-yl]benzenesulfonamide;
88. 3-[6-(4-Fluorophenyl)-4-(4-phenyl-1H-imidazol-1-yl)-2-(trifluoromethyl)pyrimidin-5-yl]benzenesulfonamide;
89. 3-[6-(4-Fluorophenyl)-4-(2,6-dimethylmorpholin-4-yl)-2-(trifluoromethyl)pyrimidin-5-yl]benzenesulfonamide;
90. 3-[6-(4-Fluorophenyl)-4-(2,6-dimethylpiperazin-4-yl)-2-(trifluoromethyl)pyrimidin-5-yl]benzenesulfonamide;
91. 3-[6-(4-Fluorophenyl)-4-(2-methylpiperazin-4-yl)-2-(trifluoromethyl)pyrimidin-5-yl]benzenesulfonamide;
92. 3-[6-(4-Fluorophenyl)-4-(1H-1,2,4-triazol-1-yl)-2-(trifluoromethyl)pyrimidin-5-yl]benzenesulfonamide;
93. 3-[6-(4-Fluorophenyl)-4-(3-amino-1H-pyrazol-1-yl)-2-(trifluoromethyl)pyrimidin-5-yl]benzenesulfonamide;
94. 3-[6-(4-Fluorophenyl)-4-(thiomorpholin-4-yl)-2-(trifluoromethyl)pyrimidin-5-yl]benzenesulfonamide;
95. 3-[6-(4-Fluorophenyl)-4-({2-[(methylsulfonyl)amino]ethyl}amino)-2-(trifluoromethyl)pyrimidin-5-yl]benzenesulfonamide;
96. 3-{6-(4-Fluorophenyl)-4-[3-methyl-4-(methylsulfonyl)piperazin-1-yl]-2-trifluoromethylpyrimidin-5-yl}benzenesulfonamide;
97. 3-{6-(4-Fluorophenyl)-4-[3-(hydroxymethyl)-4-(4-fluorophenyl)piperidin-1-yl]-2-(trifluoromethyl)pyrimidin-5-yl}benzenesulfonamide;
98. 3-[4-Morpholin-4-yl-2-(trifluoromethyl)-6-phenyl-pyrimidin-5-yl]benzenesulfonamide.
99. 3-[6-(4-Fluorophenyl)-4-(2-morpholin-4-ylethoxy)-2-(trifluoromethyl)pyrimidin-5-yl]benzenesulfonamide;
100. 3-{4-[4-(2-Cyanoethyl)piperazin-1-yl]-6-(4-fluorophenyl)-2-(trifluoromethyl)pyrimidin-5-yl}benzenesulfonamide;
101. 3-{6-(4-Fluorophenyl)-4-[3-methyl-4-(pyridin-2-yl-methyl)piperazin-1-yl]-2-(trifluoromethyl)pyrimidin-5-yl}benzenesulfonamide;
102. 3-{6-(4-Fluorophenyl)-4-[3-methyl-4-(3-methoxybenzyl)piperazin-1-yl]-2-(trifluoromethyl)pyrimidin-5-yl}benzenesulfonamide;
103. 3-(6-(4-Fluorophenyl)-4-[4-(pyridin-2-yl-methyl)piperazin-1-yl]-2-(trifluoromethyl)pyrimidin-5-ylbenzenesulfonamide;
104. 3-(6-(4-Fluorophenyl)-[4-(3-methoxybenzyl)piperazin-1-yl]-2-(trifluoro methyl)pyrimidin-5-yl)benzenesulfonamide;
105. 3-{6-(4-Fluorphenyl)-[4-(2-hydroxyethyl)piperazin-1-yl]-2-(trifluoro methyl)pyrimidin-5-yl}benzenesulfonamide;
106. 3-(6-(4-Fluorophenyl)-4-[4-(1H-imidazol-1-ylcarbonothioyl)piperazin-1-yl]-2-(trifluoromethyl)pyrimidin-5-yl)benzenesulfonamide;
107. 3-[4-(1,1-Dioxido-1,3-thiazolidin-3-yl)-6-(4-fluorophenyl)-2-(trifluoro methyl)pyrimidin-5-yl]benzenesulfonamide;
108. 3-[6-(4-Fluorophenyl)-4-(1-oxido-1,3-thiazolidin-3-yl)-2-(trifluoromethyl)pyrimidin-5-yl]benzenesulfonamide;
109. 3-{6-(4-Fluorophenyl)-4-[4-(trifluoroacetyl)piperazin-1-yl]-2-(trifluoro methyl)pyrimidin-5-yl}benzenesulfonamide;
110. 3-{6-(4-Fluorophenyl)-4-[4-(2-fluorobenzoyl)piperazin-1-yl]-2-trifluoromethylpyrimidin-5-yl}benzenesulfonamide;
111. 4-{5-[3-(Aminosulfonyl)phenyl]-6-(4-fluorophenyl)-2-(trifluoromethyl)pyrimidin-4-yl}piperazine-1-sulfonyl chloride;
112. 3-(4-[4-(Cyclopropylcarbonyl)piperazin-1-yl]-6-(4-fluorphenyl)-2-(trifluoromethyl)-pyrimidin-5-yl)benzenesulfonamide;
113. 3-{6-(4-Fluoroophenyl)-4-[4-(methoxyimino)piperidin-1-yl]-2-(trifluoro methyl)pyrimidin-5-yl}benzenesulfonamide;
114. 3-{6-(4-Fluorophenyl)-4-[(3-methyl-2,5-dioxo-2,5-dihydro-1H-pyrrol-1-yl)amino]-2-(trifluoromethyl)pyrimidin-5-yl}benzenesulfonamide;
115. 3-{4-[(2,5-Dioxo-2,5-dihydro-1H-pyrrol-1-yl)amino]-6-(4-fluorophenyl)-2-(trifluoromethyl)pyrimidin-5-yl}benzenesulfonamide;
116. 3-[6-{4-[5-(Trifluoromethyl)pyridin-2-yl]piperazin-1-yl}-4-phenyl-2-(trifluoromethyl)pyrimidin-4-yl]benzenesulfonamide;
117. 3-[6-{4-[2,6-Dimethoxypyrimidin-4-yl]piperazin-1-yl}-4-phenyl-2-(trifluoromethyl)pyrimidin-5-yl]benzenesulfonamide;
118. 3-[6-{4-[5-(Nitro)pyridin-2-yl]piperazin-1-yl}-4-phenyl-2-(trifluoromethyl)pyrimidin-5-yl]benzenesulfonamide;
119. 3-[6-{4-[5-(Amino)pyridin-2-yl]piperazin-1-yl}-4-[4-fluorophenyl]-2-(trifluoromethyl)pyrimidin-5-yl]benzenesulfonamide;
120. 4-[5-(Acetylamino)pyridin-2-yl]piperazin-1-yl-5-(4-fluorophenyl)-6-[4-(methylsulfonyl)phenyl]-2-(trifluoromethyl)pyrimidine;
121. N-({3-[4-Pyridin-2-yl]piperazin-1-yl)-6-(4-fluorophenyl)-2-(trifluoromethyl)pyrimidin-5-yl]phenyl}sulfonyl)acetamide;
122. 4-Fluorophenyl-5-(3-propionylaminosulfonylphenyl)-6-([4-pyridin-2-yl]piperazin-1-yl)-2-(trifluoromethyl)pyrimidine;
123. 1-{5-[3-(Aminosulfonyl)phenyl]-6-(4-fluorophenyl)-2-(trifluoromethyl)pyrimidin-4-yl}piperidine-4-carboxylic acid;
124. 4-[4-(Methoxyaminocarbonyl)piperidin-1-yl]-5-(4-fluorophenyl)-6-[4-(methylsulfonyl)phenyl]-2-(trifluoromethyl)pyrimidine;
125. 1-{5-[3-(Aminosulfonyl)phenyl]-6-(4-fluorophenyl)-2-(trifluoromethyl)pyrimidin-4-yl}-N-hydroxypiperidine-4-carboxamide;
126. Methyl-3-methoxy-4-({6-[4-(methylsulfonyl)phenyl]-5-(4-fluorophenyl)-2-(trifluoromethyl)pyrimidin-4-yl}oxy)benzoate;
127. 3-Methoxy-4-({6-(4-fluorophenyl)-5-[3-(aminosulfonyl)phenyl]-2-(trifluoromethyl)pyrimidin-4-yl}oxy)-N-methoxybenzamide;
128. 4-{[5-(4-Fluorophenyl)-6(4-methylsulfonylphenyl)-2-(trifluoromethyl)pyrimidin-4-yl]oxy}-N,3-dimethoxybenzamide;
129. 5-Amino-1-[5,6-diphenyl-2-(trifluoromethyl)pyrimidin-4-yl]-3-methyl-1H-pyrazole-4-carbonitrile;
130. Ethyl-5-amino-1-[5,6-diphenyl-2-(trifluoromethyl)pyrimidin-4-yl]-3-(methylthio)-1H-pyrazole-4-carboxylate;
131. 5-Amino-1-[5,6-diphenyl-2-(trifluoromethyl)pyrimidin-4-yl]-1H-pyrazole-4-carbonitrile;
132. 3-t-Butyl-1-[5,6-diphenyl-2-(trifluoromethyl)pyrimidin-4-yl]-1H-pyrazol-5-amine;
133. 4-(3,5-Dimethyl-1H-pyrazol-1-yl)-5,6-diphenyl-2-(trifluoromethyl)pyrimidine;
134. 3-[4-(5-Amino-4-cyano-3-methyl-1H-pyrazol-1-yl)-6-(4-fluorophenyl)-2-(trifluoromethyl)pyrimidin-5-yl]benzenesulfonamide;
135. Ethyl-5-amino-1-[5-[3-(aminosulfonyl)phenyl]-6-(4-fluorophenyl)-2-(trifluoromethyl)pyrimidin-4-yl]-3-(methylthio)-1H-pyrazole-4-carboxylate;

136. 4-[4-(Methylsulfonyl)phenyl]-5-phenyl-2-(trifluoromethyl)-6-[5-(trifluoromethyl)-1H-pyrazol-1-yl]pyrimidine;
137. 5-Amino-1-[5,6-diphenyl-2-(trifluoromethyl)pyrimidin-4-yl]-1H-pyrazole-4-carbothioamide;
138. (3Z)-4,4,4-Trifluoro-1-phenylbutane-1,3-dione-3-{[5-phenyl-6-(4-methylsulfonylphenyl)-2-(trifluoromethyl)pyrimidin-4-yl]hydrazone};
139. N-{1-[5,6-Diphenyl-2-(trifluoromethyl)pyrimidin-4-yl]-3-t-butyl-1H-pyrazol-5-yl}-4-methoxybenzamide;
140. N-{1-[5,6-Diphenyl-2-(trifluoromethyl)pyrimidin-4-yl]-3-t-butyl-1H-pyrazol-5-yl}-3-fluorobenzamide;
141. N-{1-[5,6-Diphenyl-2-(trifluoromethyl)pyrimidin-4-yl]-3-t-butyl-1H-pyrazol-5-yl}-4-(trifluoromethyl)benzamide;
142. Ethyl-5-amino-1-[5-phenyl-6-[4-(methylsulfonyl)phenyl]-2-(trifluoromethyl)pyrimidin-4-yl]-3-(methylthio)-1H-pyrazole-4-carboxylate;
143. 5-Amino-1-[5,6-diphenyl-2-(trifluoromethyl)pyrimidin-4-yl]-3-(methyl thio)-N-phenyl-1H-pyrazole-4-carboxamide;
144. 5-Amino-N-(4,5-dimethylphenyl)-1-[5-(4-fluorophenyl)-6-pyridin-4-yl-2-(trifluoromethyl)pyrimidin-4-yl]-3-(methylthio)-1H-pyrazole-4-carboxamide;
145. 1-(2,6-Dichlorophenyl)-3-{1-[5,6-diphenyl-2-(trifluoromethyl)pyrimidin-4-yl]-3-t-butyl-1H-pyrazol-5-yl}urea;
146. 4-[4-(Methylthio)phenyl]-5,6-diphenyl-2-(trifluoromethyl)pyrimidine;
147. 5-Phenyl-4-[4-(methylsulfonyl)phenyl]-6-[4-(methylthio)phenyl]-2-(trifluoromethyl)pyrimidine;
148. 3-[4-(3,5-Dimethylpiperazin-1-yl)-6-phenyl-2-(trifluoromethyl)pyrimidin-5-yl]benzenesulfonamide;
149. 3-{4-[(3S)-3-Methylpiperazin-1-yl]-6-phenyl-2-(trifluoromethyl)pyrimidin-5-yl}benzenesulfonamide;
150. 3-[4-(2,6-Dimethylmorpholin-4-yl)-6-phenyl-2-(trifluoromethyl)pyrimidin-5-yl]benzenesulfonamide;
151. 2,2,2-Trifluoro-N-({3-[6-phenyl-4-(4-(trifluoroacetyl)piperazin-1-yl)-2-(trifluoromethyl)pyrimidin-5-yl]phenyl}sulfonyl)acetamide;
152. 3-[4-(2-Amino-1H-imidazol-1-yl)-6-phenyl-2-(trifluoromethyl)pyrimidin-5-yl]benzenesulfonamide;
153. 5-(4-Chlorophenyl)-6-[4-(methylsulfonyl)phenyl]-4-(piperazin-1-yl)-2-(trifluoromethyl)pyrimidine;
154. 4,5-Diphenyl-6-[4-(methylsulfonyl)piperazin-1-yl]-2-(trifluoromethyl)pyrimidine;
155. 5-(4-Chlorophenyl)-6-[4-(methylsulfonyl)phenyl]-4-(morpholin-1-yl)-2-(trifluoromethyl)pyrimidine;
156. 2-Chloro-4-fluoro-5-({4-[6-(4-methylsulfonylphenyl)-5-phenyl-2-(trifluoromethyl)pyrimidin-4-yl]piperazin-1-yl}sulfonyl)benzoic acid;
157. 2-Chloro-4-fluoro-5-({4-[6-(4-methylsulfonylphenyl)-5-phenyl-2-(trifluoromethyl)pyrimidin-4-yl]piperazin-1-yl}sulfonyl)benzoic acid sodium salt;
158. 4-{4-[(2-Chloro-4-fluorophenyl)sulfonyl]piperazin-1-yl}-6-(4-methylsulfonylphenyl)-5-phenyl-2-(trifluoromethyl)pyrimidine;
159. 4-(4-Methylsulfonylphenyl)-5-phenyl-6-[4-(4-chlorophenyl, phenyl methyl))piperazin-1-yl]-2-(trifluoromethyl)pyrimidine;
160. Ethyl 4-[5-phenyl-6-(4-methylsulfonylphenyl)-2-(trifluoromethyl)pyrimidin-4-yl]piperazine-1-carboxylate;
161. t-Butyl 4-[5-phenyl-6-(4-methylsulfonylphenyl)-2-(trifluoromethyl)pyrimidin-4-yl]piperazine-1-carboxylate;
162. 6-(4-Methylphenyl)-5-phenyl-4-(4-(pyrimidin-2-yl)-piperazin-1-yl)-2-(trifluoromethyl)pyrimidine;
163. 6-(4-Fluorophenyl)-5-phenyl-4-(1,3-thiazolidin-3-yl)-2-(trifluoromethyl)pyrimidine;
164. 6-(4-Fluorophenyl)-5-phenyl-4-(4-(pyrimidin-2-yl)-piperazin-1-yl-2-(trifluoromethyl)pyrimidine;
165. 3-[6-(4-Fluorophenyl)-4-(4-methylpiperazin-1-yl)-2-(trifluoromethyl)pyrimidin-5-yl]benzenesulfonamide;
166. 6-(4-Fluorophenyl)-N-(4-methylpiperazin-1-yl)-5-phenyl-2-(trifluoro methyl)pyrimidin-4-amine;
167. 3-[4-(1H-imidazol-1-yl)-5-phenyl-2-(trifluoromethyl)pyrimidin-6-yl]benzenesulfonamide;
168. 3-[4-(4-Acetylpiperazin-1-yl)-6-(4-Fluorophenyl)-2-(trifluoromethyl)pyrimidin-5-yl]benzenesulfonamide;
169. 1-{5-[3-(Aminosulfonyl)phenyl]-6-phenyl-2-(trifluoromethyl)pyrimidin-4-yl}piperidine-4-carboxylic acid;
170. 3-[6-(4-Fluorophenyl)-4-(thiomorpholin-4-yl)-2-(trifluoromethyl)pyrimidin-5-yl]benzenesulfonamide;
171. N-({3-[4-(4-Acetylpiperazin-1-yl)-6-phenyl-2-(trifluoromethyl)pyrimidin-5-yl]phenyl}sulfonyl)acetamide;
172. 3-[4-(1-Oxido-1,3-thiazolidin-3-yl)-6-phenyl-2-(trifluoromethyl)pyrimidin-5-yl]benzenesulfonamide;
173. 3-{6-Phenyl-4-[4-(trifluoroacetyl)piperazin-1-yl]-2-(trifluoromethyl)pyrimidin-5-yl}benzenesulfonamide;
174. 3-[4-(Cyclopropylamino)-6-(4-methylsulfonylphenyl)-2-(trifluoromethyl)pyrimidin-5-yl]-N-methylbenzenesulfonamide;
175. N-Cyclopropyl-6-(4-fluorophenyl)-5-phenyl-2-(trifluoromethyl)pyrimidin-4-amine;
176. 5-Phenyl-6-(4-methylphenyl)-2-(trifluoromethyl)-4-{4-[5-(trifluoro methyl)pyridin-2-yl]piperazin-1-yl}pyrimidine;
177. 1-[6-(4-Methylphenyl)-5-phenyl-2-(trifluoromethyl)pyrimidin-4-yl]piperidin-4-one;
178. 3-{4-[4-(Hydroxymethyl)piperidin-1-yl]-6-phenyl-2-(trifluoromethyl)pyrimidin-5-yl}benzenesulfonamide;
179. 3-[6-Phenyl-4-(4-oxopiperidin-1-yl)-2-(trifluoromethyl)pyrimidin-5-yl]benzenesulfonamide;
180. 3-(4-[4-(2-Furoyl)piperazin-1-yl]-6-phenyl-2-(trifluoromethyl)pyrimidin-5-yl)benzenesulfonamide;
181. 6-(4-Methylphenyl)-5-phenyl-4-[4-(2-propylpentanoyl)piperazin-1-yl]-2-(trifluoromethyl)pyrimidine;
182. N-Cyclopropyl-6-(4-methylphenyl)-5-phenyl-2-(trifluoromethyl)pyrimidin-4-amine;
183. 4-[6-(4-Fluorophenyl)-4-(4-methylpiperazin-1-yl)-2-(trifluoromethyl)pyrimidin-5-yl]benzenesulfonamide;
184. 4-[6-(4-Fluorophenyl)-4-(morpholin-4-yl)-2-(trifluoromethyl)pyrimidin-5-yl]benzenesulfonamide;
185. 3-[4-(2-Methyl-1H-imidazol-1-yl)-6-phenyl-2-(trifluoromethyl)pyrimidin-5-yl]benzenesulfonamide;
186. 4-{5-[3-(Aminosulfonyl)phenyl]-6-(4-fluorophenyl)-2-(trifluoromethyl)pyrimidin-4-yl}piperazine-1-sulfonyl chloride;
187. 3-(4-[4-(Cyclopropylcarbonyl)piperazin-1-yl]-6-(4-fluorphenyl)-2-(trifluoromethyl)-pyrimidin-5-yl)benzenesulfonamide;
188. 3-[4-(Morpholin-N-yl)-6-(4-fluorophenyl)-2-(trifluoromethyl)pyrimidin-5-yl]-N-cyclopropylbenzenesulfonamide and
189. 6-[4-(Methylsulfonyl)phenyl]-5-phenyl-4-[4-(2-thienylcarbonyl)piperazin-1-yl]-2-(trifluoromethyl)pyrimidine.

According to another embodiment of the present invention, there is provided a process for the preparation of novel heterocyclic compounds of the formula (I),

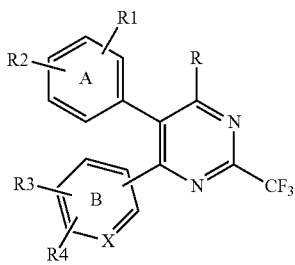

wherein B represents pyridine and R represents a halogen atom and they may be prepared by converting the compound of formula (Ia), wherein all symbols are as defined earlier.

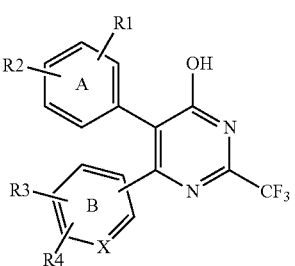

The compound of formula (Ia) is prepared according to the procedure described in our PCT/IB03/01289.

The conversion of the compound of formula (Ia) is carried out using halogenating agents such as phosphorus oxychloride, thionyl chloride, phosphorus trichloride, phosphorus pentachloride and the like in the presence or absence of solvents such as toluene, xylene, tetrahydrofuran, dioxane, chloroform, dichloromethane, dichloroethane, o-dichlorobenzene, diphenyl ether and the like or a mixture thereof, in presence or absence of a catalytic amount of dimethylformamide or N,N-dimethylaniline or N,N-diethylaniline and the like. The reaction is carried out at a temperature in the range of 20° C. to reflux temperatures for a period in the range of 2 to 12 hours.

In yet another embodiment of the present invention, there is provided a process for the preparation of novel heterocyclic compounds of the formula (I)

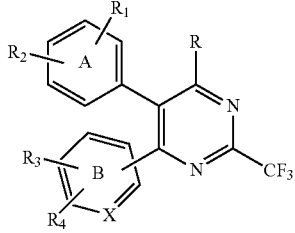

wherein B represents pyridine and R represents azido or hydrazine or substituted hydrazine and they may be prepared by converting the compound of the formula (Ib), wherein all the symbols are as defined earlier.

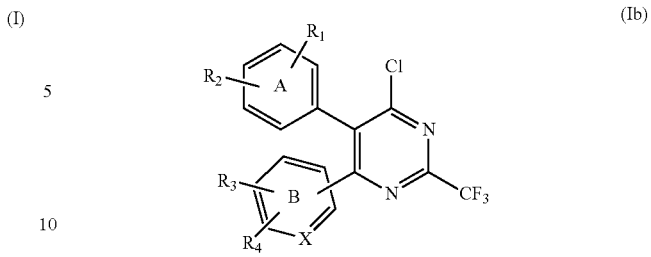

The conversion of the compound of formula (Ib) may be carried out in the presence of one or more equivalents of a metal azide such as $LiN_3$, $NaN_3$, trialkyl silylazide and the like or hydrazine hydrate or substituted hydrazine. The reaction may be carried out in the presence of a solvent such as toluene, xylene, tetrahydrofuran, dioxane, chloroform, dichloromethane, dichloroethane, o-dichlorobenzene, acetone, ethylacetate, acetonitrile, N,N-dimethylformamide, dimethylsulfoxide, ethanol, methanol, isopropylalcohol, t-butylalcohol, diphenyl ether and the like or a mixture thereof. The reaction may be carried out at a temperature in the range of ambient temperature to reflux temperature of the solvent, preferably in the range of 0° C. to 100° C. The reaction time may range from 0.5 to 18 hours.

In yet another embodiment of the present invention, there is provided a process for the preparation of novel heterocyclic compounds of the formula (I),

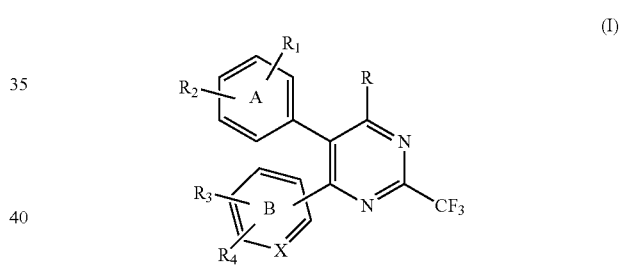

wherein R represents substituted or unsubstituted heterocyclyl groups, and the other symbols are as defined earlier and they may be prepared by converting the compound of formula (Ib), wherein all the symbols are as defined earlier.

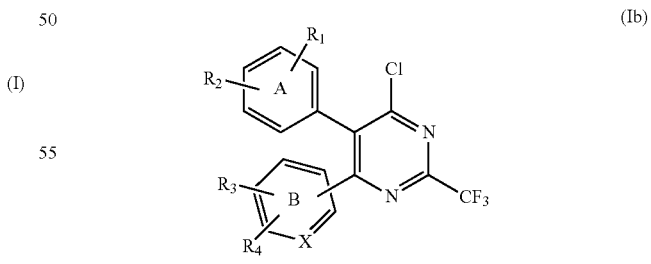

The compound of formula (Ib) is prepared according to the procedure described in our PCT/IB03/02879

The conversion of the compound of the formula (Ib) is carried out with appropriate heterocyclyl or protected heterocyclyl groups such as morpholine, piperazine, benzylpiperazine, piperidine and the like; these heterocyclyl groups may be further substituted with heteroaryl, benzyl, alkyl heteroaryl, other carboxylic acid heterocyclyl groups such as furoic acid, thiophene carboxylic acid, pyrazine carboxylic acid and the like in the presence or absence of appropriate solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, pyridine, diphenyl ether, ethanol, methanol, isopropylalcohol, t-butylalchol, acetic acid, propionic acid etc and the like, or a mixture thereof or by neat reactions. The reaction may be carried out under acidic conditions using mineral or organic acids, or basic conditions viz. carbonates, bicarbonates, hydrides, hydroxides, alkyls and alkoxides of alkali metals and alkaline earth metals. The reaction may be carried out in the presence of $Pd_2(dba)_3$, BINAP, EDCI, HOBT, triethylamine, diisopropylethylamine, DMAP or by using phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product is purified by using chromatographic techniques or by recrystallization. The reaction may be carried out for a time period in the range of 2 to 20 hours.

In yet another embodiment of the present invention, there is provided a process for the preparation of novel heterocyclic compounds of the formula (I)

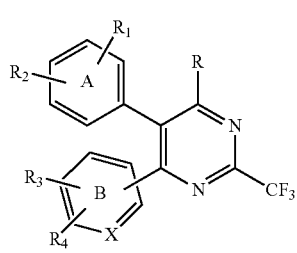

(I)

wherein R represents —$OSO_2R'$ and all the other symbols are as defined above, and may be prepared by converting the compound of formula (Ia), wherein all the other symbols are as defined earlier.

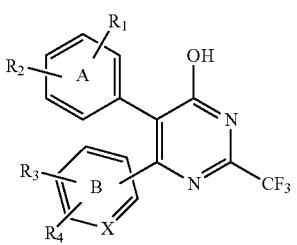

(Ia)

The compound of the formula (Ia) is prepared according to the procedure described in our PCT/IB03/01289.

The conversion of compound of the formula (Ia) is carried out with appropriate heterocyclyl or aryl or alkyl sulfonyl chlorides or sulfonic acids such as naphthalene sulfonyl chloride, naphthalene sulfonyl acid, phenyl sulfonic acid, phenyl sulfonyl chloride, thiophene sulfonyl chloride, thiophene sulfonic acid, propyl sulfonyl chloride, propyl sulfonic acid, chloropropyl sulfonyl chloride and the like in the presence or absence of appropriate solvents like toluene, xylene, tetrahydrofuran, dioxane, chloroform, dichloromethane, dichloroethane, o-dichlorobenzene, acetone, ethyl acetate, acetonitrile, N,N-dimethylformamide, dimethylsulfoxide, pyridine, diphenyl ether, ethanol, methanol, isopropylalcohol, t-butylalchol, acetic acid, propionic acid etc and the like, or a mixture thereof, or by neat reactions. The reaction may be carried out under acidic conditions using mineral or organic acids, or basic conditions viz. carbonates, bicarbonates, hydrides, hydroxides, alkyl and alkoxides of alkali metals and alkaline earth metals. The reaction may be carried out in the presence of phase transfer catalysts viz. triethylbenzylammonium chloride, tetrabutylammonium bromide, tetrabutylammonium hydrogensulphate, tricaprylylmethylammonium chloride (aliquat 336) and the like. The reaction is usually carried out under cooling to refluxing conditions. The final product is purified by using chromatographic techniques or by recrystallization. The reaction may be carried out for a time period in the range of 2 to 20 hours.

In yet another embodiment of the present invention, there is provided a process for the preparation of novel heterocyclic compounds of the formula (I) wherein, $R_1$, $R_2$, $R_3$ and $R_4$ represent $SO_2Cl$ and all other symbols are as defined earlier. It comprises reacting the compound of formula (Ic) wherein all the symbols are as defined earlier and any of $R_1$, $R_2$, $R_3$ and $R_4$ which represents hydrogen on treatment with chlorosulfonic acid is replaced by —$SO_2Cl$; this may result in both possibilities mono/disubstitution.

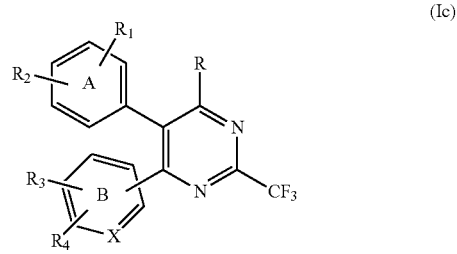

(Ic)

The reaction of the compound of formula (Ic) with chlorosulfonic acid may be carried out in the presence of solvents such as dichloromethane, acetone, tetrahydrofuran, dioxane, ethyl acetate, chloroform and the like or a mixture thereof or in the absence of solvents. The reaction may be carried out at a temperature in the range of 0° C. to reflux temperature for period in the range of 2 to 24 hours.

In yet another embodiment of the present invention, there is provided a process for the preparation of novel heterocyclic compounds of the formula (I), wherein $R_1$, $R_2$, $R_3$ or $R_4$ represent —$SO_2NHCH_3$, —$SO_2NHNH_2$ and all the other symbols are as defined earlier, which comprises reacting the compound of formula (Id), wherein $R_1$, $R_2$, $R_3$ or $R_4$ represents —$SO_2Cl$ and all the other symbols are as defined earlier; with methylamine or appropriate alkylamine or hydrazine hydrate or substituted hydrazine.

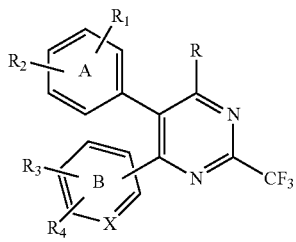

(Id)

The reaction of compound of formula (Id) with alkylamine or the appropriate hydrazine may be carried out in the presence of solvents such as acetonitrile, dichloromethane, acetone, tetrahydrofuran, dioxane, ethyl acetate, chloroform, water, an alcohol and the like or a mixture thereof or in absence of solvents. The reaction may be carried out at a temperature in the range of 0° C. to reflux temperature for period in the range of 2 to 24 hours.

In yet another embodiment of the present invention, there is provided a process for the preparation of novel heterocyclic compounds of the formula (I)

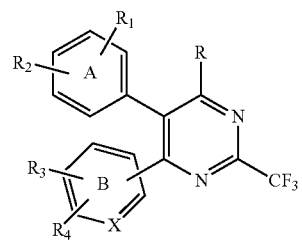

(I)

wherein R represents substituted or unsubstituted heteroaryl groups and the other symbols are as defined earlier and they may be prepared by converting the compound of formula (Ie), wherein all the symbols are as defined earlier.

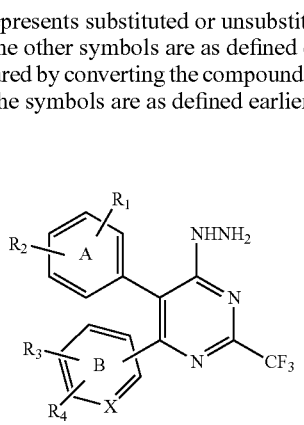

(Ie)

The reaction of (Ie) with reagents such as 1-methoxyethylidene malononitrile, ethyl-2-cyano-3,3-bis(methylthio) acrylate, ethoxymethylene malononitrile, pivaloyl nitrile, acetyl acetone, 1-ethoxyethylidene malononitrile etc., in alcoholic solvents such as ethanol, methanol, isopropanol, butanol etc., or in chlorinated solvents such as dichloromethane, dichloroethane, chloroform etc., or hydrocarbon solvents such as toluene etc., at temperatures ranging from 0 to 200° C. for 0.5 to 24 hours. Some of the heterocyclic compounds thus obtained are further reacted with acyl or aroyl halides such as substituted or unsubstituted benzoyl chlorides in the presence of bases such as triethyl amine, diisopropylamine etc., in chlorinated solvents such as dichloromethane, dichloroethane, chloroform etc., at temperatures ranging from 0 to 100° C. for 0.5 to 24 hours.

The reactions of (Ie) with 1,3-diketones such as acetylacetone, phenyltrifluoroacetyl acetone etc., was carried out in alcoholic solvents such as ethanol, methanol etc., at temperatures ranging from 0 to 150° C. for 0.5 to 24 hours.

In yet another embodiment of the present invention, there is provided a process for the preparation of novel heterocyclic compounds of the formula (I)

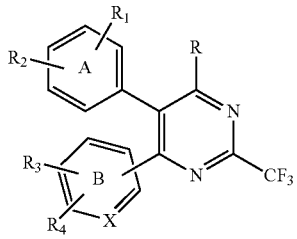

(I)

wherein R represents

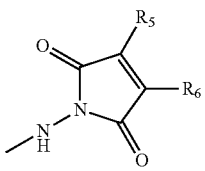

wherein $R_5$ and $R_6$ represent independently hydrogen, alkyl, halo, and the like, and the other symbols are as defined earlier and they may be prepared by converting the compound of formula (Ie), wherein all the symbols are as defined earlier.

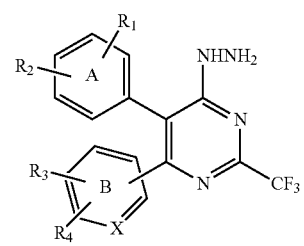

(Ie)

(1e) was treated with corresponding cyclic anhydride and a solvent at room temperature or higher temperature. Anhydrides are selected from methylmaleicanhydride, dimethylmaleicanhydride, dichloromaleic anhydride, and the like. Solvent is selected from dimethylformamide, dichloromethane, chloroform, toluene, and the like. Temperature is in the range of room temperature to 100° C.

The pharmaceutically acceptable salts are prepared by reacting the compound of formula (I) with 1 to 10 equivalents of a base such as sodium hydroxide, sodium methoxide, sodium hydride, potassium t-butoxide, calcium hydroxide, magnesium hydroxide and the like, in solvents like ether, tetrahydrofuran, methanol, t-butanol, dioxane, isopropanol, ethanol etc. Mixture of solvents may also be used. Organic bases such as diethanolamine, α-phenylethylamine, benzylamine, piperidine, morpholine, pyridine, hydroxyethylpyrrolidine, hydroxyethylpiperidine, choline, guanidine and the like, ammonium or substituted ammonium salts, aluminum salts. Amino acids such as glycine, alanine, cystine, cysteine, lysine, arginine, phenylalanine etc may be used for the preparation of amino acid salts. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid, salicylic acid, hydroxynaphthoic acid, ascorbic acid, palmitic acid, succinic acid, benzoic acid, benzenesulfonic acid, tartaric acid, oxalic acid and the like in solvents like ethyl acetate, ether, alcohols, acetone, tetrahydrofuran, dioxane etc. Mixture of solvents may also be used.

It should be noted that compounds of the invention may contain groups that may exist in tautomeric forms and though one form is named, described, displayed and/or claimed herein, all the forms are intended to be inherently included in such name, description, display and/or claim.

The stereoisomers of the compounds forming part of this invention may be prepared by using reactants in their single enantiomeric form, in the process wherever possible or by conducting the reaction in the presence of reagents or catalysts in their single enantiomeric form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid, and the like wherever applicable or by using chiral bases such as brucine, cinchona alkaloids, their derivatives and the like.

Prodrugs of the compounds of formula (I) are also contemplated by this invention. A prodrug is an active or inactive compound that is modified chemically through in-vivo physiological action, such as hydrolysis, metabolism and the like, into a compound of this invention following administration of the prodrug to a patient. The suitability and techniques involved in making and using prodrugs are well known to those skilled in the art.

Various polymorphs of the compounds of the general formula (I), forming part of this invention may be prepared by crystallization of the compounds of formula (I) under different conditions. For example, using different commonly used solvents, or their mixtures for recrystallization; crystallizations at different temperatures; various modes of cooling, ranging from very fast to very slow cooling during crystallizations. Heating or melting the compounds followed by cooling gradually or immediately, one can also obtain polymorphs. The presence of polymorphs may be determined by solid probe NMR spectroscopy, IR spectroscopy, differential scanning calorimetry and powder X-ray diffraction or other such techniques.

Pharmaceutically acceptable solvates of the compounds of the formula (I) forming part of this invention may be prepared by conventional methods such as dissolving the compounds of the formula (I) in solvents such as water, methanol, ethanol, mixture of solvents such as acetone:water, dioxane:water, N,N-dimethylformamide:water and the like, preferably water and recrystallization by using different crystallization techniques The present invention also provides a pharmaceutical composition, containing one or more of the compounds of the general formula (I) as defined above, their derivatives, analogs, tautomeric forms, stereoisomers, polymorphs, hydrates, metabolites, prodrugs, pharmaceutically acceptable salts, pharmaceutically acceptable solvates in combination with the usual pharmaceutically employed carriers, diluents and the like, useful for the treatment of inflammation, arthritis, pain, fever, psoriasis, allergic diseases, asthma, inflammatory bowel syndrome, gastro-intestinal ulcers, cardiovascular disorders including ischemic heart disease, atherosclerosis, cancer, ischemic-induced cell damage, particularly brain damage caused by stroke and other pathological disorders associated with free radicals.

The pharmaceutical composition may be in the forms normally employed, such as tablets, capsules, powders, syrups, solutions, suspensions and the like, may contain flavorants, sweeteners etc. in suitable solid or liquid carriers or diluents, or in suitable sterile media to form injectable solutions or suspensions. The compositions may be prepared by processes known in the art. The amount of the active ingredient in the composition may be less than 70% by weight. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The pharmaceutical compositions of the invention are effective in lowering TNF-$\alpha$, IL-1$\beta$, IL-6 levels, COX-1, and COX-2 activity without causing ulcers. The pharmaceutical compositions of the invention are thus effective for treating rheumatoid arthritis, osteoarthritis, rheumatoid spondylitis, gouty arthritis, inflammatory bowel disease, psoriasis, Crohn's disease, allergic rhinitis, ulcerative colitis, bone resorption diseases and osteoporosis. The pharmaceutical compositions of the invention are also effective in the treatment of ischemic heart disease, ischemic-induced cell damage, ischemia reperfusion injury, atherosclerosis, brain trauma, multiple sclerosis, sepsis, septic shock, toxic shock syndrome, fever and myalgias due to infection. The pharmaceutical compositions of the present invention are also effective in treating cancer, acute and chronic myelogenous leukemia, multiple myeloma, and pancreatic $\beta$ cell destruction. Furthermore, pharmaceutical compositions of the present invention are useful for the treatment of disorders, which includes adult respiratory distress syndrome (ARDS), anaphylaxis, contact dermatitis, asthma, muscle degeneration, cachexia, type I and type II diabetes.

Generally, the effective dose for treating a particular condition in a patient may be readily determined and adjusted by the physician during treatment to alleviate the symptoms or indications of the condition or disease. Generally, a daily dose of active compound in the range of about 0.01 to 1000 mg/kg of body weight is appropriate for administration to obtain effective results. The daily dose may be administered in a single dose or divided into several doses. In some cases, depending upon the individual response, it may be necessary to deviate upwards or downwards from the initially prescribed daily dose. Typical pharmaceutical preparations normally contain from about 0.2 to about 500 mg of active compound of formula I and/or its pharmaceutically active salts or solvates per dose.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The term "therapeutically effective amount" or "effective amount" refers to that amount of a compound or mixture of compounds of Formula I that is sufficient to effect treatment, as defined below, when administered alone or in combination with other therapies to a mammal in need of such treatment. More specifically, it is that amount that is sufficient to lower the cytokines such as TNF-α, IL-1β, IL-6, and to treat autoimmune diseases, inflammation, immunological diseases and cancer.

The term "animal" as used herein is meant to include all mammals and in particular humans. Such animals are also referred to herein as subjects or patients in need of treatment. The therapeutically effective amount will vary depending upon the subject and disease condition being treated, the weight and age of the subject, the severity of the disease condition, the particular compound of Formula I chosen, the dosing regimen to be followed, timing of administration, the manner of administration and the like, all of which can readily be determined by one of ordinary skill in the art.

The term "treatment" or "treating" means any treatment of a disease in a mammal, including:
a) Preventing the disease, that is, causing the clinical symptoms of the disease not to develop;
b) Inhibiting the disease, that is, slowing or arresting the development of clinical symptoms; and/or
c) Relieving the disease, that is, causing the regression of clinical symptoms.

From the foregoing description, one skilled in the art can easily ascertain the essential characteristics of this invention, and without departing from the spirit and scope thereof, make various changes and modifications of the invention to adapt it to various usages and conditions.

In yet another embodiment of the present invention, there is provided biological activity data in tables I to XV for the selected compounds in various in vitro and in vivo methods involving various disease models like Cancer, Psoriasis, Intestinal bowel disease, Arthritis, TNF alpha and PDE4 mediated diseases such as asthma and COPD. Further clinical studies of selected compounds are in progress.

The present invention is provided by the examples given below, which are provided by the way of illustration only and should not be considered to limit the scope of the invention. Variation and changes, which are obvious to one skilled in the art, are intended to be within the scope and nature of the invention, which are defined in the appended claims.

Preparation 1

Preparation of 6-[4-(methylsulfonyl)phenyl]-5-phenyl-2-(trifluoromethyl)pyrimidin-4-amine

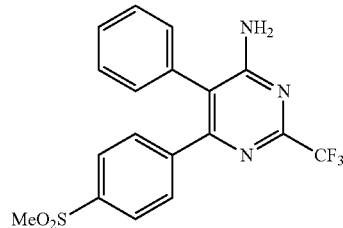 [SMILES: CS(=O)(=O)c1ccc(-c2nc(C(F)(F)F)nc(N)c2-c2ccccc2)cc1]

Ammonia gas was purged through a solution of 4-chloro-6-[4-(methylsulfonyl)phenyl]-5-phenyl-2-(trifluoromethyl) pyrimidine (5.5 g, 13.33 mmol, prepared according to the procedure described in PCT/IB03/02879) in THF (500 ml), continuously for 30 hours under stirring at 0-10° C. After completion of the reaction the THF was distilled completely in-vacuo, water (100 ml) was added and the reaction mixture was extracted with ethyl acetate (3×200 ml). The combined organic layer was washed with brine (150 ml), dried over anhydrous sodium sulphate and concentrated under reduced pressure to give 6-[4-(methylsulfonyl)phenyl]-5-phenyl-2-(trifluoromethyl)pyrimidin-4-amine (3.6 g, yield 87.79%).
The following compounds were prepared according to the above procedure

| Ex. | Structure | Analytical Data |
|---|---|---|
| 1 | H$_3$COCHNO$_2$S—⟨phenyl⟩—pyrimidine(NH$_2$, CF$_3$)—⟨phenyl⟩—H$_3$CO$_2$S; m.p: 153-158° C. | $^1$H-NMR (DMSO-d$_6$) δ: 1.86 (s, 3H), 3.16 (s, 3H), 6.77 (bs, 1H, D$_2$O exchangeable), 7.38-7.55 (m, 2H), 7.59-7.73 (m, 2H), 7.75-7.86 (m, 5H), 12.04 (s, 1H, D$_2$O exchangeable). IR (KBr) cm$^{-1}$: 3472, 3342, 3204, 1715 and 1630; MS m/z: 515.1 (M$^+$ + 1). |

-continued

| Ex. | Structure | Analytical Data |
|---|---|---|
| 2 | H₃CHNO₂S—〈phenyl〉—pyrimidine(NH₂, CF₃)—〈phenyl〉—SO₂CH₃<br>m.p: 272-276° C. | ¹H-NMR (DMSO-d₆) δ: 2.04-2.05 (d, 3H), 3.16 (s, 3H), 6.66 (bs, D₂O exchangeable), 7.29-7.30 (m, 1H, D₂O exchangeable), 7.42-7.45 (m, 3H), 7.61-7.7 (m, 2H), 7.72-7.77 (m, 3H), 8.11 (bs, 1H, D₂O exchangeable). IR (KBr) cm⁻¹: 3423, 3339, 3242, 1639 and 1579; MS m/z: 487.2 (M⁺ + 1). |

Example 3

Synthesis of 4-{4-chloro-6-[4-(methylsulfonyl)phenyl]-2-(trifluoromethyl)pyrimidin-5-yl}benzenesulfonyl chloride

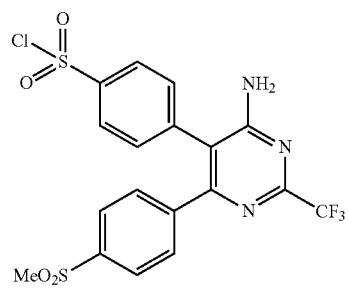 [SMILES: CS(=O)(=O)c1ccc(-c2nc(C(F)(F)F)nc(N)c2-c2ccc(S(=O)(=O)Cl)cc2)cc1]

To a solution of chlorosulphonic acid (605 mmol, 40.4 ml) was added 4-chloro-6-[4-(methylsulfonyl)phenyl]-5-phenyl-2-(trifluoromethyl)pyrimidine (5.0 g, 12.1 mmol, prepared according to the procedure described in PCT/IB03/02879) slowly under continuous stirring at 0° C. until the completion of the addition. The reaction mixture was further stirred at 32° C. until TLC confirmed the completion. Subsequently the resulting reaction mass was poured slowly under vigorous stirring onto crushed ice and the solid obtained was filtered, washed thoroughly with water (100 ml) and extracted with ethyl acetate (3×200 ml). The combined organic layer was washed with brine (150 ml), dried over anhydrous sodium sulphate and concentrated under reduced pressure to afford 4-[4-chloro-6-[4-(methylsulfonyl)phenyl]-2-(trifluoromethyl)pyrimidin-5-yl]benzenesulfonyl chloride (2.75 g, yield 65.59%, purity by HPLC 98.17%); m.p: 207-210° C. ¹H-NMR (400 MHz, CDCl₃) δ: 3.01 (s, 3H), 7.511-7.515 (d, 2H), 7.53-7.67 (m, 1H), 7.72-7.76 (t, 1H), 7.86-7.89 (m, 3H), 8.11-8.13 (d, 1H). IR (KBr) cm⁻¹: 1557, 1524; MS m/z: 511.6 (M⁺).

Example 4

Synthesis of 4-{4-chloro-6-[4-(methylsulfonyl)phenyl]-2-(trifluoromethyl)pyrimidin-5-yl}-N-methyl-benzenesulfonamide

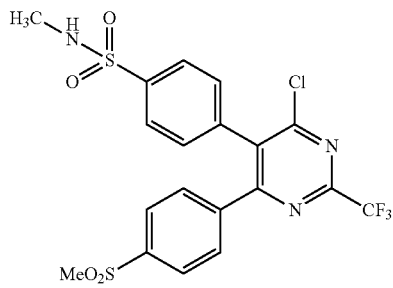 [SMILES: CNS(=O)(=O)c1ccc(-c2c(Cl)nc(C(F)(F)F)nc2-c2ccc(S(C)(=O)=O)cc2)cc1]

To a solution of 4-{4-chloro-6-[4-(methylsulfonyl)phenyl]-2-(trifluoromethyl)pyrimidin-5-yl}benzenesulfonyl chloride (0.5 g, 0.98 mmol, prepared according to the procedure described for example 3) in dichloromethane (5 ml) was added methylamine solution (0.08 ml, 0.98 mmol, 40% aqueous solution) under stirring at 0-10° C. After 15 minutes of the stirring, TLC confirmed the completion of the reaction. Subsequently the solvent was distilled off under reduced pressure and the solid thus obtained was filtered, washed thoroughly with cold water to yield the title compound (0.446 g, yield 90.1%, purity by HPLC 98.1%). m.p: 226-230° C. ¹H-NMR (400 MHz, DMSO-d₆) δ: 2.09-2.10 (d, 3H), 3.1 (s, 3H), 7.43-7.44 (m, 1H, D₂O exchangeable), 7.54-7.56 (d, 2H), 7.69-7.81 (m, 4H), 7.86-7.88 (d, 2H). IR (KBr) cm⁻¹: 3335, 1562 and 1530; MS m/z: 506.1 (M⁺+1).

The following compounds were prepared according to the procedure described for example 4

| Ex. | Structure | Analytical Data |
|---|---|---|
| 5. | 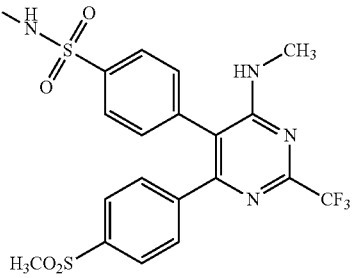 m.p: 265-276° C. | $^1$H-NMR (DMSO-$d_6$) δ: 2.03-2.04 (d, 3H), 2.85-2.87 (d, 3H), 3.15 (s, 3H), 7.12 (s, 1H, $D_2O$ exchangeable), 7.13-7.31 (m, 1H, $D_2O$ exchangeable), 7.32-7.44 (m, 3H), 7.64-7.4 (m, 2H), 7.75-7.77 (m, 3H). IR (KBr) cm$^{-1}$: 3372, 3326, 1589 and 1551; MS m/z: 501.2 ($M^+$ + 1). |
| 6 | 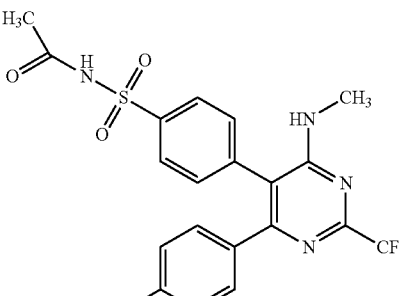 m.p: >285° C. | $^1$H-NMR (DMSO-$d_6$) δ: 1.18 (s, 3H), 2.85-2.86 (d, 3H), 3.16 (s, 3H), 7.08-7.09 (m, 1H, $D_2O$ exchangeable), 7.4-7.42 (m, 2H), 7.55-7.57 (m, 1H), 7.62-7.66 (m, 1H), 7.72-7.76 (3H), 7.87-7.89 (d, 1H), 12.04 (s, 1H, $D_2O$ exchangeable). IR (KBr) cm$^{-1}$: 3413, 3151, 1719 and 1588; MS m/z: 529 ($M^+$ + 1). |

Example 7

Synthesis of 4-{4-hydrazino-6-[4-(methylsulfonyl)phenyl]-2-(trifluoromethyl)pyrimidin-5-yl}benzenesulfonohydrazide

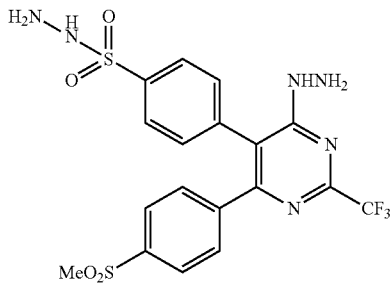 [SMILES: CS(=O)(=O)c1ccc(-c2nc(C(F)(F)F)nc(NN)c2-c2ccc(S(=O)(=O)NN)cc2)cc1]

To a suspension of 4-{4-chloro-6-[4-(methylsulfonyl)phenyl]-2-(trifluoro methyl)pyrimidin-5-yl}benzenesulfonyl chloride (1 g, 1.9 mmol, prepared according to the procedure described for Example 3) in ethanol (10 ml) was added hydrazine hydrate (0.195 g, 3.9 mmol), at 0-10° C. under stirring. The stirring was continued at the same temperature for 3 hours until TLC using ethyl acetate and hexane as solvent system confirmed the completion of the reaction. The solid that reappeared was filtered and washed with ethanol (5 ml) and finally with hexane (10 ml) to afford the desired compound (0.9 g, yield 91.56%, purity by HPLC 94.49%); m.p. 203-206° C. $^1$H-NMR (DMSO-$d_6$) δ: 3.17 (s, 3H), 4.0 (s, 2H, $D_2O$ exchangeable), 7.44-7.46 (d, 3H), 7.59-7.64 (m, 1H), 7.76-7.77 (d, 3H), 8.33s, 1H), 8.44 (s, 1H, $D_2O$ exchangeable). IR (KBr) cm$^{-1}$: 3353, 1581, 1567; MS m/z: 503.1 ($M^+$+1).

The following compounds were prepared according to the procedure described for example 7

| Ex. | Structure | Analytical Data |
|---|---|---|
| 8 | (structure shown) m.p: 183-184° C. | ¹H-NMR (DMSO-d₆) δ: 4.04 (s, 2H, D₂O exchangeable), 4.37 (s, 2H, D₂O exchangeable), 7.05-7.1 (m, 2H), 7.18-7.27 (m, 3H), 7.41-7.43 (m, 2H), 7.59-7.63 (m, 1H), 8.30-8.35 (m, 1H, D₂O exchangeable), 8.77 (bs, 1H, D₂O exchangeable); MS m/z: 443 (M⁺ + 1) |
| 9 | (structure shown) m.p: 255-257° C. | ¹H-NMR (DMSO-d₆) δ: 1.87 (s, 3H), 3.16 (s, 3H), 4.65 (bs, 2H, D₂O exchangeable), 7.4-7.5 (m, 3H), 7.57-7.61 (m, 1H), 7.71-7.80 (m, 3H), 7.84-7.86 (d, 1H), 8.52 (s, 1H), 12.05 (s, 1H, D₂O exchangeable). IR (KBr) cm⁻¹: 3388, 3209, 1734, 1583; MS m/z: 530 (M⁺ + 1). |
| 10 | (structure shown) m.p: 252-254° C. | ¹H-NMR (DMSO-d₆) δ: 2.06-2.07 (d, 3H), 3.15-3.17 (s, 3H), 4.61 (bs, 2H, D₂O exchangeable), 7.28-7.32 (m, 1H), 7.42-7.44 (m, 3H), 7.55-7.65 (m, 2H), 7.7-7.79 (m, 3H), 8.53 (s, 1H, D₂O exchangeable); MS m/z: 502.2 (M⁺ + 1). |
| 11 | (structure shown) m.p: 141-144° C. | ¹H-NMR (CDCl₃) δ: 4.09 (bs, 2H, D₂O exchangeable), 6.27 (s, 1H, D₂O exchangeable), 7.16-7.19 (m, 3H), 7.41-7.72 (m, 3H), 7.25-7.74 (m, 1H), 8.47-8.5 (m, 2H); MS m/z: 332 (M⁺ + 1). |

| Ex. | Structure | Analytical Data |
|---|---|---|
| 12 | 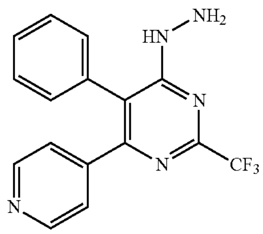 | ¹H-NMR (CDCl₃) δ: 4.08 (bs, 2H, D₂O exchangeable), 6.28 (s, 1H, D₂O exchangeable), 7.13-7.18 (m, 2H), 7.21-7.22 (m, 2H), 8.46 (s, 3H), 8.46-8.47 (m, 2H); MS m/z: 332 (M⁺ + 1). |
| | m.p: 156-159° C. | |
| 13 | 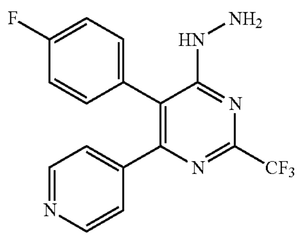 | ¹H-NMR (CDCl₃) δ: 4.09 (bs, 2H, D₂O exchangeable), 6.24 (s, 1H, D₂O exchangeable), 7.14-7.16 (m, 4H), 7.18-7.20 (m, 2H), 8.49-8.5 (d, 2H); MS m/z: 350.2 (M⁺ + 1). |
| | m.p: 187-189° C. | |

Example 14

Synthesis of 2,2,2-trifluoro-N'-[5-(4-fluorophenyl)-6-pyridin-4-yl-2-(trifluoro methyl)pyrimidin-4-yl] acetohydrazide

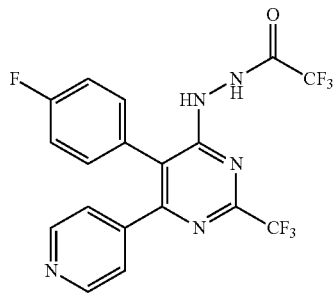 [SMILES: O=C(NNc1nc(C(F)(F)F)nc(-c2ccncc2)c1-c1ccc(F)cc1)C(F)(F)F]

To a solution of 5-(4-fluorophenyl)-4-hydrazino-6-pyridin-4-yl-2-(trifluoromethyl)pyrimidine (0.5 g, 1.43 mmol, example 13, prepared according to the procedure described for example 7) in dichloromethane (10 ml) was added trifluoroacetic anhydride (0.22 ml, 1.57 mmol) under stirring at −40° C. The stirring was continued at the same temperature for 30 minutes, until TLC using ethyl acetate and hexane (3:7) as solvent system confirmed the completion of the reaction. Subsequently the reaction mixture was poured onto ice and extracted with ethyl acetate (50 ml), dried over anhydrous sodium sulphate and evaporated to afford the desired compound (0.34 g, yield 53.3%, purity by HPLC 97%); m.p. 240-242° C. ¹H-NMR (DMSO-d₆) (δ: 7.17-7.35 (m, 6H), 8.49-8.50 (d, 2H), 9.3 (s, 1H), 11.7 (s, 1H, D₂O exchangeable). IR (KBr) cm⁻¹: 3678, 3395, 3208 and 1742; MS m/z: 446.1 (M⁺+1).

Following compounds were prepared according to the procedure described for example 14

| Ex. | Structure | Analytical data |
|---|---|---|
| 15 | 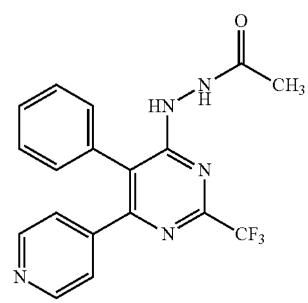 | ¹H-NMR (CDCl₃) δ: 2.12 (s, 3H), 7.21-7.22 (m, 2H), 7.46-7.47 (m, 3H), 8.0 (s, 1H), 8.48-8.49 (d, 2H); IR (KBr) cm⁻¹: 3257, 1694, 1577 and 1571; MS m/z: 374 (M⁺ + 1). |
| | m.p: 197-198° C. | |
| 16 | 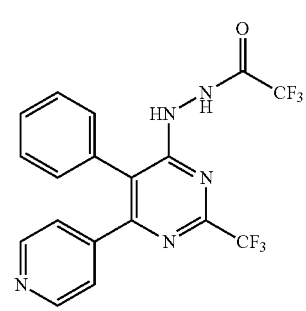 [SMILES: O=C(NNc1nc(C(F)(F)F)nc(-c2ccncc2)c1-c1ccccc1)C(F)(F)F] | ¹H-NMR (DMSO-d₆) δ: 7.21-7.22(m, 2H), 7.27-7.29 (m, 2H), 7.42-7.43 (d, 2H), 9.26 (s, 1H, D₂O exchangeable), 10.8 (s, 1H, D₂O exchangeable); MS m/z: 428 (M⁺ + 1). |

Example 17

Synthesis of N-[(4-{4-chloro-6-[4-(methylsulfonyl)phenyl]-2-(trifluoromethyl)pyrimidin-5-yl}phenyl)sulfonyl]acetamide

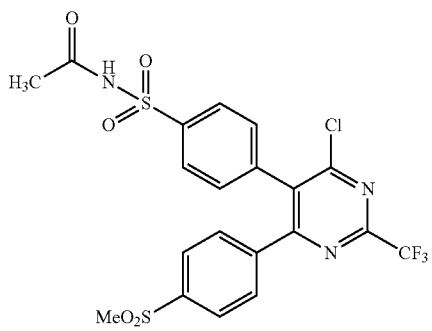 [SMILES: CC(=O)NS(=O)(=O)c1ccc(-c2c(Cl)nc(C(F)(F)F)nc2-c2ccc(S(C)(=O)=O)cc2)cc1]

A solution of 4-{4-chloro-6-[4-(methylsulfonyl)phenyl]-2-(trifluoromethyl)pyrimidin-5-yl}benzenesulfonamide (0.5 g, 1.01 mmol, prepared according to the procedure described in PCT/IB03/02879), DMAP (0.01 g) and acetyl chloride (0.5 g, 6.36 mmol) were stirred at 30° C. TLC confirmed the completion of the reaction after 4 hours of stirring under the same conditions. Subsequently the resulting mass was poured onto the ice and the procedure described for example 14 was followed to afford the title compound (0.252 g, 46.41%, purity by HPLC 98.82%); m.p.: 230-235° C. $^1$H-NMR (DMSO-$d_6$) δ: 1.87 (s, 3H), 3.17 (s, 3H), 7.51-7.53 (m, 2H), 7.66-7.67 (m, 2H), 7.8-7.82 (d, 2H), 7.9 (s, 1H), 7.99 (s, 1H), 12.14 (s, 1H, D$_2$O exchangeable); IR (KBr) cm$^{-1}$: 3150, 1720 and 1525; MS m/z: 533.7 (M$^+$).

Example 18

Synthesis of 6-[4-(methylsulfonyl)phenyl]-5-phenyl-2-(trifluoromethyl)pyrimidin-4-yl napthalenesulfonate

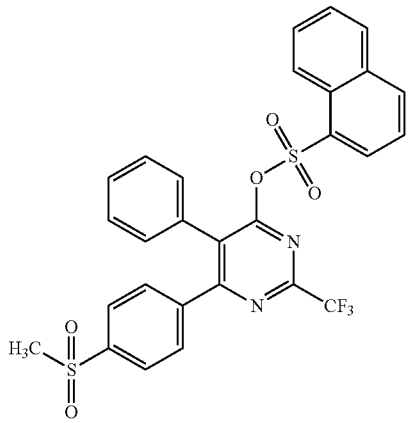 [SMILES: CS(=O)(=O)c1ccc(-c2nc(C(F)(F)F)nc(OS(=O)(=O)c3cccc4ccccc34)c2-c2ccccc2)cc1]

To a solution of 6-[4-(methylsulfonyl)phenyl]-5-phenyl-2-(trifluoromethyl)pyrimidin-4-ol (0.1 g, 0.25 mmol, prepared according to the procedure described in PCT/IB03/01289) in dichloromethane (10 ml) was added naphthalene-1-sulfonyl chloride (0.086 g, 0.37 mmol) in dichloromethane (4 ml) at 0° C. and the mixture was stirred for 10 minutes. Subsequently pyridine (0.04 ml, 0.5 mmol) was added under stirring and the stirring was continued further for 6 hours at 37° C. Dichloromethane was removed under vacuo and the resultant mixture was diluted with water:ethyl acetate (1:1, 100 ml) and then extracted with ethyl acetate (3×25 ml). The organic layer was washed with brine (100 ml), dried over anhydrous sodium sulphate and evaporated to afford the title compound (0.096 g, yield 67%); m.p. 204-206° C. $^1$H-NMR (CDCl$_3$) δ: 2.99 (s, 3H), 7.12-7.14 (d, 2H), 7.26-7.29 (dd, 3H), 7.37-7.39 (m, 2H), 7.48-7.50 (m, 2H), 7.61-7.64 (m, 3H), 7.77-7.79 (d, 2H), 7.84-7.86 (d, 2H), 7.94-7.96 (d, 2H); MS m/z: 585.1 (M$^+$+1).

The following compounds were prepared according to the procedure described for Example 18

| Ex. | Structure | Analytical Data |
|---|---|---|
| 19 |  m.p: 202-204° C. | $^1$H-NMR (CDCl$_3$) δ: 2.42-2.45 (m, 2H), 2.99 (s, 3H), 3.68-3.71 (t, 2H), 3.97-4.01 (t, 2H), 7.19-7.86 (m, 9H); MS m/z: 535.5 (M$^+$ + 1). |

| Ex. | Structure | Analytical Data |
| --- | --- | --- |
| 20 | 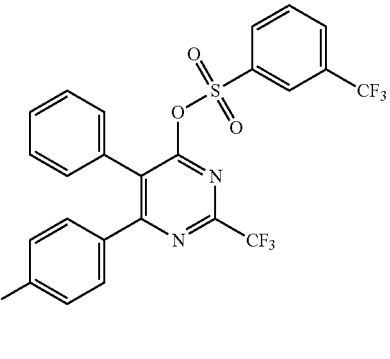 m.p: 174-176° C. | $^1$H-NMR (CDCl$_3$) δ: 3.02 (s, 3H), 7.18-7.20 (d, 2H), 7.21-7.26 (dd, 3H), 7.41-7.43 (m, 2H), 7.55-7.57 (dd, 1H), 7.76-7.81 (dd, 2H), 7.97-8.44 (m, 3H); MS m/z: 603.54 (M$^+$ + 1). |
| 21 | 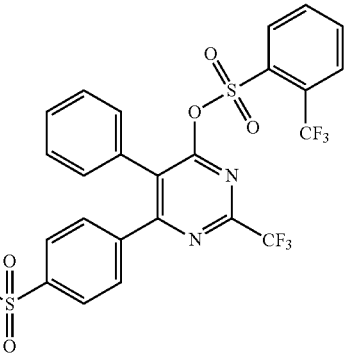 m.p: 174-176° C. | $^1$H-NMR (CDCl$_3$) δ: 3.02 (s, 3H), 7.17-7.20 (d, 2H), 7.21-7.26 (dd, 3H), 7.40-7.43 (m, 2H), 7.81-7.83 (m, 4H), 7.84-7.86 (dd, 1H), 8.41-8.43 (dd, 1H); MS m/z: 603.51 (M$^+$ + 1). |
| 22 | 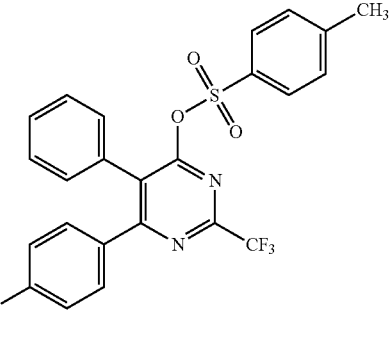 m.p: 200-206° C. | $^1$H-NMR (CDCl$_3$) δ: 2.47 (s, 3H), 3.02 (s, 3H), 7.17-7.20 (d, 2H), 7.21-7.26 (dd, 3H), 7.40-7.43 (m, 2H), 7.81-7.83 (m, 4H), 7.84-7.86 (dd, 1H), 8.41-8.43 (dd, 1H); MS m/z: 603.51 (M$^+$ + 1). |

| Ex. | Structure | Analytical Data |
| --- | --- | --- |
| 23 | 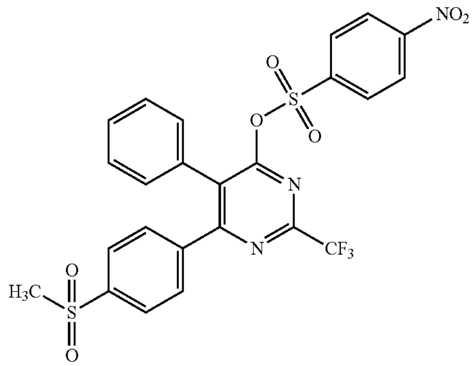 | $^1$H-NMR (CDCl$_3$) δ: 3.02 (s, 3H), 7.18-7.20 (d, 2H), 7.21-7.26 (dd, 3H), 7.41-7.43 (m, 2H), 7.55-7.57 (dd, 1H), 7.76-7.81 (dd, 2H), 7.97-8.44 (m, 3H); MS m/z: 603.54 (M$^+$ + 1). |
| | m.p: 205-208° C. | |
| 24 | 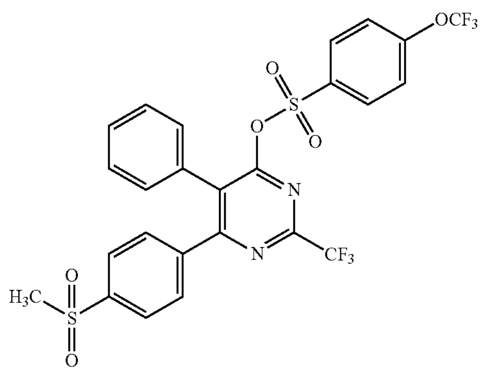 | $^1$H-NMR (CDCl$_3$) δ: 3.00 (s, 3H), 7.17-7.20 (d, 2H), 7.21-7.26 (dd, 3H), 7.40-7.43 (m, 2H), 7.81-7.80 (m, 4H), 7.84-7.87 (dd, 1H), 8.40-8.42 (dd, 1H); MS m/z: 603.51 (M$^+$ + 1). |
| | m.p: 165-168° C. | |
| 25 | 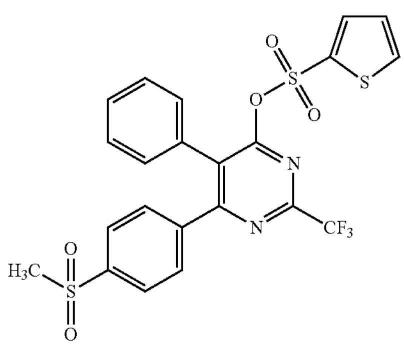 | $^1$H-NMR (CDCl$_3$) δ: 3.03 (s, 3H), 7.17-7.20 (d, 2H), 7.21-7.26 (dd, 3H), 7.81-7.83 (m, 4H), 7.84-7.86 (dd, 1H), 8.41-8.43 (dd, 1H); MS m/z: 603.51 (M$^+$ + 1). |
| | m.p: 184-188° C. | |
| 26 | 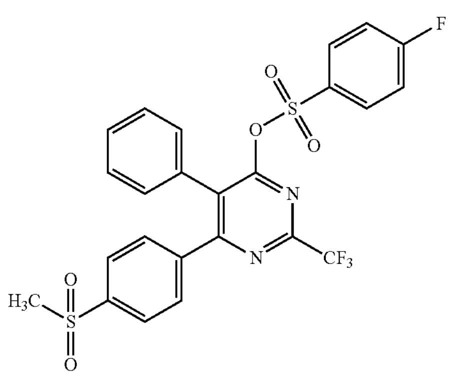 | $^1$H-NMR (CDCl$_3$) δ: 3.01 (s, 3H), 7.17-7.20 (d, 2H), 7.21-7.24 (dd, 3H), 7.40-7.43 (m, 2H), 7.81-7.83 (m, 4H), 7.84-7.86 (dd, 1H), 8.41-8.43 (dd, 1H); MS m/z: 603.51 (M$^+$ + 1). |
| | m.p: 193-195° C. | |

| Ex. | Structure | Analytical Data |
|---|---|---|
| 27 | 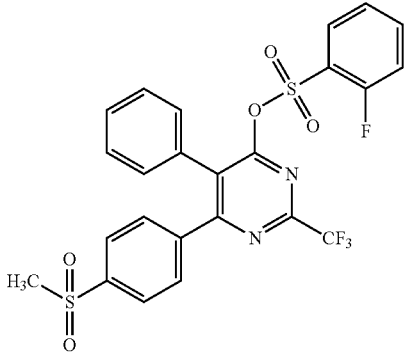 m.p: 200-204° C. | $^1$H-NMR (CDCl$_3$) δ: 3.01 (s, 3H), 7.17-7.20 (d, 2H), 7.21-7.24 (dd, 3H), 7.40-7.43 (m, 2H), 7.81-7.83 (m, 4H), 7.84-7.86 (dd, 1H), 8.41-8.43 (dd, 1H); MS m/z: 603.51 (M$^+$ + 1). |
| 28 | 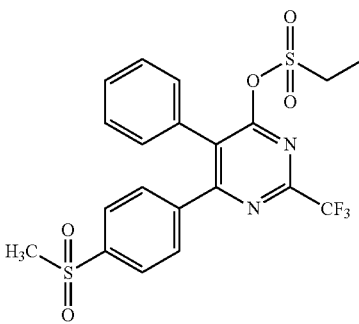 Sticky material | $^1$H-NMR (CDCl$_3$) δ: 0.88-0.89 (m, 2H), 1.25-1.28 (t, 2H), 1.33-1.38 (t, 2H), 2.85 (s, 6H), 2.97 (s, 3H), 7.04-7.74 (m, 9H); MS m/z: 544.59 (M$^+$ + 1). |

Example 29

Synthesis of 6-[4-(methylsulfonyl)phenyl]-5-phenyl-4-(N-benzyl-piperazin-1-yl)-2-(trifluoromethyl)pyrimidine

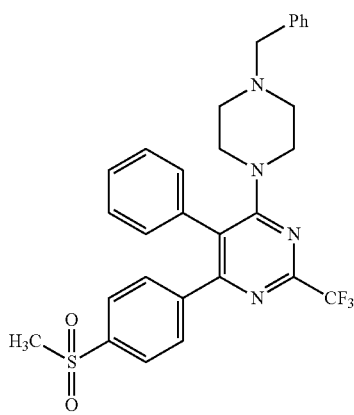 [SMILES: CS(=O)(=O)c1ccc(-c2nc(C(F)(F)F)nc(N3CCN(Cc4ccccc4)CC3)c2-c2ccccc2)cc1]

To a suspension of Pd$_2$(dba)$_3$ (0.443 g, 0.484 mmol) in toluene (50 ml) was added racemic-2,2'-bis(diphenyl phosphino)-1,1'-dinaphthyl (0.151 g, 0.242 mmol) at 37° C. under stirring. After 10 minutes of stirring the resulting solution was added to a suspension of N-benzyl piperazine (2.51 ml, 14.55 mmol), 4-chloro-6-[4-(methylsulfonyl)phenyl]-5-phenyl-2-(trifluoromethyl)pyrimidine (5 g, 12.12 mmol, prepared according to the procedure described in PCT/IB03/02879) and cesium carbonate (5.53 g, 16.9 mmol) in toluene (80 ml) under stirring. Subsequently the reaction mixture was refluxed for 6 hours and filtered. The solid obtained was washed thoroughly with ethyl acetate and the resultant organic layer was washed successively with water (3×100 ml), brine (200 ml) then dried over anhydrous sodium sulphate and evaporated to afford the title compound (5.5 g, yield 82.21%).

Preparation 2

Method A

Preparation of 6-[4-(methylsulfonyl)phenyl]-5-phenyl-4-piperazin-1-yl-2-(trifluoromethyl)pyrimidine

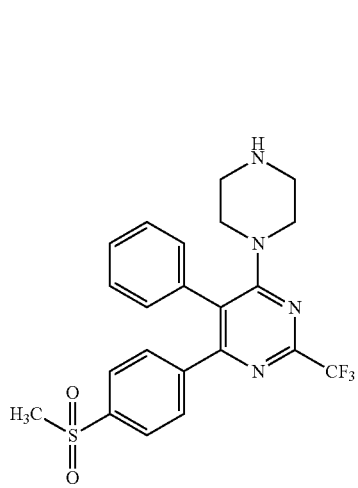 [SMILES: CS(=O)(=O)c1ccc(-c2nc(C(F)(F)F)nc(N3CCNCC3)c2-c2ccccc2)cc1]

To a solution of 6-[4-(methylsulfonyl)phenyl]-5-phenyl-4-(N-benzyl-piperazin-1-yl)-2-(trifluoromethyl)pyrimidine (5 g, 9 mmol) in dry dichloromethane (20 ml) was added diisopropyl ethylamine (2.5 ml, 18 mmol) under stirring at 0° C. 1-chloro-ethyl chloroformate (1.35 ml, 13.5 mmol) was later added to the above, under stirring and the stirring was further continued at 37° C. for 5 hours. Subsequently dichloromethane was evaporated upto dryness and methanol (20 ml) was added dropwise to the resulting mass, which was refluxed for 3 hours at 60° C. The reaction mixture was poured onto ice and filtered; the solid obtained was washed with hexane (100 ml) and diisopropyl ether (50 ml), to give the title compound (4 g, yield 95.9%).

Method B

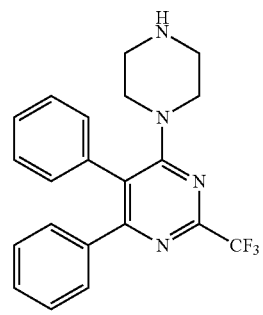 [SMILES: FC(F)(F)c1nc(-c2ccccc2)c(-c2ccccc2)c(N2CCNCC2)n1]

Piperazine (4.12 g, 47.8 mmol) was added to a solution of 4-chloro-5,6-diphenyl-2-trifluoromethylpyrimidine (4.0 g, 11.95 mmol) prepared according to the procedure described in the PCT/IB03/02879 in acetonitrile (30 ml) under stirring at 37° C. After 2 hours when TLC confirmed the completion of the reaction, the reaction mixture was poured onto ice and extracted with ethyl acetate (250 ml). The organic layer was dried over anhydrous sodium sulphate and evaporated to afford the title compound (3.5 g, yield 76.25%, purity by HPLC 100%); m.p: 160-162° C. $^1$H-NMR (DMSO-$d_6$) δ: 2.5 (s, 4H), 3.16 (t, 4H), 7.07-7.08 (m, 2H), 7.17-7.31 (m, 9H, 1H, $D_2O$ exchangeable); IR cm$^{-1}$ (KBr): 3304, 3058, and 1559; MS m/z: 385.2 (M$^+$+1).

The following compounds were prepared according to the procedure described for the preparation 2

| Ex. | Structure | Analytical Data |
|-----|-----------|-----------------|
| 30 | ![structure] m.p: >285° C. | $^1$H-NMR (DMSO-$d_6$) δ: 2.98 (s, 4H), 3.35-3.42 (m, 4H), 7.36-7.38 (m, 1H), 7.44-7.48 (m, 2H), 7.52-7.56 (m, 1H), 7.77-7.79 (m, 2H), 9.24 (s, 2H, $D_2O$ exchangeable); MS m/z: 482.1 (M$^+$ + 1). |

-continued

| Ex. | Structure | Analytical Data |
|---|---|---|
| 31 | m.p: >285° C. | $^1$H-NMR (DMSO-$d_6$) δ: 3.01(s, 4H), 3.42 (s, 4H), 7.1-7.11 (m, 2H), 7.26-7.32 (m, 3H), 7.38-7.41 (m, 2H), 7.75-7.77 (s, 3H), 9.0 (s, 2H, D$_2$O exchangeable); MS m/z: 482.1 (M$^+$ + 1). |
| 32 | m.p: 245-247° C. | $^1$H-NMR (DMSO-$d_6$) δ: 2.09 (s, 4H), 2.7 (s, 3H), 3.15 (s, 3H), 3.22-3.32 (d, 4H), 7.35-7.37 (m, 2H), 7.51-7.55 (m, 3H), 7.62-7.64 (m, 1H), 7.70-7.79 (m, 2H); MS m/z: 556.1 (M$^+$ + 1). |
| 33 | m.p: 230-235° C. | $^1$H-NMR (CDCl$_3$) δ: 2.15 (s, 3H), 3.02 (s, 4H), 3.47 (s, 4H), 4.5 (s, 1H, D$_2$O exchangeable), 7.26 (s, 2H), 7.32-7.36 (m, 3H), 7.47-7.51 (m, 2H), 7.77-7.79 (m, 4H); MS m/z: 542.1 (M$^+$ + 1). |

| Ex. | Structure | Analytical Data |
|---|---|---|
| 34 | 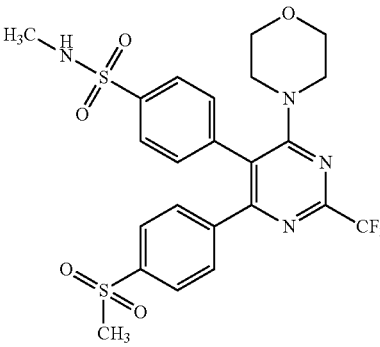 m.p: 175-177° C. | $^1$H-NMR (CDCl$_3$) δ: 2.4-2.41 (d, 3H), 3.0 (s, 3H), 3.34-3.37 (m, 4H), 3.58-3.6 (m, 4H), 4.1-4.3 (m, 1H, D$_2$O exchangeable), 7.26-7.31 (m, 2H), 7.46 (s, 2H), 7.54-7.58 (m, 1H), 7.78-7.8 (m, 3H); IR cm$^{-1}$ (KBr): 3205, 2886, 2856, 1693 and 1557; MS m/z: 557.1 (M$^+$). |
| 35 | 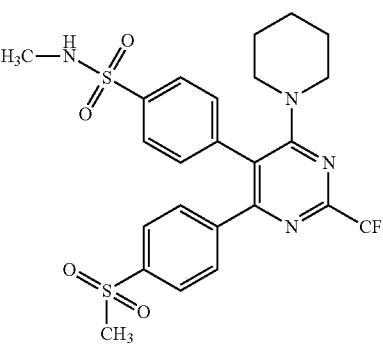 m.p: 204-206° C. | $^1$H-NMR (CDCl$_3$) δ: 1.19-1.22 (m, 4H), 1.56-1.62 (m, 2H), 2.39-2.41 (d, 3H), 3.0 (s, 3H), 3.29-3.31 (m, 4H), 4.13-4.15 (m, 1H, D$_2$O exchangeable), 7.26-7.29 (m, 2H), 7.442-7.446 (m, 2H), 7.51-7.54 (m, 1H), 7.74-7.78 (m, 3H); IR cm$^{-1}$ (KBr): 3280, 2938, 2851, 1561 and 1525; MS m/z: 555 (M+). |

Preparation 3

Preparation of 6-[4-(methylsulfonyl)phenyl]-5-phenyl-4-[4-(2-thienyl carbonyl)piperazin-1-yl]-2-(trifluoromethyl)pyrimidine

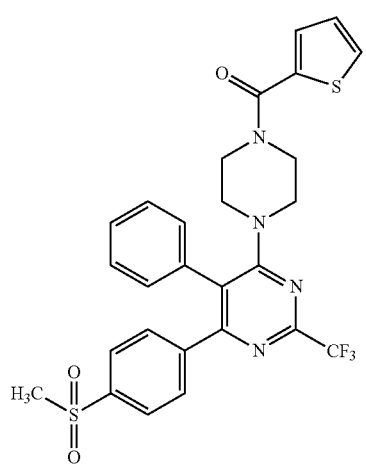 [SMILES: CS(=O)(=O)c1ccc(-c2nc(C(F)(F)F)nc(N3CCN(C(=O)c4cccs4)CC3)c2-c2ccccc2)cc1]

To a solution of 6-[4-(methylsulfonyl)phenyl]-5-phenyl-4-piperazin-1-yl-2-(trifluoromethyl)pyrimidine (0.2 g, 0.43 mmol, prepared according to the procedure described in preparation 2) in DMF (20 ml) was added thiophene-2-carboxylic acid (0.149 g, 0.78 mmol) under stirring at 37° C. and then after 10 minutes EDCI (0.149 g, 0.78 mmol), and HOBt (0.023 g, 0.173 mmol) were added. Further TEA (0.179 ml, 2.9 mmol) was added to the resultant clear solution and it was stirred for 18 hours. Subsequently the reaction mixture was diluted with ethyl acetate (50 ml) and the organic layer was washed successively with water, 10% sodium bi carbonate solution (100 ml) and brine (100 ml) respectively and dried over anhydrous sodium sulphate. Evaporation of the solvent and purification by column chromatography (0.4% MeOH: DCM) gave the title compound (0.12 g, yield 48.6%); m.p. 189-194° C. $^1$H-NMR (CDCl$_3$) δ: 2.98 (s, 3H), 3.4-3.41 (t, 4H), 3.66-3.68 (t, 4H), 7.02-7.77 (m, 12H); MS m/z: 573.2 (M$^+$+1).

The following compounds were prepared according to the procedure described for the preparation 3

| Ex. | Structure | Analytical data |
|---|---|---|
| 36 | 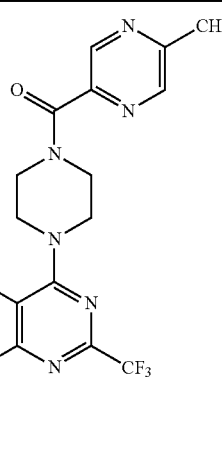<br>m.p: 163-168° C. | $^1$H-NMR (CDCl$_3$) δ: 2.67 (s, 3H), 2.98 (s, 3H), 3.43-3.45 (t, 4H), 3.63-3.64 (t, 2H), 3.68-3.7 (t, 2H), 7.11-8.84 (m, 11H); MS m/z: 583.2 (M$^+$ + 1). |
| 37 | 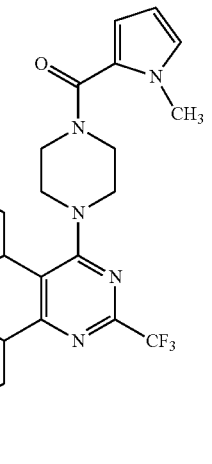<br>m.p: 235-238° C. | $^1$H-NMR (CDCl$_3$) δ: 2.98 (s, 3H), 3.37-3.39 (t, 4H), 3.63-3.67 (t, 4H), 3.75 (s, 3H), 6.95-7.77 (m, 11H); MS m/z: 570.63 (M$^+$ + 1). |
| 38 | 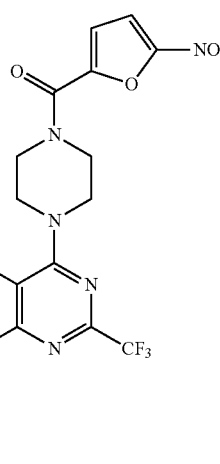<br>m.p: 158-161° C. | $^1$H-NMR (CDCl$_3$) δ: 2.99 (s, 3H), 3.49-3.51 (t, 4H), 3.82-3.83 (t, 4H), 7.13-7.18 (m, 3H), 7.26-7.34 (m, 6H), 7.76-7.78 (dd, 2H); MS m/z: 602.1 (M$^+$ + 1). |

| Ex. | Structure | Analytical data |
|---|---|---|
| 39 | 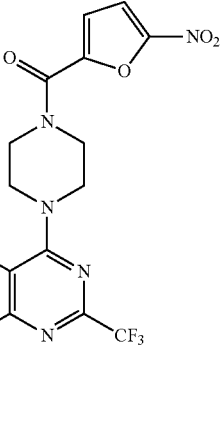 m.p: 114-118° C. | $^1$H-NMR (CDCl$_3$) δ: 2.43-2.44 (d, 3H), 3.01 (s, 3H), 3.47 (s, 4H), 3.71-3.85 (d, 4H), 4.39 (s, 1H, D$_2$O exchangeable), 7.19 (s, 1H), 7.26-7.33 (m, 3H), 7.43-7.45 (m, 1H), 7.54-7.59 (m, 2H), 7.79-7.81 (d, 3H); MS m/z: 695.1 (M$^+$ + 1). |
| 40 | 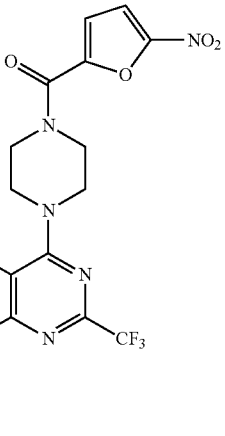 m.p: 250-253° C. | $^1$H-NMR (DMSO-d$_6$) δ: 3.35 (s, 4H), 3.54-3.67 (d, 4H), 7.06-7.16 (m, 5H), 7.23-7.24 (d, 1H), 7.35-7.73 (m, 3H), 7.74-7.78 (m, 3H); MS m/z: 621.2 (M$^+$ + 1). |
| 41 | 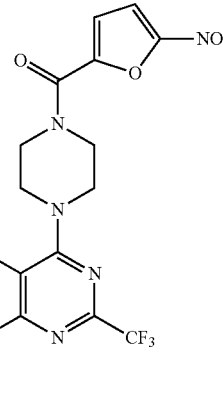 m.p: 225-227° C. | $^1$H-NMR (DMSO-d$_6$) δ: 3.36 (s, 4H), 3.33-3.67 (d, 4H), 7.13-7.21 (m, 4H), 7.26-7.4 (m, 4H), 7.72-7.74 (d, 4H); MS m/z: 621.2 (M$^+$ + 1). |

| Ex. | Structure | Analytical data |
|---|---|---|
| 42 | 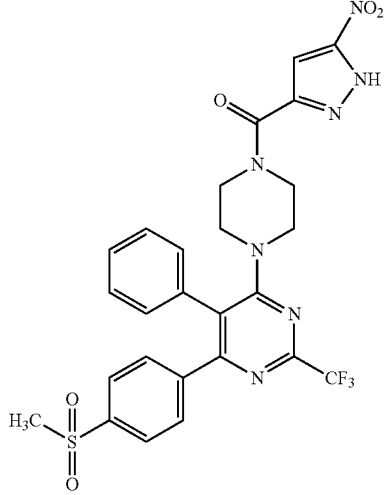<br>m.p: 127-132° C. | $^1$H-NMR (CDCl$_3$) δ: 2.99 (s, 3H), 3.48-3.51 (t, 4H), 3.87-3.88 (t, 4H), 7.12-7.13 (m, 1H), 7.14-7.15 (t, 2H), 7.26-7.28 (m, 5H), 7.76-7.78 (dd, 2H); MS m/z: 602.3 (M$^+$ + 1). |
| 43 | 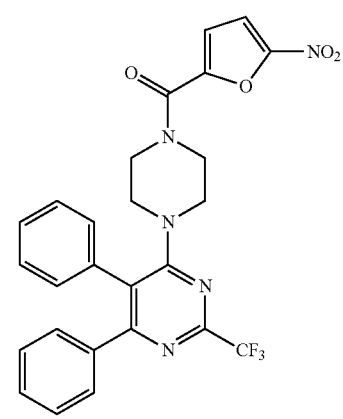<br>m.p: 230-233° C. | $^1$H-NMR (CDCl$_3$) δ: 3.37-3.45 (d, 4H), 3.63-3.81 (d, 4H), 7.13-7.26 (m, 8H), 7.30-7.33 (m, 4H); MS m/z: 524.1 (M$^+$ + 1). |
| 44 | 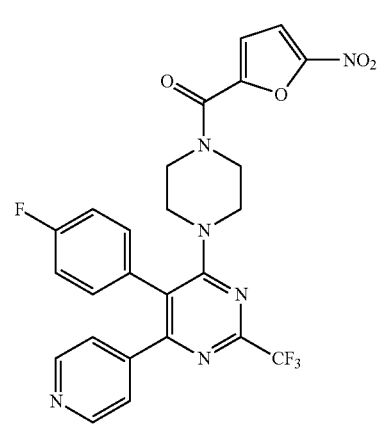<br>m.p: 185-187° C. | $^1$H-NMR (CDCl$_3$) δ: 3.43-3.51 (d, 4H), 3.68-3.87 (d, 4H), 7.02-7.15 (m, 7H), 7.34-7.35 (d, 1H), 8.49-8.5 (d, 2H); IR (KBr) cm$^{-1}$: 3428 and 1633; MS m/z: 543.1 (M$^+$ + 1). |

Example 45

Synthesis of 6-[4-(methylsulfonyl)phenyl]-5-phenyl-4-[4-(1,3-thiazol-2-yl methyl)piperazin-1-yl]-2-(trifluoromethyl)pyrimidine

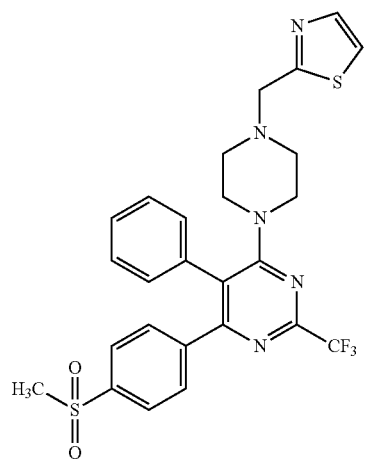 [SMILES: CS(=O)(=O)c1ccc(-c2nc(C(F)(F)F)nc(N3CCN(Cc4nccs4)CC3)c2-c2ccccc2)cc1]

To a solution of 6-[4-(methylsulfonyl)phenyl]-5-phenyl-4-piperazin-1-yl-2-(trifluoromethyl)pyrimidine (0.2 g, 0.43 mmol, prepared according to the procedure described in preparation 2) in dichloroethane (25 ml) was added thiazole-2-carboxaldehyde (0.144 g, 1.3 mmol) under stirring at 37° C. After five minutes, sodium triacetoxy borohydride (0.364 g, 1.72 mmol) was added to reaction mixture and then after 10 minutes, acetic acid (0.1 ml) was added to it. The reaction mixture was stirred for 36 hours under the same conditions. Subsequently the reaction mixture was treated with ethyl acetate:water (1:1, 100 ml) and extracted with ethyl acetate (3×50 ml). The organic layer was washed with brine (100 ml) and dried over anhydrous sodium sulphate. The solid obtained upon evaporation was purified by column chromatography using methanol: dichloromethane (0.5:99.5) as an eluent to afford the title compound (0.11 g, yield 45.6%). $^1$H-NMR (CDCl$_3$) δ: 0.88-0.89 (m, 2H), 1.25-1.28 (t, 2H), 1.33-1.38 (t, 2H), 2.85 (s, 6H), 2.97 (s, 3H), 7.04-7.74 (m, 9H); MS m/z: 544.59 (M$^+$+1).

The following compounds were prepared according to the procedure described for example 45

| Ex. | Structure | Analytical Data |
|---|---|---|
| 46 | (see structure) | $^1$H-NMR (CDCl$_3$) δ: 2.50-2.53 (t, 4H), 2.98 (s, 3H), 3.44-3.46 (t, 4H), 3.88 (s, 2H), 7.14-7.78 (m, 13H); MS m/z: 554.3 (M$^+$ + 1). m.p: 228-232° C. |
| 47 | (see structure) | $^1$H-NMR (CDCl$_3$) δ: 2.51-2.52 (t, 4H), 2.99 (s, 3H), 3.44-3.46 (t, 4H), 3.88 (s, 2H), 7.10-7.81 (m, 11H); MS m/z: 604.7 (M$^+$ + 1). m.p: 168-174° C. |

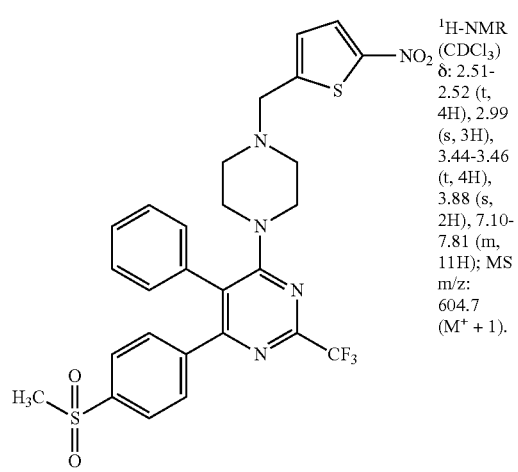

Example 48

Synthesis of 4,5-diphenyl-6-(4-pyridin-2-yl-piperazin-1-yl)-2-(trifluoromethyl)pyrimidine

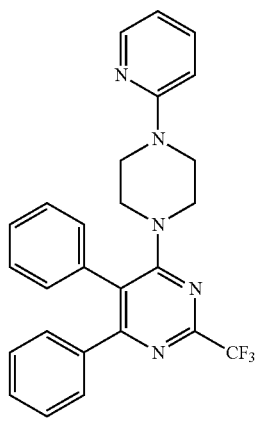 [SMILES: FC(F)(F)c1nc(-c2ccccc2)c(-c2ccccc2)c(N2CCN(c3ccccn3)CC2)n1]

To a solution of 4-chloro-5,6-diphenyl-2-(trifluoromethyl) pyrimidine (0.5 g, 1.49 mmol, prepared according to the procedure described in PCT/IB03/02879) in DMF (5 ml) was added 1-pyridin-2-yl piperazine (0.107 g, 0.66 mmol) and anhydrous potassium carbonate (0.2 g) under stirring at 28° C. The reaction mixture was stirred for 4 hours and when TLC confirmed the completion, it was poured onto ice. The solid thus obtained was filtered and washed with water (20 ml). The above solid was then dissolved in dichloromethane (50 ml) and dried over anhydrous sodium sulphate. Evaporation of the solvent afforded the title compound (0.48 g, yield 69.66%, purity by HPLC 99.8%). m.p. 165-167° C. $^1$H-NMR (CDCl$_3$) δ: 3.43 (s, 8H), 6.58-6.64 (m, 2H), 7.14-7.21 (m, 7H), 7.26-7.29 (m, 3H), 7.45-7.49 (t, 1H), 8.14-8.15 (d, 1H); IR cm$^{-1}$ (KBr): 3436, 2839, 1591 and 1557; MS m/z: 462.1 (M$^+$+1).

The following compound was prepared as per the above-mentioned procedure

| Ex. | Structure | Analytical Data |
|---|---|---|
| 49 | (structure shown) m.p.: 229-233° C. | $^1$H-NMR (DMSO-d$_6$) δ: 3.18-3.21 (d, 3H), 3.17-3.4(d, 8H), 6.63-6.66 (t, 1H), 6.76-6.78 (d, 1H), 7.27-7.28 (d, 2H), 7.35-7.37 (d, 5H), 7.49-7.53 (t, 1H), 8.07-8.08 (d, 1H); MS m/z: 540.4 (M$^+$ + 1). |

Preparation 4

Preparation of 3-[4-(4-fluorophenyl)-6-piperazin-1-yl-2-(trifluoromethyl)pyrimidin-5-yl]benzenesulfonamide hydrochloride [Hydrochloride of the example-50] and 4-[4-(4-fluorophenyl)-6-piperazin-1-yl-2-(trifluoromethyl)pyrimidin-5-yl]benzenesulfonamide hydrochloride [example-30]

Step 1

Preparation of 3-[4-chloro-6-(4-fluorophenyl)-2-(trifluoromethyl)pyrimidin-5-yl]benzenesulfonyl chloride and 4-[4-chloro-6-(4-fluorophenyl)-2-(trifluoromethyl)pyrimidin-5-yl]benzenesulfonyl chloride

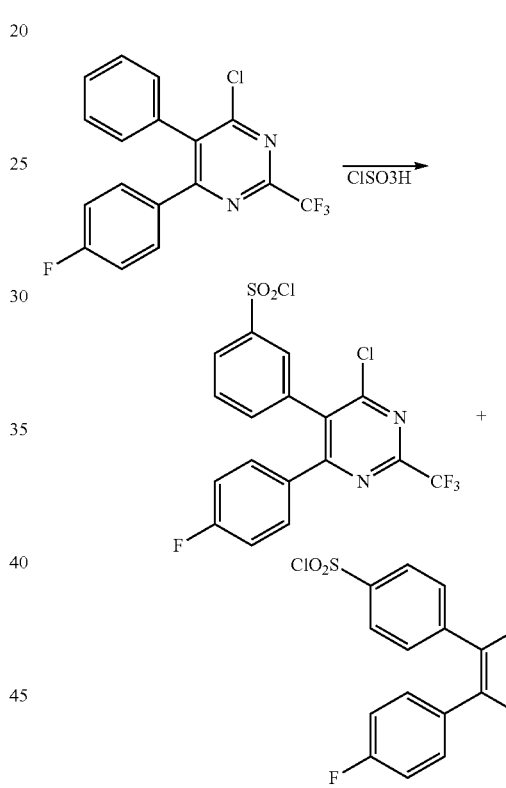

4-Chloro-6-(4-fluorophenyl)-5-phenyl-2-(trifluoromethyl)pyrimidine (30 g, 0.085 mol) was added to cold chlorosulfonic acid (200 ml, 3.0 mol) and the reaction mixture was stirred for 48 hours at room temperature. Subsequently it was poured into crushed ice (~3 kg) and was extracted with dichloromethane (1000 mL). The organic layer was washed with sodium bicarbonate (7%, 1000 mL) and with brine solution (500 mL). The crude material obtained after evaporation was recrystallised from hexane-EtOAc to obtain the pure para and meta substituted sulphonyl chlorides. However, the crude product containing mixture of meta and para isomers was used as such in the examples mentioned below unless otherwise mentioned.

3-[4-Chloro-6-(4-fluorophenyl)-2-(trifluoromethyl)pyrimidin-5-yl]benzene sulfonylchloride $^1$H-NMR (CDCl$_3$) δ: 6.97-7.01 (m, 2H), 7.32-7.36 (m, 2H), 7.63-7.65 (d, 1H), 7.71-7.74 (t, 1H), 7.90-7.91 (s, 1H), 8.10-8.12 (d, 1H).

4-[4-Chloro-6-(4-fluorophenyl)-2-(trifluoromethyl)pyrimidin-5-yl]benzene sulfonyl chloride ¹H-NMR (CDCl₃) δ: 6.97-7.01 (m, 2H), 7.34-7.38 (m, 2H), 7.50-7.53 (d, 2H), 8.11-8.13 (d, 2H).

Step 2a

Preparation of 3-[4-chloro-6-(4-fluorophenyl)-2-(trifluoromethyl)pyrimidin-5-yl]benzenesulfonamide

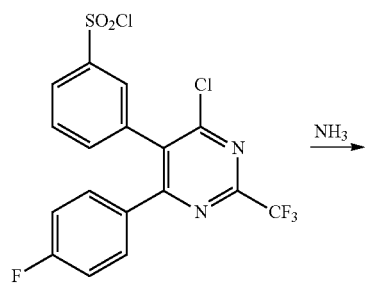

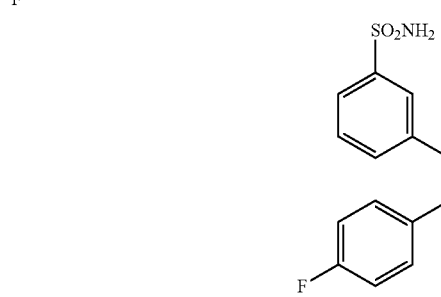

The sulphonyl chloride group is converted into the sulphonamido group by treatment with ammonia gas under cold conditions (0-5° C.) by dissolving the substance in dichloromethane. Subsequently the reaction mixture was washed with water (100 mL) and then with brine solution; evaporation of the solvent furnished the title compound. ¹H-NMR (DMSO-d₆) δ: 7.14-7.18 (m, 2H), 7.38-7.42 (m, 2H), 7.48 (brs, 2H, D₂O exchangeable), 7.56 (d, 1H), 7.62-7.66 (t, 1H), 7.86 (s, 1H), 7.88 (d, 1H); MS m/z: 433 (M⁺+1).

Step 2b

Preparation of 4-[4-chloro-6-(4-fluorophenyl)-2-(trifluoromethyl)pyrimidin-5-yl]benzenesulfonamide

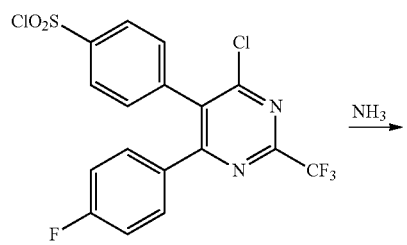

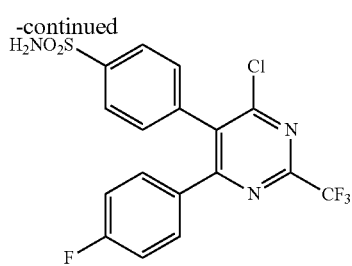

Similarly 4-[6-chloro-5-phenyl-2-(trifluoromethyl)pyrimidin-4-yl]benzene sulfonamide was prepared from 4-chloro-5,6-diphenyl-2-(trifluoromethyl)pyrimidine which in turn was prepared according to the procedure described in PCT/IB03/02879). ¹H-NMR (DMSO-d₆) δ: 7.16-7.21 (m, 2H), 7.38-7.41 (m, 2H), 7.48 (brs, 2H, D₂O exchangeable), 7.57 (d, 2H), 7.86 (d, 2H); MS m/z: 432 (M⁺).

Example 50

Synthesis of 3-[4-(4-fluorophenyl)-6-piperazin-1-yl-2-(trifluoromethyl)pyrimidin-5-yl]benzenesulfonamide

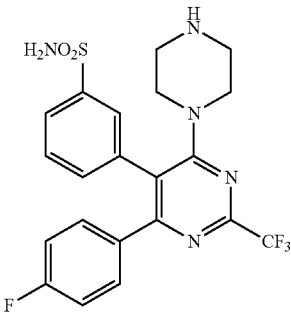 [SMILES: NS(=O)(=O)c1cccc(-c2c(-c3ccc(F)cc3)nc(C(F)(F)F)nc2N2CCNCC2)c1]

The solution of 3-[4-chloro-6-(4-fluorophenyl)-2-(trifluoromethyl)pyrimidin-5-yl]benzenesulfonamide (0.1 g, 0.24 mmol, prepared according to the procedure described above in preparation 4, Step 2a), in acetonitrile (2 ml) was treated with piperazine (0.104 g, 1.203 mmol) and the reaction mixture was stirred overnight at room temperature. Subsequently the reaction mixture was poured into ice-cold water and was extracted with ethylacetate (25 ml). The organic layer was washed with water, brine solution and then evaporated to obtain the title compound. ¹H-NMR (DMSO-d₆) δ: 2.58 (s, 4H), 3.19 (s, 4H), 7.03-7.14 (m, 4H), 7.32 (d, 1H), 7.41 (brs, D₂O exchangeable, 2H), 7.46-7.50 (t, 1H), 7.72 (s, 1H), 7.73 (d, 1H); MS m/z: 482.1 (M⁺+1).

The following compounds were prepared according to the above-mentioned procedure.

| # | Structure | Data |
|---|---|---|
| 51 | (sulfamoylphenyl-piperazinyl-phenyl-CF₃-pyrimidine) | ¹H-NMR (DMSO-d₆) δ: 2.52-2.54 (m, 4H), 3.18 (m, 4H), 7.04 (d, 1H), 7.26-7.33 (m, 2H), 7.41-7.48 (m, 4H), 7.73 (d, 1H), 7.75 (d, 1H), 7.81 (s, 1H); MS m/z: 464.1 (M⁺). |
| 52 | (bis-sulfamoylphenyl-piperazinyl-CF₃-pyrimidine) | ¹H-NMR (CDCl₃) δ: 2.56 (m, 4H), 3.18 (m, 4H), 7.02-7.09 (m, 1H), 7.31-7.33 (m, 2H), 7.40-7.48 (m, 5H), 7.72-7.75 (d, 3H), 7.81 (s, 1H); MS m/z: 543.0 (M⁺ + 1). |
| 53 | (sulfamoyl-pyridyl-piperazinyl-fluorophenyl-CF₃-pyrimidine) | ¹H-NMR (CDCl₃) δ: 3.44 (s, 8H), 6.61-6.66 (m, 2H), 6.90 (d, 2H), 7.09 (d, 2H), 7.31-7.35 (m, 2H), 7.47-7.51 (m, 2H), 7.76 (s, 1H), 7.85-7.90 (m, 1H), 8.17 (d, 2H); MS m/z: 559.1 (M⁺ + 1). |
| 54 | (sulfamoyl-pyrimidinyl-piperazinyl-fluorophenyl-CF₃-pyrimidine) | ¹H-NMR (CDCl₃) δ: 3.38-3.41 (m, 4H), 3.71-3.74 (m, 4H), 6.61-6.66 (m, 1H), 6.90 (d, 2H), 7.09 (d, 2H), 7.31-7.35 (m, 1H), 7.47-7.51 (m, 1H), 7.76 (s, 1H), 7.85-7.90 (m, 1H), 8.29 (d, 2H); MS m/z: 560.1 (M⁺ + 1). |
| 55 | (sulfamoylphenyl-thiazolidinyl-phenyl-CF₃-pyrimidine) | ¹H-NMR (CDCl₃) δ: 2.94-2.97 (m, 2H), 3.60-3.63 (m, 2H), 4.25 (s, 2H), 7.06-7.08 (m, 2H), 7.18-7.21 (m, 2H), 7.41-7.47 (m, 3H), 7.61 (s, 1H), 7.82 (d, 1H); MS m/z: 467.0 (M⁺ + 1). |
| 56 | (bis-sulfamoylphenyl-hydroxycyclohexylamino-CF₃-pyrimidine) | ¹H-NMR (DMSO-d₆) δ: 1.20-1.25 (m, 4H), 1.42-1.49 (m, 4H), 3.61 (m, 1H), 4.09 (m, 1H), 4.77 (br, 1H, D₂O exchangeable), 5.14 (br, 1H, D₂O exchangeable), 7.51-7.56 (m, 2H), 7.75-7.77 (d, 2H), 7.88-7.95 (m, 4H); MS m/z: 572.0 (M⁺ + 1). |
| 57 | (sulfamoylphenyl-piperazinyl-pyrimidinyl-phenyl-CF₃-pyrimidine) | ¹H-NMR (CDCl₃) δ: 3.36-3.42 (m, 4H), 3.72-3.81 (m, 4H), 6.53 (d, 1H), 7.08 (d, 2H), 7.19-7.25 (m, 2H), 7.34 (d, 1H), 7.40 (d, 1H), 7.46 (d, 2H), 7.68 (s, 1H), 7.82-7.85 (t, 1H), 8.28-8.31 (m, 2H); MS m/z: 541.8 (M⁺). |
| 58 | (sulfamoylphenyl-piperazinyl-pyridyl-phenyl-CF₃-pyrimidine) | ¹H-NMR (CDCl₃) δ: 3.45 (m, 8H), 6.62-6.64 (m, 1H), 6.75 (d, 1H), 7.01 (d, 2H), 7.20-7.26 (m, 3H), 7.31-7.33 (m, 1H), 7.40 (br s, 2H), 7.48-7.53 (m, 2H), 7.74 (d, 1H), 7.78 (s, 1H), 8.05 (d, 1H); MS m/z: 540.9 (M⁺). |

| | | |
|---|---|---|
| 59 | 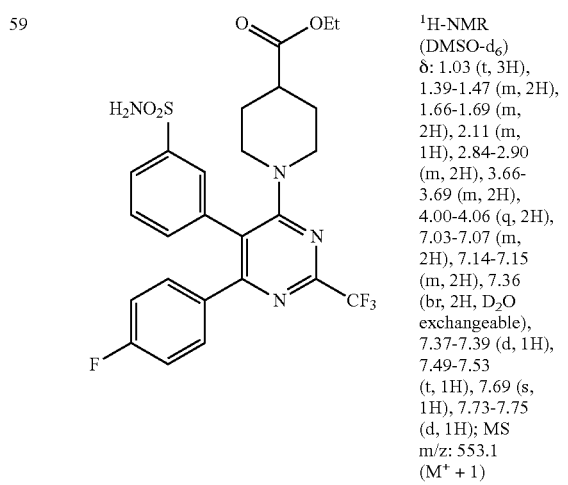 | ¹H-NMR (DMSO-d₆) δ: 1.03 (t, 3H), 1.39-1.47 (m, 2H), 1.66-1.69 (m, 2H), 2.11 (m, 1H), 2.84-2.90 (m, 2H), 3.66-3.69 (m, 2H), 4.00-4.06 (q, 2H), 7.03-7.07 (m, 2H), 7.14-7.15 (m, 2H), 7.36 (br, 2H, D₂O exchangeable), 7.37-7.39 (d, 1H), 7.49-7.53 (t, 1H), 7.69 (s, 1H), 7.73-7.75 (d, 1H); MS m/z: 553.1 (M⁺ + 1) |
| 60 | 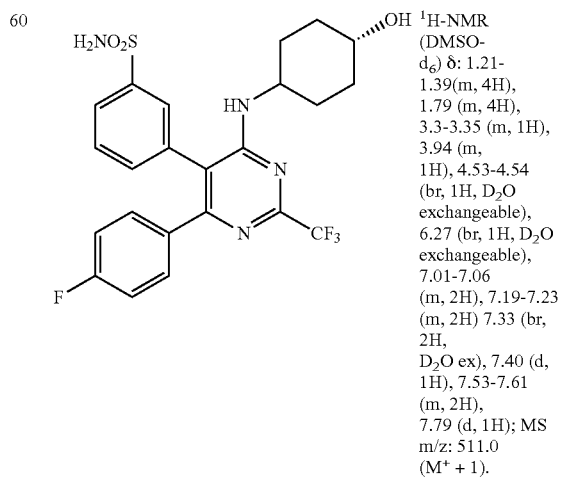 | ¹H-NMR (DMSO-d₆) δ: 1.21-1.39(m, 4H), 1.79 (m, 4H), 3.3-3.35 (m, 1H), 3.94 (m, 1H), 4.53-4.54 (br, 1H, D₂O exchangeable), 6.27 (br, 1H, D₂O exchangeable), 7.01-7.06 (m, 2H), 7.19-7.23 (m, 2H) 7.33 (br, 2H, D₂O ex), 7.40 (d, 1H), 7.53-7.61 (m, 2H), 7.79 (d, 1H); MS m/z: 511.0 (M⁺ + 1). |
| 61 | 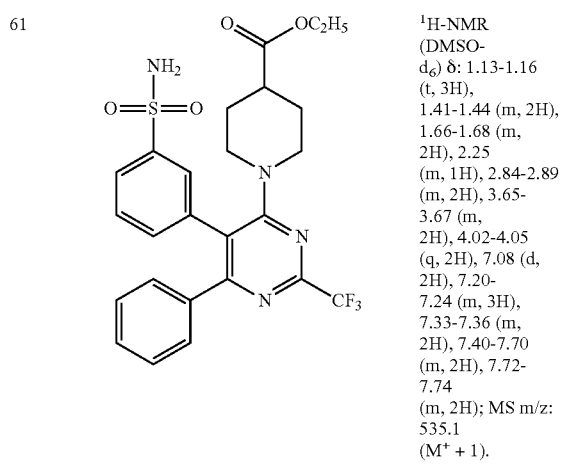 | ¹H-NMR (DMSO-d₆) δ: 1.13-1.16 (t, 3H), 1.41-1.44 (m, 2H), 1.66-1.68 (m, 2H), 2.25 (m, 1H), 2.84-2.89 (m, 2H), 3.65-3.67 (m, 2H), 4.02-4.05 (q, 2H), 7.08 (d, 2H), 7.20-7.24 (m, 3H), 7.33-7.36 (m, 2H), 7.40-7.70 (m, 2H), 7.72-7.74 (m, 2H); MS m/z: 535.1 (M⁺ + 1). |
| 62 | 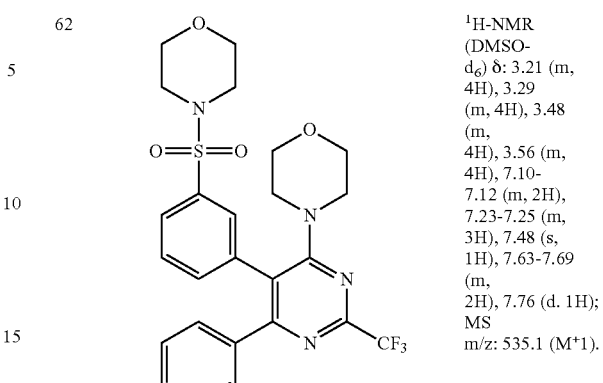 | ¹H-NMR (DMSO-d₆) δ: 3.21 (m, 4H), 3.29 (m, 4H), 3.48 (m, 4H), 3.56 (m, 4H), 7.10-7.12 (m, 2H), 7.23-7.25 (m, 3H), 7.48 (s, 1H), 7.63-7.69 (m, 2H), 7.76 (d, 1H); MS m/z: 535.1 (M⁺1). |
| 63 | 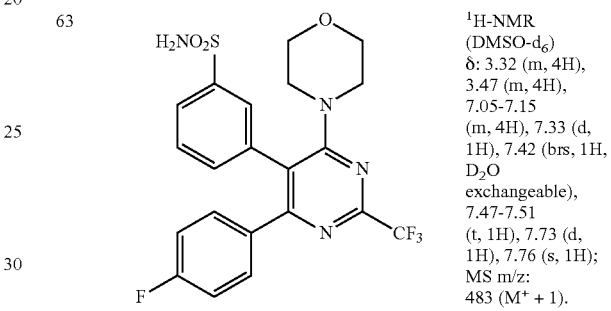 | ¹H-NMR (DMSO-d₆) δ: 3.32 (m, 4H), 3.47 (m, 4H), 7.05-7.15 (m, 4H), 7.33 (d, 1H), 7.42 (brs, 1H, D₂O exchangeable), 7.47-7.51 (t, 1H), 7.73 (d, 1H), 7.76 (s, 1H); MS m/z: 483 (M⁺ + 1). |
| 64 | 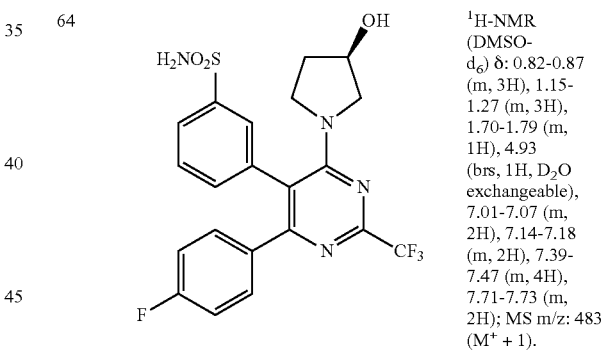 | ¹H-NMR (DMSO-d₆) δ: 0.82-0.87 (m, 3H), 1.15-1.27 (m, 3H), 1.70-1.79 (m, 1H), 4.93 (brs, 1H, D₂O exchangeable), 7.01-7.07 (m, 2H), 7.14-7.18 (m, 2H), 7.39-7.47 (m, 4H), 7.71-7.73 (m, 2H); MS m/z: 483 (M⁺ + 1). |
| 65 | 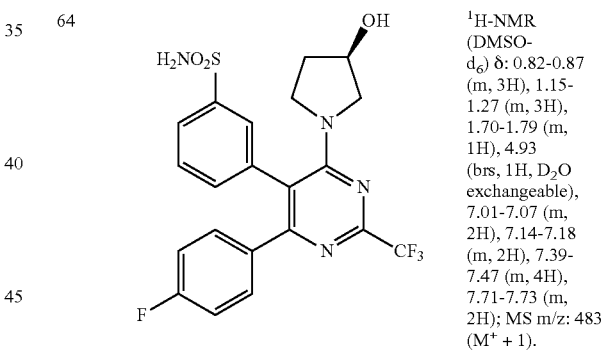 | ¹H-NMR (DMSO-d₆) δ: 1.17-1.27 (t, 3H), 1.86-1.89 (m, 1H), 2.08-2.14 (m, 2H), 2.66-2.68 (m, 1H), 4.13 (q, 2H), 4.68-4.70 (m, 1H), 5.09 (br, 1H, D₂O exchangeable), 7.03-7.09 (m, 2H), 7.18-7.21 (m, 2H), 7.25-7.28 (br, 2H, D₂O exchangeable), 7.37-7.45 (m, 2H), 7.75-7.77 (m, 2H); MS m/z: 555.1 (M⁺ + 1). |

| 66 | 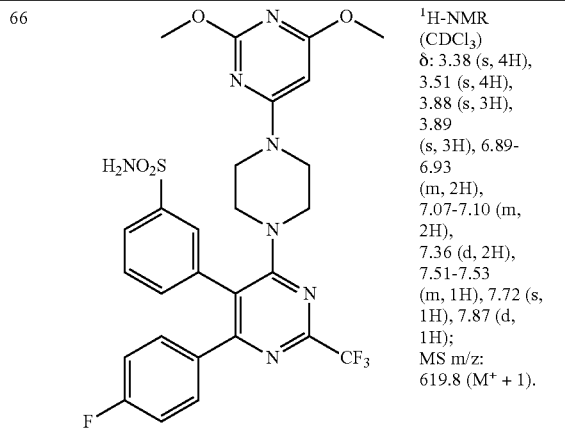 | ¹H-NMR (CDCl₃) δ: 3.38 (s, 4H), 3.51 (s, 4H), 3.88 (s, 3H), 3.89 (s, 3H), 6.89-6.93 (m, 2H), 7.07-7.10 (m, 2H), 7.36 (d, 2H), 7.51-7.53 (m, 1H), 7.72 (s, 1H), 7.87 (d, 1H); MS m/z: 619.8 (M⁺ + 1). |
|---|---|---|
| 67 | 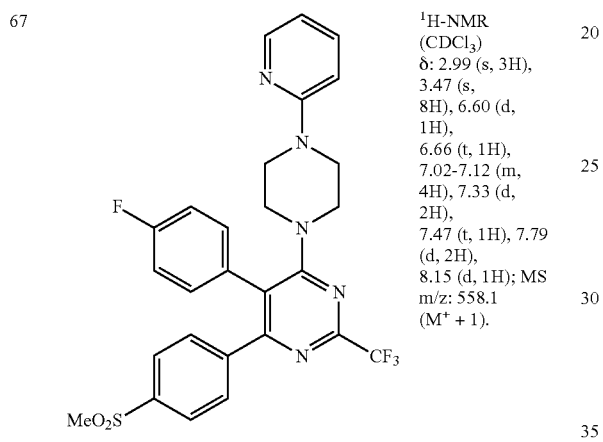 | ¹H-NMR (CDCl₃) δ: 2.99 (s, 3H), 3.47 (s, 8H), 6.60 (d, 1H), 6.66 (t, 1H), 7.02-7.12 (m, 4H), 7.33 (d, 2H), 7.47 (t, 1H), 7.79 (d, 2H), 8.15 (d, 1H); MS m/z: 558.1 (M⁺ + 1). |
| 68 | 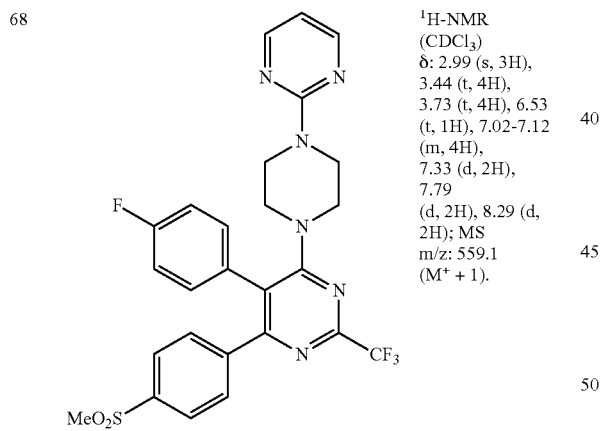 | ¹H-NMR (CDCl₃) δ: 2.99 (s, 3H), 3.44 (t, 4H), 3.73 (t, 4H), 6.53 (t, 1H), 7.02-7.12 (m, 4H), 7.33 (d, 2H), 7.79 (d, 2H), 8.29 (d, 2H); MS m/z: 559.1 (M⁺ + 1). |
| 69 | 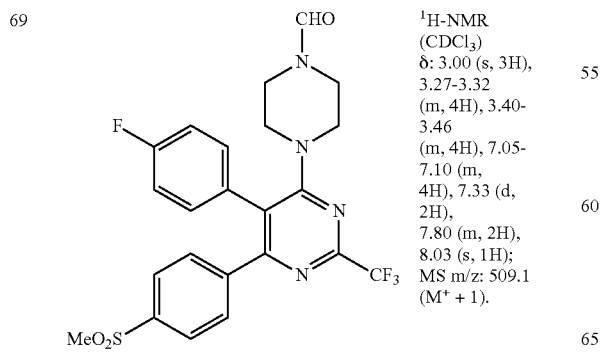 | ¹H-NMR (CDCl₃) δ: 3.00 (s, 3H), 3.27-3.32 (m, 4H), 3.40-3.46 (m, 4H), 7.05-7.10 (m, 4H), 7.33 (d, 2H), 7.80 (m, 2H), 8.03 (s, 1H); MS m/z: 509.1 (M⁺ + 1). |
| 70 | 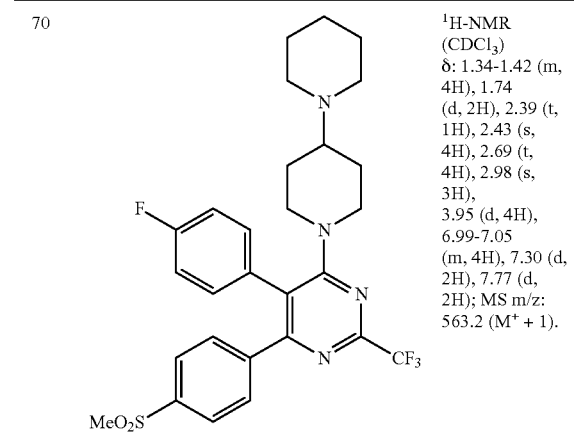 | ¹H-NMR (CDCl₃) δ: 1.34-1.42 (m, 4H), 1.74 (d, 2H), 2.39 (t, 1H), 2.43 (s, 4H), 2.69 (t, 4H), 2.98 (s, 3H), 3.95 (d, 4H), 6.99-7.05 (m, 4H), 7.30 (d, 2H), 7.77 (d, 2H); MS m/z: 563.2 (M⁺ + 1). |
| 71 | 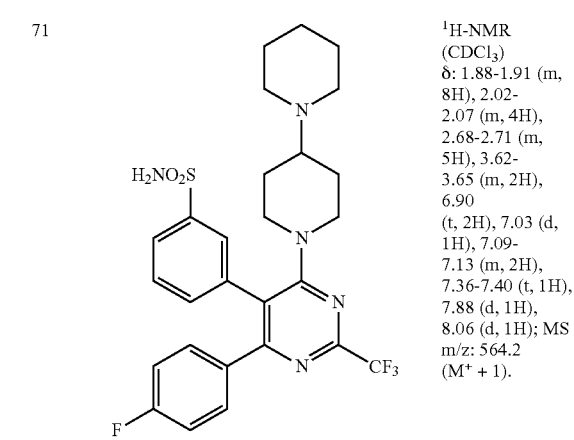 | ¹H-NMR (CDCl₃) δ: 1.88-1.91 (m, 8H), 2.02-2.07 (m, 4H), 2.68-2.71 (m, 5H), 3.62-3.65 (m, 2H), 6.90 (t, 2H), 7.03 (d, 1H), 7.09-7.13 (m, 2H), 7.36-7.40 (t, 1H), 7.88 (d, 1H), 8.06 (d, 1H); MS m/z: 564.2 (M⁺ + 1). |
| 72 | 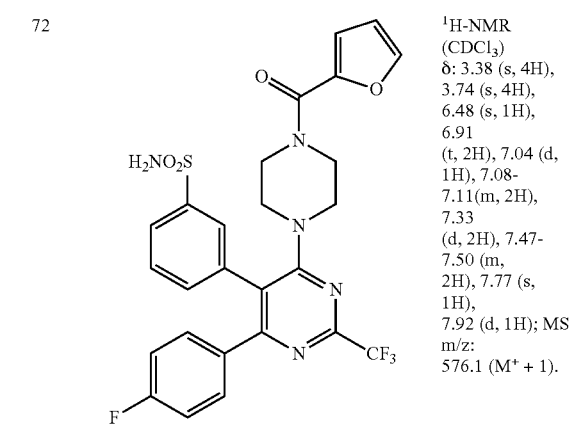 | ¹H-NMR (CDCl₃) δ: 3.38 (s, 4H), 3.74 (s, 4H), 6.48 (s, 1H), 6.91 (t, 2H), 7.04 (d, 1H), 7.08-7.11(m, 2H), 7.33 (d, 2H), 7.47-7.50 (m, 2H), 7.77 (s, 1H), 7.92 (d, 1H); MS m/z: 576.1 (M⁺ + 1). |

| # | Structure | Data |
|---|---|---|
| 73 | 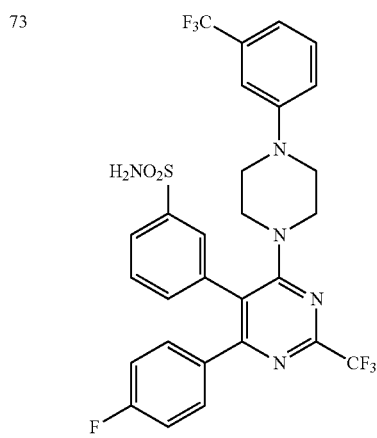 | $^1$H-NMR (CDCl$_3$) δ: 3.14 (d, 4H), 3.47 (s, 4H), 6.91 (t, 2H), 7.02 (d, 2H), 7.08-7.11 (m, 2H), 7.29-7.39 (m, 4H), 7.52 (t, 1H), 7.72 (s, 1H), 7.88 (d, 1H); MS m/z: 626.1 (M$^+$ + 1). |
| 74 | 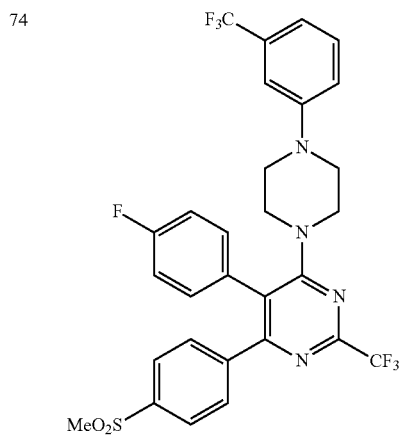 | HPLC (purity): 96.4%; $^1$H-NMR (CDCl$_3$) δ: 3.00 (s, 3H), 3.14 (d, 4H), 3.51 (d, 4H), 6.99-7.11 (m, 7H), 7.33 (d, 3H), 7.80 (d, 2H); MS m/z: 625.1 (M$^+$ + 1). |
| 75 | 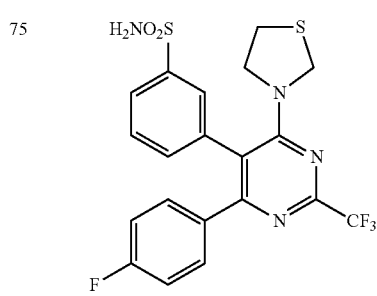 | HPLC (purity): 89%; $^1$H-NMR (CDCl$_3$) δ: 2.93-2.96 (m, 2H), 3.57-3.62 (m, 2H), 4.22 (m, 2H), 6.87-6.91 (m, 2H), 7.07-7.12 (m, 2H), 7.31-7.37 (m, 2H), 7.86 (d, 2H); MS m/z: 485.0 (M$^+$ + 1). |
| 76 | 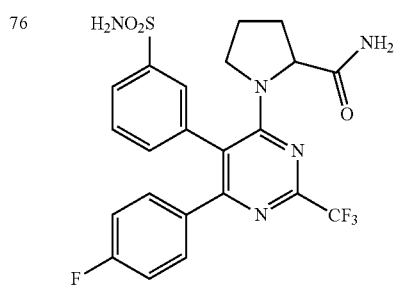 | $^1$H-NMR (CDCl$_3$) δ: 1.94-2.08 (m, 6H), 3.84 (d, 1H), 6.85 (t, 3H), 7.06-7.10 (m, 3H), 7.52 (bs, 2H), 7.84 (d, 2H); MS m/z: 510.1 (M$^+$ + 1). |
| 77 | 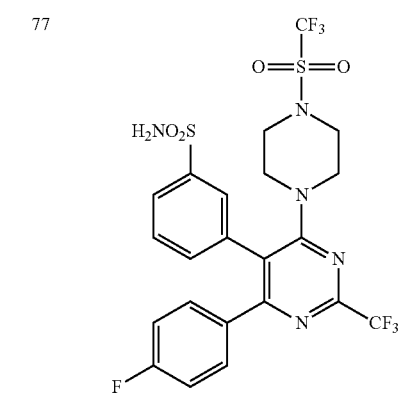 | $^1$H-NMR (CDCl$_3$) δ: 3.40 (s, 8H), 6.90-6.94 (m, 2H), 7.00-7.12 (m, 2H), 7.31 (d, 1H), 7.52 (t, 1H), 7.77 (s, 1H), 7.90 (d, 1H); MS m/z: 614.0 (M$^+$ + 1). |
| 78 | 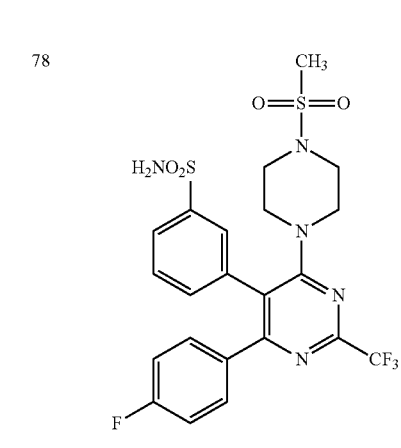 | $^1$H-NMR (CDCl$_3$) δ: 2.83 (s, 3H), 2.99 (s, 4H), 3.32 (s, 4H), 7.06-7.17 (m, 4H), 7.31 (d, 1H), 7.51 (t, 1H), 7.78 (d, 1H), 7.80 (s, 1H); MS m/z: 560.1 (M$^+$ + 1). |
| 79 | 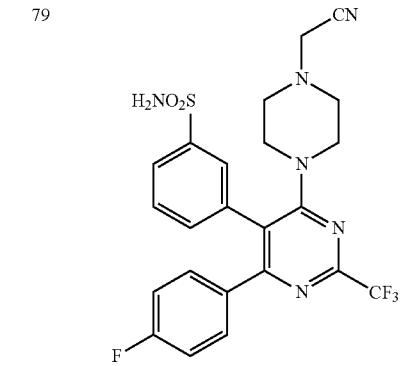 | $^1$H-NMR (CDCl$_3$) δ: 2.37 (d, 4H), 3.30 (d, 4H), 3.67 (s, 2H), 7.04-7.08 (m, 2H), 7.12-7.15 (m, 2H), 7.33 (d, 3H), 7.51 (t, 1H), 7.68 (s, 1H), 7.74 (d, 1H); MS m/z: 521.1 (M$^+$ + 1). |
| 80 | 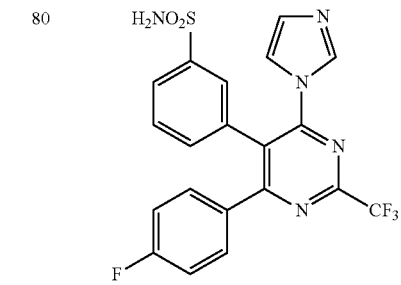 | $^1$H-NMR (CDCl$_3$) δ: 6.97-7.03 (m, 3H), 7.15 (s, 1H), 7.31 (d, 4H), 7.46 (s, 1H), 7.58 (t, 1H), 7.68 (s, 1H), 8.01 (d, 1H); MS m/z: 464.0 (M$^+$ + 1). |

| 81 | 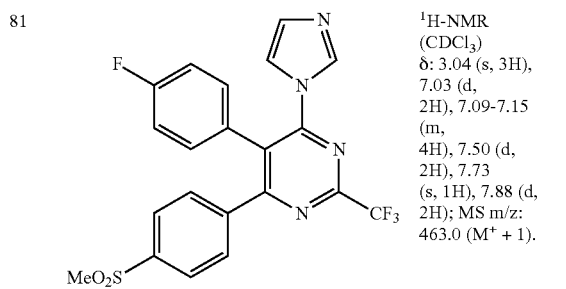 | ¹H-NMR (CDCl₃) δ: 3.04 (s, 3H), 7.03 (d, 2H), 7.09-7.15 (m, 4H), 7.50 (d, 2H), 7.73 (s, 1H), 7.88 (d, 2H); MS m/z: 463.0 (M⁺ + 1). |
|---|---|---|
| 82 | 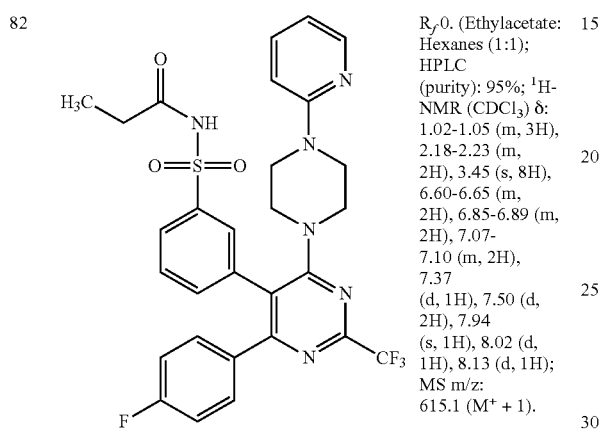 | $R_f$ 0. (Ethylacetate: Hexanes (1:1); HPLC (purity): 95%; ¹H-NMR (CDCl₃) δ: 1.02-1.05 (m, 3H), 2.18-2.23 (m, 2H), 3.45 (s, 8H), 6.60-6.65 (m, 2H), 6.85-6.89 (m, 2H), 7.07-7.10 (m, 2H), 7.37 (d, 1H), 7.50 (d, 2H), 7.94 (s, 1H), 8.02 (d, 1H), 8.13 (d, 1H); MS m/z: 615.1 (M⁺ + 1). |
| 83 | 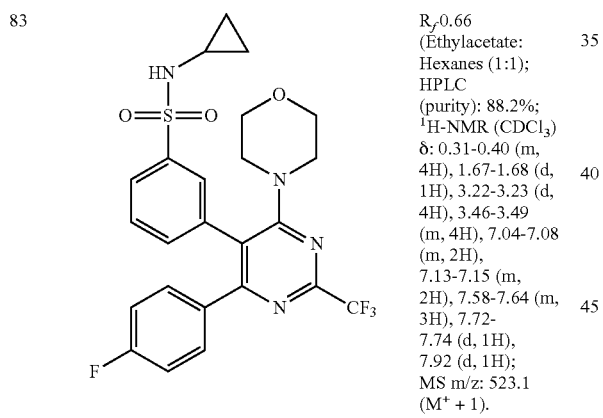 | $R_f$ 0.66 (Ethylacetate: Hexanes (1:1); HPLC (purity): 88.2%; ¹H-NMR (CDCl₃) δ: 0.31-0.40 (m, 4H), 1.67-1.68 (d, 1H), 3.22-3.23 (d, 4H), 3.46-3.49 (m, 4H), 7.04-7.08 (m, 2H), 7.13-7.15 (m, 2H), 7.58-7.64 (m, 3H), 7.72-7.74 (d, 1H), 7.92 (d, 1H); MS m/z: 523.1 (M⁺ + 1). |
| 84 | 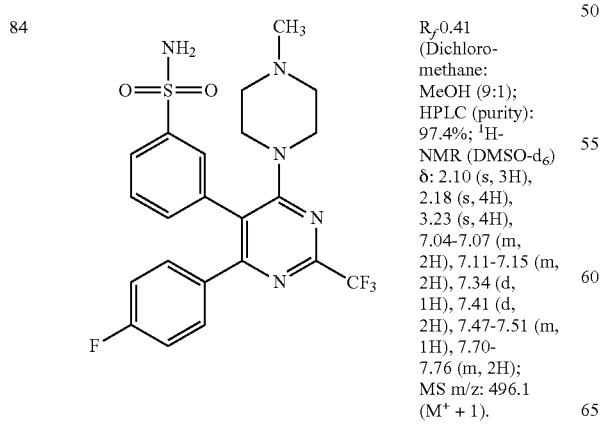 | $R_f$ 0.41 (Dichloromethane: MeOH (9:1); HPLC (purity): 97.4%; ¹H-NMR (DMSO-d₆) δ: 2.10 (s, 3H), 2.18 (s, 4H), 3.23 (s, 4H), 7.04-7.07 (m, 2H), 7.11-7.15 (m, 2H), 7.34 (d, 1H), 7.41 (d, 2H), 7.47-7.51 (m, 1H), 7.70-7.76 (m, 2H); MS m/z: 496.1 (M⁺ + 1). |
| 85 | 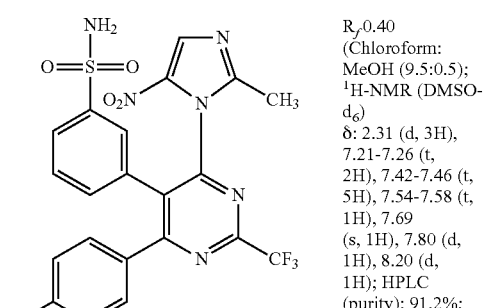 | $R_f$ 0.40 (Chloroform: MeOH (9.5:0.5); ¹H-NMR (DMSO-d₆) δ: 2.31 (d, 3H), 7.21-7.26 (t, 2H), 7.42-7.46 (t, 5H), 7.54-7.58 (t, 1H), 7.69 (s, 1H), 7.80 (d, 1H), 8.20 (d, 1H); HPLC (purity): 91.2%; MS m/z: 523.0 (M⁺ + 1). |
| 86 | 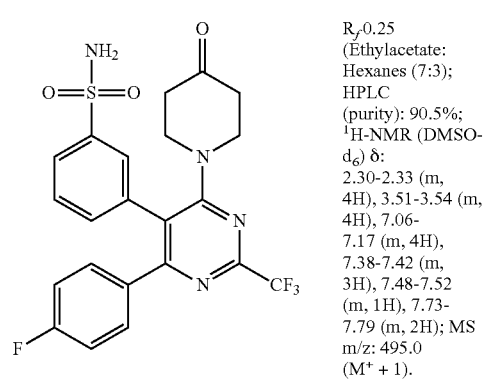 | $R_f$ 0.25 (Ethylacetate: Hexanes (7:3); HPLC (purity): 90.5%; ¹H-NMR (DMSO-d₆) δ: 2.30-2.33 (m, 4H), 3.51-3.54 (m, 4H), 7.06-7.17 (m, 4H), 7.38-7.42 (m, 3H), 7.48-7.52 (m, 1H), 7.73-7.79 (m, 2H); MS m/z: 495.0 (M⁺ + 1). |
| 87 | 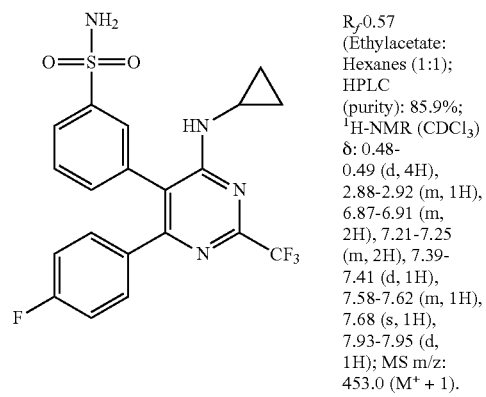 | $R_f$ 0.57 (Ethylacetate: Hexanes (1:1); HPLC (purity): 85.9%; ¹H-NMR (CDCl₃) δ: 0.48-0.49 (d, 4H), 2.88-2.92 (m, 1H), 6.87-6.91 (m, 2H), 7.21-7.25 (m, 2H), 7.39-7.41 (d, 1H), 7.58-7.62 (m, 1H), 7.68 (s, 1H), 7.93-7.95 (d, 1H); MS m/z: 453.0 (M⁺ + 1). |
| 88 | 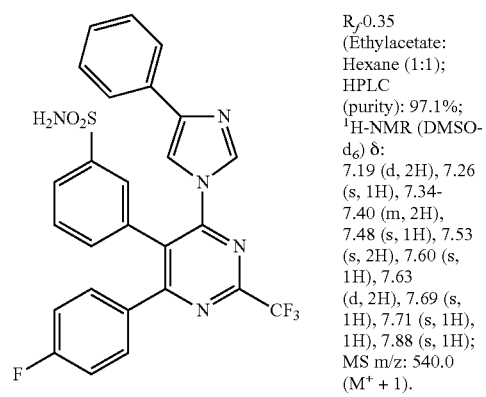 | $R_f$ 0.35 (Ethylacetate: Hexane (1:1); HPLC (purity): 97.1%; ¹H-NMR (DMSO-d₆) δ: 7.19 (d, 2H), 7.26 (s, 1H), 7.34-7.40 (m, 2H), 7.48 (s, 1H), 7.53 (s, 2H), 7.60 (s, 1H), 7.63 (d, 2H), 7.69 (s, 1H), 7.71 (s, 1H), 7.88 (s, 1H); MS m/z: 540.0 (M⁺ + 1). |

| | | |
|---|---|---|
| 89 | 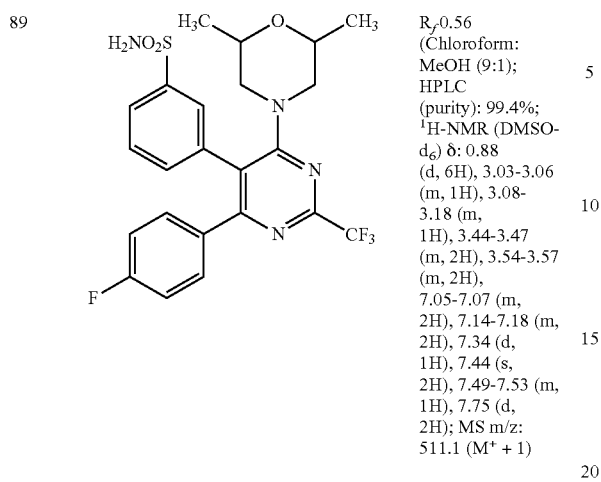 | $R_f$ 0.56 (Chloroform: MeOH (9:1); HPLC (purity): 99.4%; $^1$H-NMR (DMSO-$d_6$) δ: 0.88 (d, 6H), 3.03-3.06 (m, 1H), 3.08-3.18 (m, 1H), 3.44-3.47 (m, 2H), 3.54-3.57 (m, 2H), 7.05-7.07 (m, 2H), 7.14-7.18 (m, 2H), 7.34 (d, 1H), 7.44 (s, 2H), 7.49-7.53 (m, 1H), 7.75 (d, 2H); MS m/z: 511.1 ($M^+$ + 1) |
| 90 | 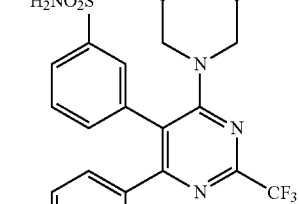 | $R_f$ 0.6 (Chloroform: MeOH (8.5:1.5); HPLC (purity): 99.2%; $^1$H-NMR (CDCl$_3$) δ: 0.74 (d, 6H), 2.21-2.27 (m, 2H), 2.50-2.57 (m, 2H), 3.58-3.61 (d, 2H), 7.03-7.08 (m, 2H), 7.13-7.17 (m, 2H), 7.34 (d, 1H), 7.41 (s, 2H), 7.47-7.51 (m, 1H), 7.70-7.75 (m, 2H); MS m/z: 510.1 ($M^+$ + 1). |
| 91 | 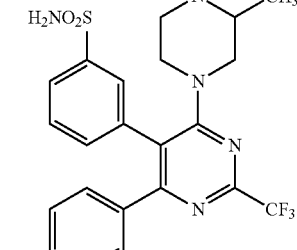 | $R_f$ 0.4 (Chloroform: MeOH (8.5:1.5); HPLC (purity): 96.1%; $^1$H-NMR (DMSO-$d_6$) δ: 0.80-0.81 (d, 3H), 2.41-2.47 (t, 1H), 2.61-2.64 (t, 2H), 2.75-2.80 (t, 2H), 3.56-3.59 (t, 1H), 3.73-3.77 (d, 1H), 7.10-7.14 (t, 2H), 7.19-7.22 (m, 2H), 7.40 (d, 1H), 7.47 (s, 2H), 7.54-7.57 (t, 1H), 7.79 (d, 2H); MS m/z: 496.1 ($M^+$ + 1). |
| 92 | 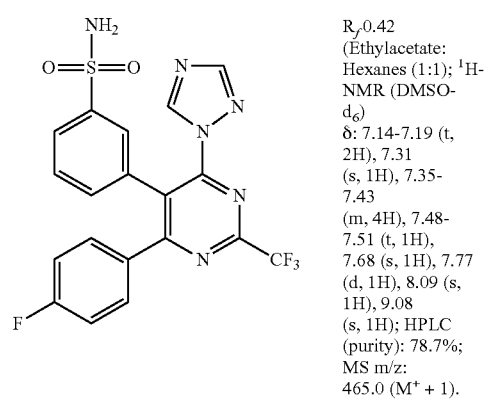 | $R_f$ 0.42 (Ethylacetate: Hexanes (1:1); $^1$H-NMR (DMSO-$d_6$) δ: 7.14-7.19 (t, 2H), 7.31 (s, 1H), 7.35-7.43 (m, 4H), 7.48-7.51 (t, 1H), 7.68 (s, 1H), 7.77 (d, 1H), 8.09 (s, 1H), 9.08 (s, 1H); HPLC (purity): 78.7%; MS m/z: 465.0 ($M^+$ + 1). |
| 93 | 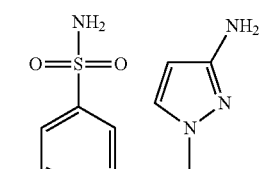 | $R_f$ 0.5 (Dichloromethane: MeOH (9:1); HPLC (purity): 82.4%; $^1$H-NMR (DMSO-$d_6$) δ: 7.03-7.12 (m, 2H), 7.31 (d, 3H), 7.46 (s, 2H), 7.52 (d, 1H), 7.63 (d, 2H), 7.69 (d, 1H), 7.80-7.84 (d, 1H); MS m/z: 479.0 ($M^+$ + 1). |
| 94 | | $R_f$ 0.42 (Ethylacetate: Hexanes (3:7); HPLC (purity): 99.1%; $^1$H-NMR (CDCl$_3$) δ: 2.51-2.53 (m, 4H), 3.58-3.60 (m, 4H), 6.88-6.93 (t, 2H), 7.05-7.08 (m, 2H), 7.33 (d, 1H), 7.49-7.53 (m, 1H), 7.67 (s, 1H), 7.86 (d, 1H); MS m/z: 499.0 ($M^+$ + 1). |

| | | |
|---|---|---|
| 95 | 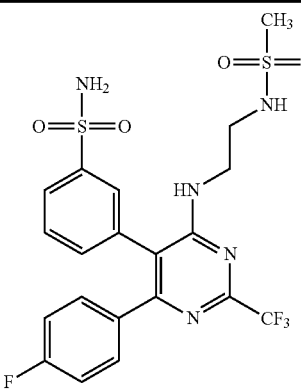 | $R_f$ 0.41 (Ethylacetate: Hexanes (7:3); HPLC (purity): 97%; $^1$H-NMR (DMSO-$d_6$) δ: 2.89 (s, 3H), 3.12-3.17 (m, 2H), 3.40-3.46 (t, 2H), 6.93 (d, 1H), 7.03-7.12 (m, 3H), 7.21-7.23 (m, 2H), 7.35 (s, 2H), 7.44 (d, 1H), 7.60-7.64 (m, 2H), 7.80 (d, 1H); MS m/z: 534.0 (M$^+$ + 1). |
| 96 | 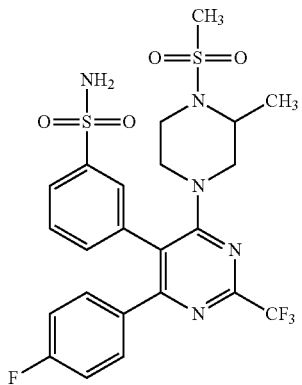 [SMILES: CC1CN(c2nc(C(F)(F)F)nc(-c3ccc(F)cc3)c2-c2cccc(S(N)(=O)=O)c2)CCN1S(C)(=O)=O] | $R_f$ 0.55 (Chloroform: MeOH (9:1); HPLC (purity): 98.8%; $^1$H-NMR (DMSO-$d_6$) δ: 1.06-1.07 (d, 3H), 2.84 (d, 1H), 2.90 (s, 3H), 3.01 (s, 1H), 3.11-3.14 (d, 2H), 3.19-3.26 (t, 1H), 3.39-3.42 (d, 1H), 3.78-3.81 (d, 1H), 7.05-7.09 (t, 2H), 7.15-7.18 (t, 2H), 7.36 (s, 1H), 7.51-7.55 (t, 2H), 7.74-7.79 (t, 1H); MS m/z: 574.0 (M$^+$ + 1). |
| 97 | 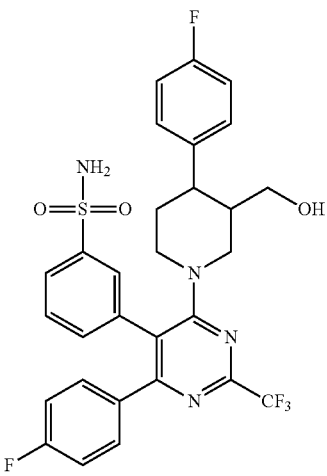 [SMILES: NS(=O)(=O)c1cccc(-c2c(-c3ccc(F)cc3)nc(C(F)(F)F)nc2N2CCC(c3ccc(F)cc3)C(CO)C2)c1] | $R_f$ 0.3 (chloroform: MeOH (9:1); HPLC (purity): 84.8%; $^1$H-NMR (CDCl$_3$) δ: 1.86-1.89 (m, 1H), 2.34-2.37 (m, 1H), 2.59 (s, 4H), 3.21-3.23 (m, 1H), 3.28-3.30 (m, 1H), 4.04-4.11 (m, 2H), 6.93-6.99 (m, 5H), 7.04 (d, 1H), 7.10 (d, 2H), 7.36-7.39 (t, 3H), 7.90 (d, 1H), 8.14 (s, 1H); MS m/z: 622.1 (M$^+$ + 1). |
| 98 | 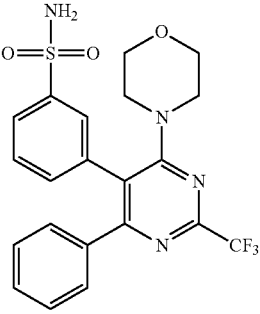 [SMILES: NS(=O)(=O)c1cccc(-c2c(-c3ccccc3)nc(C(F)(F)F)nc2N2CCOCC2)c1] | $R_f$ 0.61 (Ethylacetate: Hexanes (8:2); HPLC (purity): 99%; $^1$H-NMR (DMSO-$d_6$) δ: 3.21 (d, 4H), 3.43-3.48 (m, 4H), 7.09 (d, 2H), 7.21-7.30 (m, 4H), 7.43-7.47 (m, 3H), 7.72 (d, 1H), 7.79 (s, 1H); MS m/z: 464.8 (M$^+$ + 1). |

Example 99

Synthesis of 3-[6-(4-fluorophenyl)-4-(2-morpholin-4-ylethoxy)-2-(trifluoro methyl)pyrimidin-5-yl]benzenesulfonamide

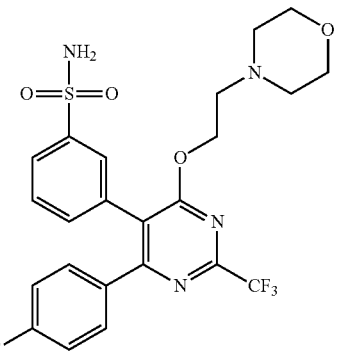

To a solution of 6-(4-fluorophenyl)-5-phenyl-2-(trifluoromethyl)pyrimidin-4(3H)-one (1 g, 3.0 mmol) in acetonitrile (5 ml) was added chloroethyl morpholine (0.84 g, 4.5 mmol) and caesium carbonate (3 g, 9 mmol). The reaction mixture was refluxed at 70-80° C. for 5 hours. Subsequently the reaction slurry was poured into the water and extracted with dichloromethane (3×30 ml). The organic layer was dried over anhydrous sodium sulphate and evaporated at reduced pressure to give the desired compound that was subjected to further transformation without purification.

To pyrimidine (0.5 g, 1.2 mmol) was added chlorosulphonic acid (10 ml, 0.150 mol) in ice-cold condition. The reaction mixture was stirred at room temperature for 28 hours. The reaction mixture was poured into water and extracted with dichloromethane (3×25 ml). The organic layer was dried over anhydrous sodium sulphate and evaporated at reduced pressure to give the desired compound that was subjected to further transformation without purification.

To the stirring solution of chlorosulphonyl derivative (0.5 g, 0.917 mmol) in dichloromethane (5 ml) was purged ammonia gas for 30 minutes through ammonia purging setup. The reaction slurry was poured into the water and extracted with dichloromethane (3×25 ml). The organic layer was dried over anhydrous sodium sulphate and upon evaporation at reduced pressure it gave the desired solid (0.379 g, 78.6%), $R_f$ 0.51 (Ethylacetate: Hexanes, 7:3); HPLC (purity): 94.6%; $^1$H-NMR (DMSO-$d_6$) δ: 2.33 (s, 4H), 2.61-2.63 (t, 2H), 3.43-3.49 (m, 4H), 4.54-4.57 (t, 2H), 7.13-7.17 (m, 3H), 7.37-7.40 (m, 3H), 7.44-7.47 (m, 2H), 7.55 (d, 1H), 7.80 (d, 1H); MS m/z: 527.1 (M$^+$1).

Example 100

Synthesis of 3-{4-[4-(2-cyanoethyl)piperazin-1-yl]-6-(4-fluorophenyl)-2-(trifluoro methyl)pyrimidin-5-yl}benzenesulfonamide To a solution of amine (0.1 g, 0.206 mmol) in dichloromethane (1.5 ml) was added acrylonitrile (0.016 ml, 0.248 mmol) and triethyl amine (0.033 ml, 0.25 mmol). The reaction slurry was stirred at room temperature for 18 hours and then it was poured into the ice-cold water and extracted with dichloromethane (2×20 ml). The organic layer was dried over anhydrous sodium sulphate and evaporated to give the solid that was subjected to column chromatography using a gradient of methanol in dichloromethane (0-1%). Yield-0.05 g (45%), $R_f$ 0.52 (Dichloromethane:MeOH (9:1); HPLC (purity): 96.1%; $^1$H-NMR (DMSO-$d_6$) δ: 2.35 (s, 6H), 3.26 (s, 6H), 7.06-7.14 (m, 5H), 7.42 (s, 1H), 7.73 (d, 2H); MS m/z: 535.1 (M$^+$+1).

The following compounds were prepared by the above procedures

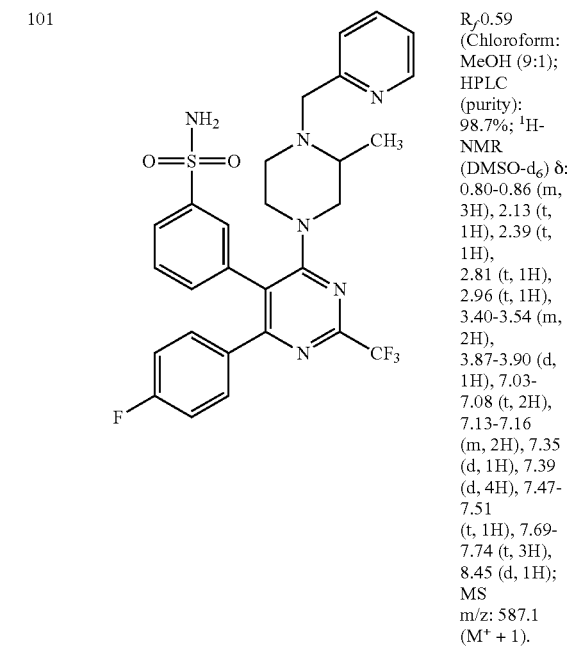
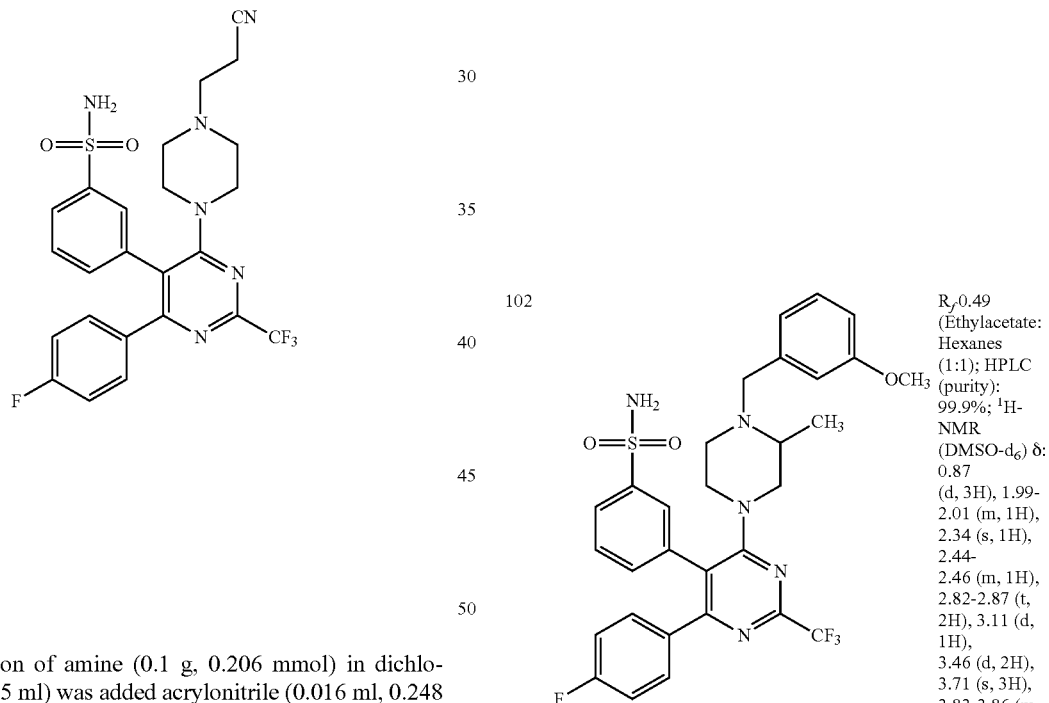

| | | |
|---|---|---|
| 101 | | $R_f$ 0.59 (Chloroform: MeOH (9:1); HPLC (purity): 98.7%; $^1$H-NMR (DMSO-$d_6$) δ: 0.80-0.86 (m, 3H), 2.13 (t, 1H), 2.39 (t, 1H), 2.81 (t, 1H), 2.96 (t, 1H), 3.40-3.54 (m, 2H), 3.87-3.90 (d, 1H), 7.03-7.08 (t, 2H), 7.13-7.16 (m, 2H), 7.35 (d, 1H), 7.39 (d, 4H), 7.47-7.51 (t, 1H), 7.69-7.74 (t, 3H), 8.45 (d, 1H); MS m/z: 587.1 (M$^+$ + 1). |
| 102 | | $R_f$ 0.49 (Ethylacetate: Hexanes (1:1); HPLC (purity): 99.9%; $^1$H-NMR (DMSO-$d_6$) δ: 0.87 (d, 3H), 1.99-2.01 (m, 1H), 2.34 (s, 1H), 2.44-2.46 (m, 1H), 2.82-2.87 (t, 2H), 3.11 (d, 1H), 3.46 (d, 2H), 3.71 (s, 3H), 3.83-3.86 (m, 1H), (6.79-6.85 (t, 3H), 7.03-7.07 (t, 2H), 7.13-7.19 (m, 3H), 7.22 (s, 1H), 7.34 (d, 2H), 7.47-7.51 (t, 1H), 7.53-7.54 (t, 2H); MS m/z: 616.1 (M$^+$ + 1). |

| | | |
|---|---|---|
| 103 | 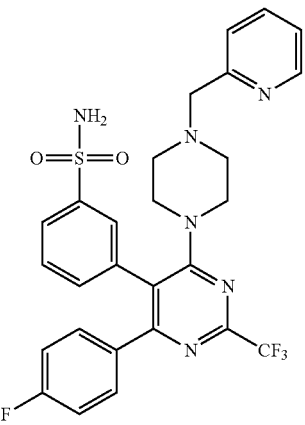 [SMILES: NS(=O)(=O)c1cccc(-c2c(-c3ccc(F)cc3)nc(C(F)(F)F)nc2N2CCN(Cc3ccccn3)CC2)c1] | R$_f$ 0.58 (Chloroform: MeOH (9:1); HPLC (purity): 95.1%; $^1$H-NMR (DMSO-d$_6$) δ: 2.34 (s, 4H), 3.28 (s, 4H), 3.59 (s, 2H), 7.04-7.08 (t, 2H), 7.11-7.15 (m, 2H), 7.35 (s, 1H), 7.38-7.39 (d, 4H), 7.49 (s, 1H), 7.70-7.73 (t, 3H), 8.46-8.47 (d, 1H); MS m/z: 573.1 (M$^+$ + 1). |
| 104 | 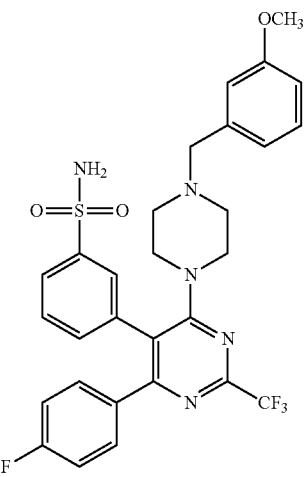 [SMILES: COc1cccc(CN2CCN(c3nc(C(F)(F)F)nc(-c4ccc(F)cc4)c3-c3cccc(S(N)(=O)=O)c3)CC2)c1] | R$_f$ 0.42 (Ethylacetate: Hexanes (1:1); HPLC (purity): 94.5%; $^1$H-NMR (DMSO-d$_6$) δ: 2.49 (s, 4H), 3.25 (s, 4H), 3.39 (s, 2H), 3.71 (s, 3H), 6.78-6.83 (t, 3H), 7.03-7.08 (t, 2H), 7.11-7.15 (m, 1H), 7.2 (s, 1H), 7.34 (d, 1H), 7.38 (s, 2H), 7.48 (s, 1H), 7.69-7.72 (t, 1H); MS m/z: 602.1 (M$^+$ + 1). |
| 105 | 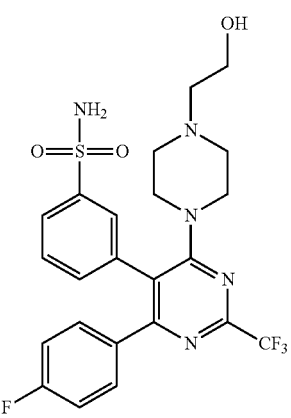 | R$_f$ 0.43 (Dichloromethane: MeOH (9:1); HPLC (purity): 95.7%; $^1$H-NMR (CDCl$_3$) δ: 2.42-2.44 (m, 4H), 2.52-2.55 (m, 2H), 3.32-3.34 (t, 4H), 3.59-3.65 (m, 2H), 6.88-6.93 (t, 2H), 7.06-7.10 (m, 2H), 7.31 (d, 1H), 7.47 (d, 1H), 7.72 (s, 1H), 7.84 (d, 1H); MS m/z: 526.1 (M$^+$ + 1). |
| 106 | 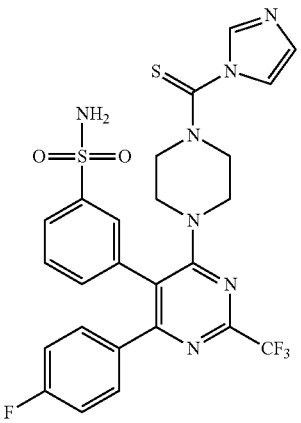 [SMILES: NS(=O)(=O)c1cccc(-c2c(-c3ccc(F)cc3)nc(C(F)(F)F)nc2N2CCN(C(=S)n3ccnc3)CC2)c1] | R$_f$ 0.29 (Dichloromethane: MeOH (9:1); HPLC (purity): 96.6%; $^1$H-NMR (CDCl$_3$) δ: 3.42-3.48 (d, 4H), 3.85 (s, 4H), 6.91-6.95 (m, 2H), 7.08-7.17 (m, 4H), 7.29-7.31 (d, 2H), 7.49-7.53 (m, 1H), 7.83-7.85 (d, 1H), 7.89-7.91 (d, 1H); MS m/z: 592.0 (M$^+$ + 1). |

Example 107

Synthesis of 3-[4-(1,1-dioxido-1,3-thiazolidin-3-yl)-6-(4-fluorophenyl)-2-(trifluoromethyl)pyrimidin-5-yl]benzenesulfonamide

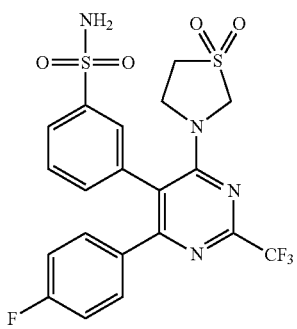 [SMILES: NS(=O)(=O)c1cccc(-c2c(-c3ccc(F)cc3)nc(C(F)(F)F)nc2N2CCS(=O)(=O)C2)c1]

To a mixture of 3-[4-(4-fluorophenyl)-6-(1,3-thiazolidin-3-yl)-2-(trifluoro methyl)pyrimidin-5-yl]benzenesulfonamide; (0.2 g, 0.41 mmol) in methanol (3 ml) was added oxone (0.51 g, 0.83 mmol) in water (6 ml). The resulting slurry was stirred for 27 hours at room temperature. The reaction mixture was poured into water and extracted with ethylacetate (3×30 ml). The organic layer was dried over anhydrous sodium sulphate and evaporated at reduced pressure to give a solid, which was subjected to column chromatography using a gradient of ethylacetate in hexane (0-25%). Yield-0.14 g (65.7%), R$_f$ 0.65 (Ethylacetate:Hexanes (7:3); HPLC (purity): 98.7%; $^1$H-NMR (DMSO-d$_6$) δ: 3.39-3.46 (m, 2H), 3.84-3.86 (t, 2H), 4.05 (s, 2H), 7.06-7.10 (t, 2H), 7.16-7.19 (t, 2H), 7.41 (s, 2H), 7.46 (s, 1H), 7.52-7.56 (t, 1H), 7.74 (s, 1H), 7.79 (d, 1H); MS m/z: 517.0 (M$^+$+1).

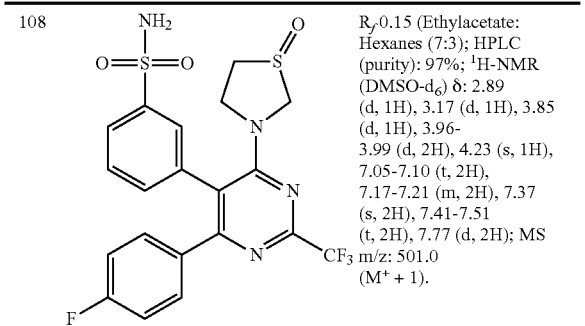

108 — R$_f$ 0.15 (Ethylacetate:Hexanes (7:3); HPLC (purity): 97%; $^1$H-NMR (DMSO-d$_6$) δ: 2.89 (d, 1H), 3.17 (d, 1H), 3.85 (d, 1H), 3.96-3.99 (d, 2H), 4.23 (s, 1H), 7.05-7.10 (t, 2H), 7.17-7.21 (m, 2H), 7.37 (s, 2H), 7.41-7.51 (t, 2H), 7.77 (d, 2H); MS m/z: 501.0 (M$^+$ + 1).

Preparation of the following compounds was carried out using the well-known procedure of treating an amine with the corresponding acid chloride in presence of a base (triethylamine) in dichloromethane (solvent) and usual workup and purification to provide the desired compounds. Example 113 was obtained by treating the ketone with o-methylhydroxylamine and a base followed by usual workup and purification.

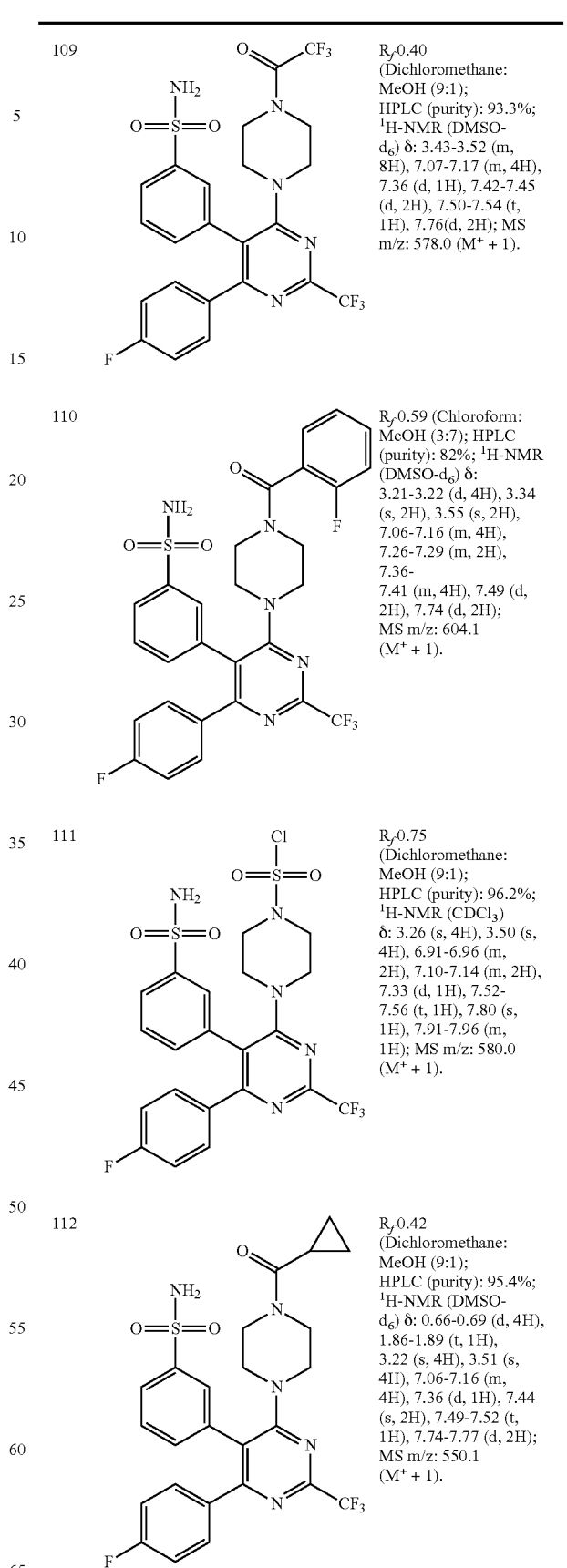

109 — R$_f$ 0.40 (Dichloromethane:MeOH (9:1); HPLC (purity): 93.3%; $^1$H-NMR (DMSO-d$_6$) δ: 3.43-3.52 (m, 8H), 7.07-7.17 (m, 4H), 7.36 (d, 1H), 7.42-7.45 (d, 2H), 7.50-7.54 (t, 1H), 7.76(d, 2H); MS m/z: 578.0 (M$^+$ + 1).

110 — R$_f$ 0.59 (Chloroform:MeOH (3:7); HPLC (purity): 82%; $^1$H-NMR (DMSO-d$_6$) δ: 3.21-3.22 (d, 4H), 3.34 (s, 2H), 3.55 (s, 2H), 7.06-7.16 (m, 4H), 7.26-7.29 (m, 2H), 7.36-7.41 (m, 4H), 7.49 (d, 2H), 7.74 (d, 2H); MS m/z: 604.1 (M$^+$ + 1).

111 — R$_f$ 0.75 (Dichloromethane:MeOH (9:1); HPLC (purity): 96.2%; $^1$H-NMR (CDCl$_3$) δ: 3.26 (s, 4H), 3.50 (s, 4H), 6.91-6.96 (m, 2H), 7.10-7.14 (m, 2H), 7.33 (d, 1H), 7.52-7.56 (t, 1H), 7.80 (s, 1H), 7.91-7.96 (m, 1H); MS m/z: 580.0 (M$^+$ + 1).

112 — R$_f$ 0.42 (Dichloromethane:MeOH (9:1); HPLC (purity): 95.4%; $^1$H-NMR (DMSO-d$_6$) δ: 0.66-0.69 (d, 4H), 1.86-1.89 (t, 1H), 3.22 (s, 4H), 3.51 (s, 4H), 7.06-7.16 (m, 4H), 7.36 (d, 1H), 7.44 (s, 2H), 7.49-7.52 (t, 1H), 7.74-7.77 (d, 2H); MS m/z: 550.1 (M$^+$ + 1).

| 113 | 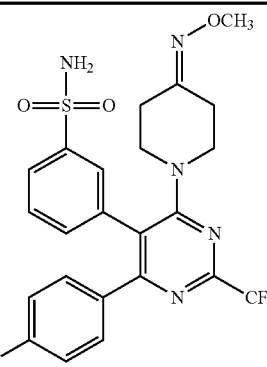 | R$_f$ 0.61 (Ethylacetate: Hexanes (7:3); HPLC (purity): 95.2%; $^1$H-NMR (DMSO-d$_6$) δ: 2.20-2.23 (t, 4H), 2.38-2.41 (t, 4H), 3.70 (s, 3H), 7.05-7.16 (m, 4H), 7.37 (d, 3H), 7.47-7.51 (t, 1H), 7.74 (d, 2H); MS m/z: 524.1 (M$^+$ + 1). |

| 115 | 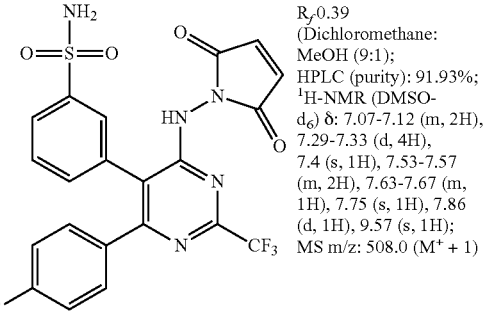 | R$_f$ 0.39 (Dichloromethane: MeOH (9:1); HPLC (purity): 91.93%; $^1$H-NMR (DMSO-d$_6$) δ: 7.07-7.12 (m, 2H), 7.29-7.33 (d, 4H), 7.4 (s, 1H), 7.53-7.57 (m, 2H), 7.63-7.67 (m, 1H), 7.75 (s, 1H), 7.86 (d, 1H), 9.57 (s, 1H); MS m/z: 508.0 (M$^+$ + 1) |

Example 114

Synthesis of 3-[6-(4-fluorophenyl)-4-[(3-methyl-2,5-dioxo-2,5-dihydro-1H-pyrrol-1-yl)amino]-2-(trifluoromethyl)pyrimidin-5-yl]benzenesulfonamide

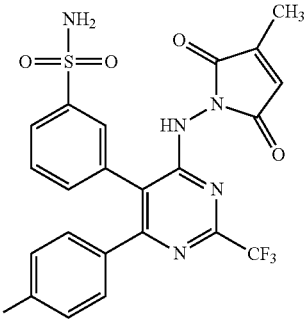

To a solution of hydrazine (0.15 g, 0.351 mmol) in chloroform (5 ml) was added citraconic anhydride (0.097 ml, 3 mmol). The resulting solution was stirred at 60° C. for 18 hours. Subsequently water (20 ml) and dichloromethane (3×25 ml) were added to the reaction mixture. The organic layer was separated, dried over anhydrous sodium sulphate and concentrated in vacuo. The resulting residue was subjected to column chromatography using a gradient of methanol in dichloromethane (0-1.5%). Yield—0.07 g (38.2%), R$_f$ 0.44 (Dichloromethane:Methanol (9:1); HPLC (purity): 89.2%; $^1$H-NMR (CDCl$_3$) δ: 2.10 (s, 3H), 6.46 (s, 1H), 6.92-6.96 (m, 2H), 7.29-7.33 (m, 2H), 7.47 (d, 1H), 7.57-7.61 (m, 1H), 7.95 (d, 1H), 8.02 (s, 1H); MS m/z: 522.0 (M$^+$+1).

The following compound was prep red according to the above-mentioned procedure

Example 116

Synthesis of 3-[6-{4-[5-(trifluoromethyl)pyridin-2-yl]piperazin-1-yl}-4-phenyl-2-(trifluoromethyl)pyrimidin-4-yl]benzensulfonamide

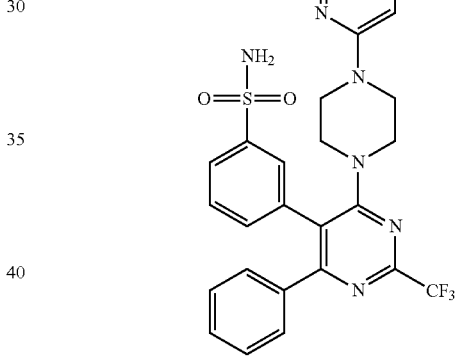

Step 1

Preparation of 1-[5-(trifluoromethyl)pyridin-2-yl]piperazine

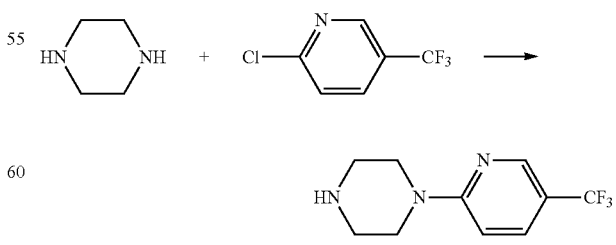

Piperazine (1.2 g, 13.77 mM) was heated with 2-chloro-5-(trifluoromethyl)pyridine (0.5 g, 2.75 mmol) in THF (2 mL) for 2 hours. Subsequently the reaction mixture was poured

87 onto crushed ice and extracted with ethyl acetate. The organic layer was washed with sodium bicarbonate and evaporated to furnish the required product.

Step 2

Preparation of 3-[6-{4-[5-(trifluoromethyl)pyridin-2-yl]piperazin-1-yl}-5-phenyl-2-(trifluoromethyl)pyrimidin-4-yl]benzenesulfonamide

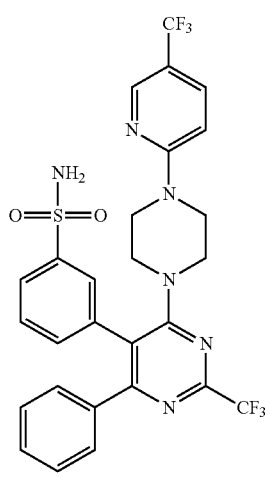 [SMILES: NS(=O)(=O)c1cccc(-c2c(-c3ccccc3)nc(C(F)(F)F)nc2N2CCN(c3ccc(C(F)(F)F)cn3)CC2)c1]

A solution of 3-[6-chloro-5-phenyl-2-(trifluoromethyl)pyrimidin-4-yl]benzenesulfonamide (0.1 g, 0.242 mmol) in pyridine (2 ml) was treated with 1-[5-(trifluoromethyl)pyridin-2-yl]piperazine (0.3 g, 0.68 mmol) and the reaction mixture was stirred for 1 hour at room temperature. Subsequently the reaction mixture was poured onto crushed ice containing two drops of concentrated hydrochloric acid, extracted with ethyl acetate (25 ml) and the organic layer was washed with brine and evaporated. The title compound was obtained by column chromatographic purification of the crude material with 30% ethyl acetate in hexane. $^1$H-NMR (DMSO-d$_6$) δ: 3.33-3.37 (m, 4H), 3.56 (m, 4H), 6.86-6.88 (d, 1H), 7.10-7.12 (d, 2H), 7.22-7.29 (m, 3H), 7.35-7.37 (m, 1H), 7.44-7.48 (m, 1H), 7.74-7.79 (m, 3H), 8.38 (s, 1H); MS m/z: 608.8 (M$^+$).

88

Example 117

Synthesis of 3-[6-{4-[2,6-dimethoxypyrimidin-4-yl]piperazin-1-yl}-5-phenyl-2-(trifluoromethyl)pyrimidin-4-yl]benzenesulfonamide

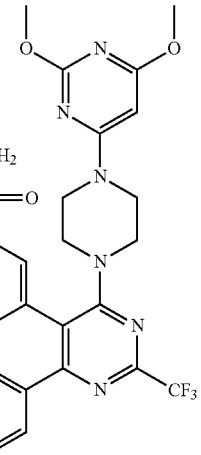

Step 1

Preparation of 2,4-dimethoxy-6-piperazin-1-ylpyrimidine

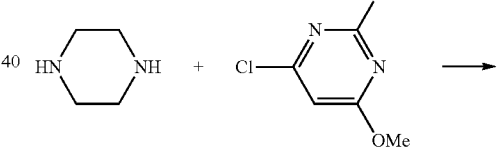

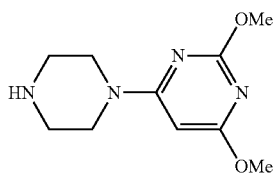

Piperazine (1.23 g, 14.32 mmol) was treated with 6-chloro-2,4-dimethoxy pyrimidine (0.5 g, 2.86 mmol) in acetonitrile (5 mL) and the reaction mixture was stirred at room temperature for 6 hours. Subsequently the reaction mixture was poured onto ice-cold water (25 ml) and extracted with ethyl acetate (25 ml). The organic layer was washed with aqueous sodium bicarbonate solution and evaporated to furnish the required compound.

Step 2

Preparation of 3-[6-{4-[2,6-dimethoxypyrimidin-4-yl]piperazin-1-yl}-5-phenyl-2-(trifluoromethyl)pyrimidin-4-yl]benzenesulfonamide

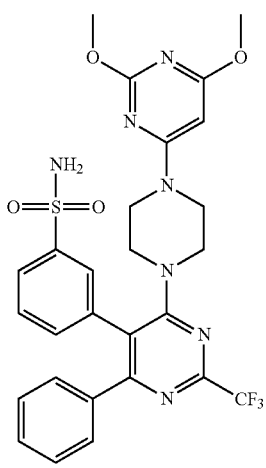 [SMILES: COc1cc(N2CCN(c3nc(C(F)(F)F)nc(-c4ccccc4)c3-c3cccc(S(N)(=O)=O)c3)CC2)nc(OC)n1]

A solution of 3-[6-chloro-5-phenyl-2-(trifluoromethyl)pyrimidin-4-yl]benzenesulfonamide (0.1 g, 0.24 mmol) in pyridine (1.5 ml) was treated with 2,4-dimethoxy-6-piperazin-1-ylpyrimidine (0.081 g, 0.363 mmol) and the reaction mixture was stirred for 8 hours. Subsequently the reaction mixture was poured onto ice-cold water and extracted with ethyl acetate (25 ml). The organic layer was washed with brine and evaporated to furnish the title compound. $^1$H-NMR (CDCl$_3$) δ: 3.39-3.41 (m, 4H), 3.51-3.52 (m, 4H), 3.87-3.88 (s, 6H), 7.07-7.09 (d, 2H), 7.20-7.26 (m, 3H), 7.30-7.32 (m, 1H), 7.47-7.61 (t, 1H), 7.64 (s, 1H), 7.82-7.87 (m, 2H); MS m/z: 601.8 (M$^+$).

Example 118

Synthesis of 3-[6-{4-[5-(nitro)pyridin-2-yl]piperazin-1-yl}-5-phenyl-2-(trifluoromethyl)pyrimidin-4-yl]benzenesulfonamide

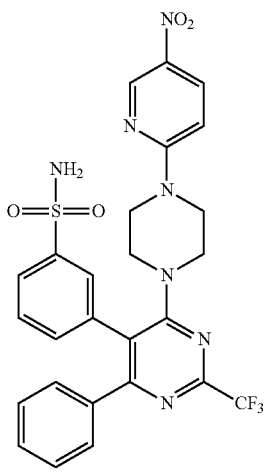 [SMILES: NS(=O)(=O)c1cccc(-c2c(-c3ccccc3)nc(C(F)(F)F)nc2N2CCN(c3ccc([N+](=O)[O-])cn3)CC2)c1]

Step 1

Preparation of 1-(5-nitropyridin-2-yl)piperazine

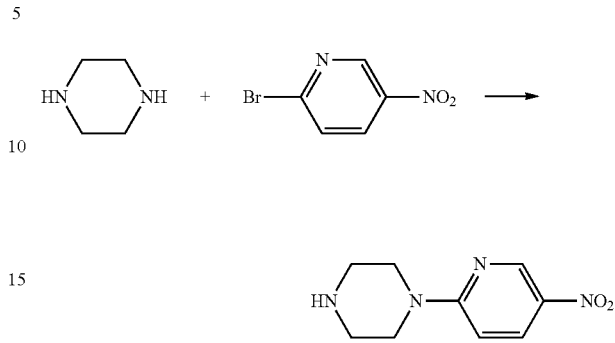

2-Bromo-5-nitropyridine (0.3 g, 1.48 mmol) was treated with piperazine (0.64 g, 7.89 mmol) in tetrahydrofuran (4 ml) and the reaction mixture was stirred for 30 minutes. Subsequently the reaction mixture was poured onto ice-cold water (25 ml) and extracted with ethyl acetate (25 ml). The organic layer was washed with brine and evaporated to furnish the product.

Step 2

Preparation of 3-[6-{4-[5-(nitro) pyridin-2-yl]piperazin-1-yl}-5-phenyl-2-(trifluoromethyl)pyrimidin-4-yl]benzenesulfonamide

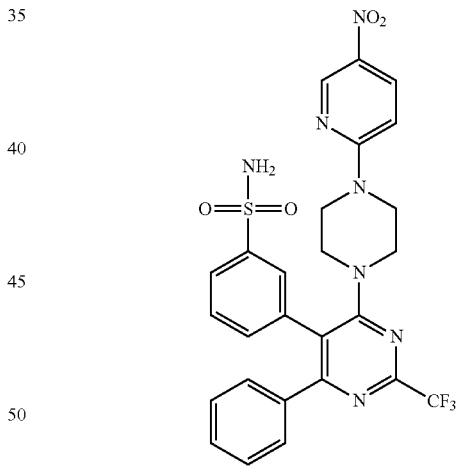

The solution of 3-[6-chloro-5-phenyl-2-(trifluoromethyl)pyrimidin-4-yl]benzenesulfonamide (0.1 g, 0.242 mmol) in pyridine (2 ml) was treated with 1-(5-nitropyridin-2-yl)piperazine (0.075 g, 0.363 mmol) and stirred for 11 hours. Subsequently the reaction mixture was poured onto ice-cold water and extracted with ethyl acetate (25 ml). The organic layer was washed with brine and evaporated to give the crude material. Purification by column chromatography (elution with 70% ethyl acetate in hexane) yielded the title compound. $^1$H-NMR (CDCl$_3$) δ: 3.45-3.46 (m, 4H), 3.72 (m, 4H), 6.52-6.54 (d, 1H), 7.08-7.11 (d, 2H), 7.21-7.26 (m, 2H), 7.32-7.34 (d, 1H), 7.40-7.42 (d, 1H), 7.50 (m, 1H), 7.68 (s, 1H), 7.84-7.89 (m, 1H), 8.21-8.23 (d, 1H), 8.99 (s, 1H); MS m/z: 585.8 (M$^+$).

Example 119

Synthesis of 3-[6-{4-[5-(amino)pyridin-2-yl]piperazin-1-yl}-4-[4-fluorophenyl]-2-(trifluoromethyl)pyrimidin-5-yl]benzenesulfonamide

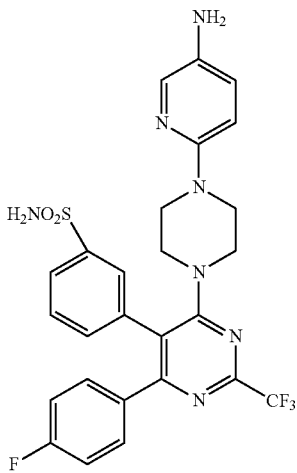 [SMILES: Nc1ccc(N2CCN(c3nc(C(F)(F)F)nc(-c4ccc(F)cc4)c3-c3cccc(S(N)(=O)=O)c3)CC2)nc1]

3-[6-{4-[5-(Nitro)pyridin-2-yl]piperazin-1-yl}-4-[4-fluorophenyl]-2-(trifluoromethyl)pyrimidin-5-yl]benzenesulfonamide (0.13 g, 0.22 mmol) was taken in concentrated hydrochloric acid (1.5 ml) and to this tin (II) chloride dihydrate (0.145 g, 0.65 mmol) was added and the reaction mixture was stirred for 24 hours at room temperature. Subsequently the reaction mixture was poured onto crushed ice, neutralized with sodium bicarbonate, and extracted with ethyl acetate. Evaporation of the solvent yielded the required product. $^1$H-NMR (DMSO-$d_6$) δ: 3.13 (m, 4H), 3.30 (m, 4H), 4.58 (br, 2H, $D_2O$ exchangeable), 6.57-6.59 (m, 1H), 6.88 (d, 1H), 7.04-7.09 (m, 2H), 7.12-7.14 (m, 2H), 7.39 (br, 2H, $D_2O$ exchangeable), 7.41 (d, 1H), 7.50-7.55 (m, 2H), 7.73-7.77 (m, 2H); MS m/z: 574.1 ($M^+$+1).

Example 120

Synthesis of 4-[5-(acetylamino)pyridin-2-yl]piperazin-1-yl-5-(4-fluorophenyl)-6-[4-(methylsulfonyl)phenyl]-2-(trifluoromethyl)pyrimidine

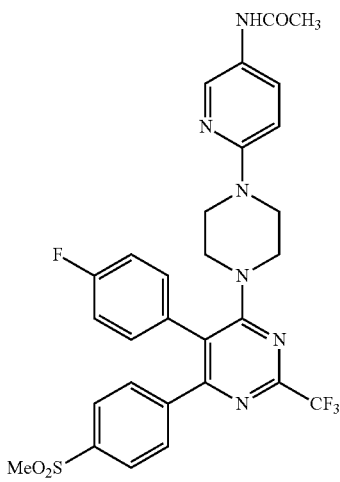

4-Chloro-5-(4-fluorophenyl)-6-[4-(methylsulfonyl)phenyl]-2-(trifluoromethyl)pyrimidine (0.15 g, 0.35 mmol) was treated with 1-(5-nitropyridin-2-yl)piperazine (0.087 g, 0.418 mmol) and diisopropylethylamine (0.06 mL, 0.35 mmol), acetonitrile (2.5 ml) and the reaction mixture was heated at 60-65° C. for 2 hours. Subsequently the reaction mixture was precipitated by the addition of diisopropyl ether (2 ml). The above-obtained solid (0.11 g, 0.182 mmol) was taken up in acetic acid (2 ml) and tin (II) chloride dihydrate (0.123 g, 0.182 mmol) was added to it. Stirring was continued further for 11 hours and then the reaction mixture was poured onto ice-cold water and extracted with ethyl acetate (2×25 ml). After neutralization with sodium bicarbonate, the organic layer was evaporated to obtain the crude material, which was purified by column chromatography (2% MeOH in dichloromethane) to yield the title compound. $^1$H-NMR (DMSO-$d_6$) δ: 1.99 (s, 3H), 3.19 (s, 3H), 3.29-3.40 (m, 8H), 6.77 (d, 1H), 7.19-7.23 (m, 2H), 7.31-7.34 (m, 2H), 7.36 (d, 2H), 7.74 (d, 1H), 7.80 (d, 2H), 8.24 (d, 1H), 9.77 (s, 1H, $D_2O$ exchangeable); MS m/z: 615.1 ($M^+$+1).

Example 121

Synthesis of N-({3-[4-pyridin-2-yl]piperazin-1-yl)-6-(4-fluorophenyl)-2-(trifluoromethyl)pyrimidin-5-yl}phenyl)sulfonyl)acetamide

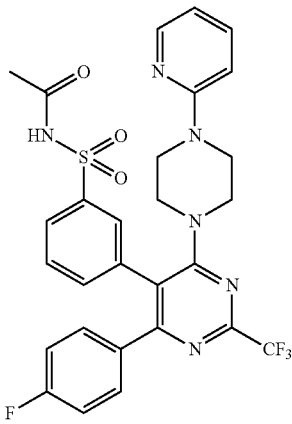 [SMILES: CC(=O)NS(=O)(=O)c1cccc(-c2c(-c3ccc(F)cc3)nc(C(F)(F)F)nc2N2CCN(c3ccccn3)CC2)c1]

3-[4-{4-(5-Pyridin-2-yl)piperazin-1-yl)-6-(4-fluorophenyl)-2-(trifluoromethyl)pyrimidin-5-yl]benzenesulfonamide (0.1 g, 0.178 mmol) was treated with acetyl chloride (0.35 ml) and the reaction mixture was stirred for 40 hours. Subsequently it was poured onto crushed ice, extracted with dichloromethane (25 ml) and washed with brine. The organic layer was evaporated to furnish the required compound. $^1$H-NMR (DMSO-$d_6$) δ: 1.81 (s, 3H), 3.32-3.37 (m, 8H), 6.62 (t, 1H), 6.75 (d, 1H), 7.02-7.07 (m, 2H), 7.11-7.14 (m, 2H), 7.50-7.59 (m, 3H), 7.80 (s, 1H), 7.84 (d, 1H), 8.06 (d, 1H), 12.09 (brs, 1H, $D_2O$ exchangeable); MS m/z: 601.1 ($M^+$+1). The following compound was prepared according to the procedure described above.

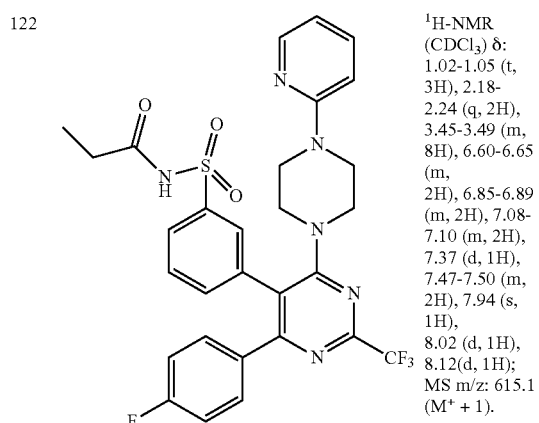

122

¹H-NMR (CDCl₃) δ: 1.02-1.05 (t, 3H), 2.18-2.24 (q, 2H), 3.45-3.49 (m, 8H), 6.60-6.65 (m, 2H), 6.85-6.89 (m, 2H), 7.08-7.10 (m, 2H), 7.37 (d, 1H), 7.47-7.50 (m, 2H), 7.94 (s, 1H), 8.02 (d, 1H), 8.12 (d, 1H); MS m/z: 615.1 (M⁺ + 1).

Example 123

Synthesis of 1-{5-[3-(aminosulfonyl)phenyl]-6-(4-fluorophenyl)-2-(trifluoro methyl)pyrimidin-4-yl}piperidine-4-carboxylic acid

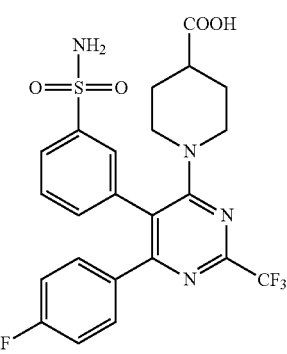 [SMILES: NS(=O)(=O)c1cccc(-c2c(-c3ccc(F)cc3)nc(C(F)(F)F)nc2N2CCC(C(=O)O)CC2)c1]

A solution of ethyl 1-{5-[3-(aminosulfonyl)phenyl]-6-(4-fluorophenyl)-2-(trifluoromethyl)pyrimidin-4-yl}piperidine-4-carboxylate (0.4 g, 0.725 mmol) in tetrahydrofuran (4 ml) was treated with lithium hydroxide monohydrate (0.036 g, 0.87 mmol) in water (0.2 ml) and was stirred for 17 hours. Subsequently the reaction mixture was poured onto ice-cold water, acidified with dilute hydrochloric acid and extracted with dichloromethane (25 ml). Evaporation of organic layer furnished the required product. ¹H-NMR (DMSO-d₆) δ: 1.39 (m, 2H), 1.64 (m, 2H), 2.09 (m, 1H), 2.84-2.89 (m, 2H), 3.66 (m, 2H), 7.02-7.07 (m, 2H), 7.07-7.13 (m, 2H), 7.37-7.39 (m, 2H), 7.49-7.53 (m, 1H), 7.69 (s, 1H), 7.72-7.74 (d, 1H), 12.25 (br, 1H, D₂O exchangeable); MS m/z: 525.0 (M⁺+1).

Example 124

Synthesis of 4-[4-(methoxyaminocarbonyl)piperidin-1-yl}-5-(4-fluoro phenyl)-6-[4-(methylsulfonyl)phenyl]-2-(trifluoromethyl)pyrimidine

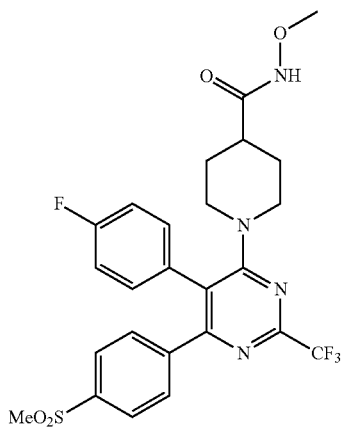 [SMILES: CONC(=O)C1CCN(c2nc(C(F)(F)F)nc(-c3ccc(S(C)(=O)=O)cc3)c2-c2ccc(F)cc2)CC1]

A solution of 1-{5-(4-fluorophenyl)-6-[4-(methylsulfonyl)phenyl]-2-(trifluoromethyl)pyrimidin-4-yl}piperidine-4-carboxylic acid (0.15 g, 0.30 mmol) in dichloromethane (5 ml) was treated with o-methyl hydroxylamine hydrochloride (0.028 g, 0.30 mmol), 1-(3-dimethylaminopropyl)-3-ethyl-carbodiimide hydrochloride (0.127 g, 0.663 mmol), 1-hydroxybenzotriazole (0.008 g, 0.066 mmol) and diisopropylethylamine (0.042 g, 0.33 mmol). After 2 hours of stirring the reaction mixture was poured onto ice-cold water, extracted with dichloromethane and washed with brine. Evaporation of the organic layer furnished the required compound. ¹H-NMR (DMSO-d₆) δ: 1.46 (m, 4H), 2.14 (m, 1H), 2.73-2.78 (m, 2H), 3.18 (s, 3H), 3.53 (s, 3H), 3.81-3.84 (m, 2H), 7.24 (d, 2H), 7.31-7.36 (m, 5H), 7.75 (d, 2H), 11.01 (br.s, 1H, D₂O exchangeable); MS m/z: 535.1 (M⁺+1).

The following compound was prepared according to the above-mentioned procedure

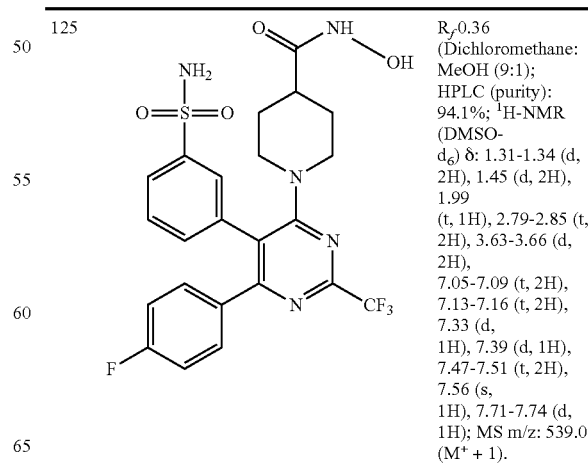

125

R_f 0.36 (Dichloromethane: MeOH (9:1); HPLC (purity): 94.1%; ¹H-NMR (DMSO-d₆) δ: 1.31-1.34 (d, 2H), 1.45 (d, 2H), 1.99 (t, 1H), 2.79-2.85 (t, 2H), 3.63-3.66 (d, 2H), 7.05-7.09 (t, 2H), 7.13-7.16 (t, 2H), 7.33 (d, 1H), 7.39 (d, 1H), 7.47-7.51 (t, 2H), 7.56 (s, 1H), 7.71-7.74 (d, 1H); MS m/z: 539.0 (M⁺ + 1).

Example 126

Synthesis of methyl 3-methoxy-4-({6-[4-(methylsulfonyl)phenyl]-5-(4-fluorophenyl)-2-(trifluoromethyl)pyrimidin-4-yl}oxy)benzoate

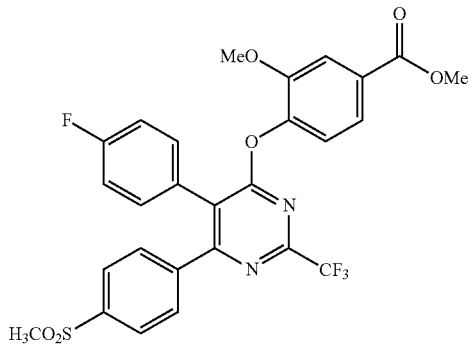

4-Chloro-5-(4-fluorophenyl)-6-[4-(methylsulfonyl)phenyl]-2-(trifluoro methyl)pyrimidine (0.5 g, 1.63 mmol), methyl vanillate (0.423 g, 2.33 mmol), potassium carbonate (0.24 g, 1.74 mmol) and acetonitrile (7 ml) were stirred at room temperature for 2 hours and subsequently the reaction mixture was refluxed for 6 hours. Further, potassium carbonate (0.08 g, 0.58 mmol) and vanillic ester (0.12 g, 0.66 mmol) were added to the reaction mixture and the refluxing was continued for another 4 hours. Subsequently the reaction mixture was poured onto ice-cold water, extracted with ethyl acetate (25 mL) and washed with brine solution. Evaporation of the organic layer yielded the required product. $^1$H-NMR (DMSO-$d_6$) δ: 3.24 (s, 3H), 3.81 (s, 3H), 3.88 (s, 3H), 7.26-7.30 (m, 2H), 7.44 (d, 1H), 7.49-7.53 (m, 2H), 7.61-7.69 (m, 4H), 7.91 (d, 2H); MS m/z: 576.8 (M$^+$+1).

Example 127

Synthesis of 3-methoxy-4-({6-(4-fluorophenyl)-5-[3-(aminosulfonyl)phenyl]-2-(trifluoromethyl)pyrimidin-4-yl}oxy)-N-methoxybenzamide

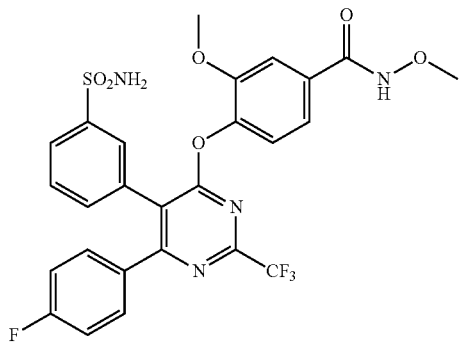 [SMILES: CONC(=O)c1ccc(Oc2nc(C(F)(F)F)nc(-c3ccc(F)cc3)c2-c2cccc(S(N)(=O)=O)c2)c(OC)c1]

Step 1

Preparation of 4-hydroxy-N-3-dimethoxybenzamide

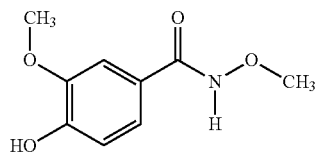

Vanillic acid (1.0 g, 5.93 mmol), o-methylhydroxylamine (0.5 g, 5.99 mmol), 1-(3-dimethylaminopropyl)-3-ethylcarbodiimide hydrochloride (1.37 g, 7.12 mmol), 1-hydroxybenzotriazole (0.095 g, 0.713 mmol) and diisopropylethylamine (0.76 g, 5.93 mmol) in dichloromethane (8 ml) were stirred for 2 hours. Subsequently the reaction mixture was poured onto cold water and extracted with dichloromethane (50 ml). The crude material obtained on evaporation of the organic layer was purified by column chromatography; elution with 1.5% MeOH in dichloromethane yielded the pure compound.

Step 2

Preparation of 3-methoxy-4-({6-(4-fluorophenyl)-5-[3-(aminosulfonyl)phenyl]-2-(trifluoromethyl)pyrimidin-4-yl}oxy)-N-methoxybenzamide

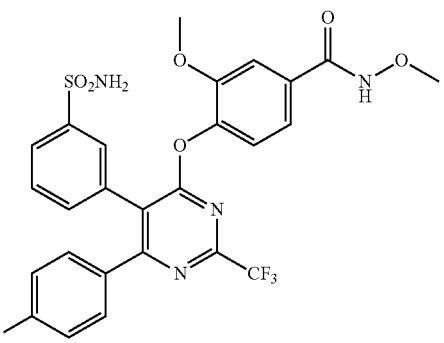

A suspension of 3-[4-chloro-6-(4-fluorophenyl)-2-(trifluoromethyl)pyrimidin-5-yl]benzenesulfonamide (0.15 g, 0.35 mmol), 4-hydroxy-N,3-dimethoxybenzamide (0.102 g, 0.52 mmol) and potassium carbonate (0.52 mmol) in acetonitrile (3 ml) were heated to reflux (65° C.) for 2 hours. Subsequently the reaction mixture was poured onto ice-cold water, extracted with dichloromethane (50 ml) and washed with brine. Evaporation of the organic layer furnished a crude material, which was purified by column chromatography; elution with 2% MeOH in dichloromethane furnished the required compound. $^1$H-NMR (DMSO-$d_6$) δ: 3.73 (s, 3H), 3.79 (s, 3H), 7.16-7.20 (m, 2H), 7.37 (d, 1H), 7.41-7.45 (m, 5H), 7.53 (s, 1H), 7.62-7.63 (d, 2H), 7.85 (d, 1H), 7.89 (s, 1H). 11.9 (s, 1H); MS m/z: 593 (M$^+$+1).

The following compound was made by the above-mentioned procedure

| 128 | 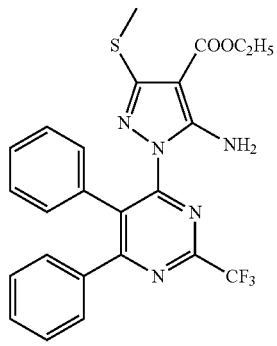 | ¹H-NMR (DMSO-d₆) δ: 3.24 (s, 3H), 3.73 (s, 3H), 3.79 (s, 3H), 7.26-7.30 (m, 2H), 7.36-7.39 (m, 1H), 7.42 (s, 1H), 7.49 (d, 2H), 7.51-7.54 (m, 2H), 7.61-7.63 (m, 1H), 7.90 (d, 2H), 11.85 (br, 1H, D₂O exchangeable); MS m/z: 592 (M⁺ + 1). |
|---|---|---|

Example 129

Synthesis of 5-amino-1-[5,6-diphenyl-2-(trifluoromethyl)pyrimidin-4-yl]-3-methyl-1H-pyrazole-4-carbonitrile

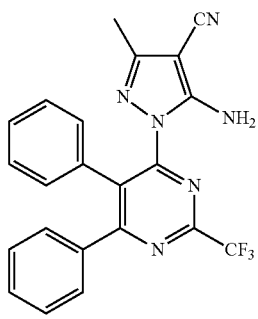 [SMILES: Cc1nn(-c2nc(C(F)(F)F)nc(-c3ccccc3)c2-c2ccccc2)c(N)c1C#N]

1-Methoxyethylidene malononitrile (0.17 g, 1.36 mmol) (prepared from malononitrile and triethyl orthoacetate by heating with acetic anhydride) was heated with 4-hydrazino-5,6-diphenyl-2-(trifluoromethyl)pyrimidine (0.15 g, 0.45 mmol) in methanol (6 ml), overnight at 60-65° C. The solid that separated out from the reaction mixture was filtered and washed with methanol (5 ml), to yield the title compound. ¹H-NMR (DMSO-d₆) δ: 1.97 (s, 3H), 6.97 (br, 2H, D₂O exchangeable), 7.07 (d, 2H), 7.26-7.38 (m, 7H), 7.40-7.41 (m, 1H); MS m/z: 421.1 (M⁺+1).

Example 130

Synthesis of ethyl 5-amino-1-[5,6-diphenyl-2-(trifluoromethyl)pyrimidin-4-yl]-3-(methylthio)-1H-pyrazole-4-carboxylate Ethyl 2-cyano-3,3-bis(methylthio)acrylate (0.3 g, 1.36 mmol) was heated with 4-hydrazino-5,6-diphenyl-2-(trifluoromethyl)pyrimidine (0.15 g, 0.45 mmol) in methanol (6 ml) overnight at 60-65° C. The solid that separated out from the reaction mixture was filtered and washed with isopropylalcohol (5 ml), to furnish the required compound. ¹H-NMR (DMSO-d₆) δ: 1.22-1.25 (t, 3H), 3.16 (s, 3H), 4.11-4.17 (q, 2H), 4.36 (br, 2H, D₂O exchangeable), 7.12 (d, 2H), 7.25-7.35 (m, 7H), 7.69 (d, 1H); MS m/z: 500.1 (M⁺+1).

The following compounds were prepared according to the procedure described above.

| Ex. | Structure | Analytical Data |
|---|---|---|
| 131 | (structure) | ¹H-NMR (CDCl₃) δ: 6.11 (s, 1H), 6.99-7.01 (d, 2H), 7.23-7.35 (d, 8H); MS m/z: 407.1 (M⁺ + 1). |
| 132 | (structure) | ¹H-NMR (CDCl₃) δ: 0.86 (s, 9H), 5.21 (br, 2H, D₂O exchangeable), 5.35 (s, 1H), 7.00-7.03 (d, 2H), 7.19-7.29 (m, 8H); MS m/z: 438.1 (M⁺ + 1). |

| Ex. | Structure | Analytical Data |
|---|---|---|
| 133 | 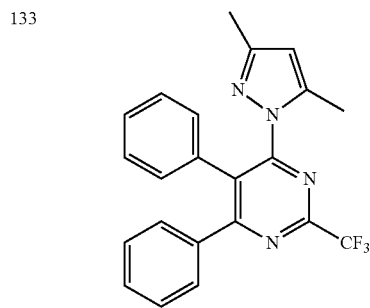 | $^1$H-NMR (CDCl$_3$) δ: 2.04 (s, 3H), 2.21 (s, 3H), 5.85 (s, 1H), 6.94 (d, 2H), 7.18-7.32 (m, 6H), 7.35 (d, 2H); MS m/z: 395.1 (M$^+$ + 1). |
| 134 | 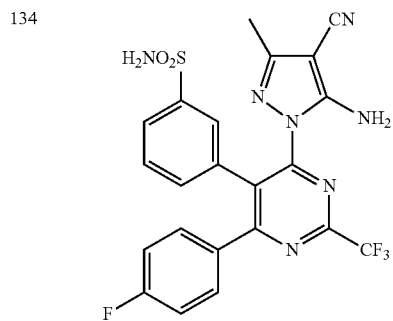 | $^1$H-NMR (CDCl$_3$) δ: 1.86 (s, 3H), 6.44 (s, 2H), 6.93-6.98 (m, 2H), 7.20-7.29 (m, 4H), 7.40-7.44 (m, 1H), 7.66 (s, 1H), 7.83-7.88 (m, 1H); MS m/z: 518.0 (M$^+$ + 1). |
| 135 | 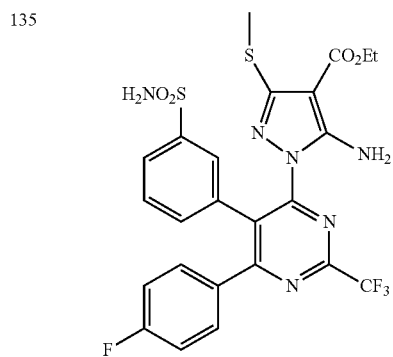 | $^1$H-NMR (CDCl$_3$) δ: 1.33-1.35 (t, 3H), 1.56 (s, 3H), 4.27-4.32 (m, 2H), 6.92-6.96 (m, 2H), 7.18-7.20 (m, 2H), 7.37-7.47 (m, 2H), 7.66 (s, 1H), 7.81-7.84 (m, 1H); MS m/z: 599.0 (M$^+$ + 1). |
| 136 | 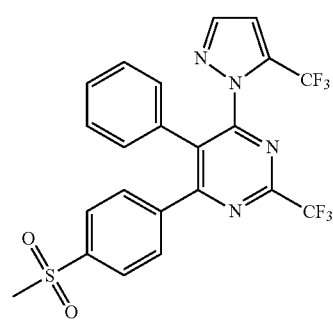 [SMILES: CS(=O)(=O)c1ccc(-c2nc(C(F)(F)F)nc(-n3nccc3C(F)(F)F)c2-c2ccccc2)cc1] | $^1$H-NMR (CDCl$_3$) δ: 3.02 (s, 3H), 6.63 (s, 1H), 7.02 (d, 2H), 7.29-7.31 (m, 2H), 7.35 (m, 1H), 7.55 (d, 2H), 7.83 (d, 2H), 8.40 (s, 1H); MS m/z: 513.0 (M$^+$ + 1). |
| 137 | 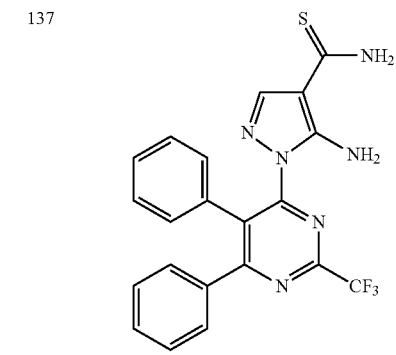 | $^1$H-NMR (CDCl$_3$) δ: 6.56 (bs, 2H), 7.00 (d, 2H), 7.22-7.34 (m, 5H), 8.28 (s, 2H); MS m/z: 441.0 (M$^+$ + 1). |
| 138 | 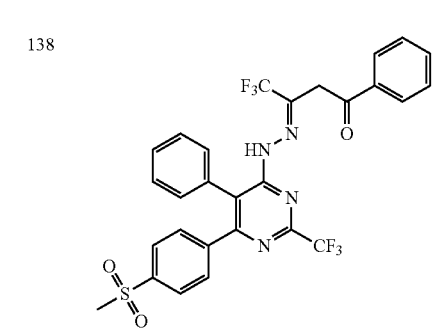 | $^1$H-NMR (CDCl$_3$) δ: 3.00 (s, 3H), 3.54 (q, 2H), 6.42 (d, 2H), 6.84 (d, 1H), 7.00-7.05 (m, 1H), 7.20-7.24 (m, 2H), 7.31-7.33 (m, 2H), 7.45-7.51 (m, 3H), 7.77-7.81 (m, 2H), 7.96 (d, 2H); MS m/z: 607.0 (M$^+$ + 1). |
| 139 | 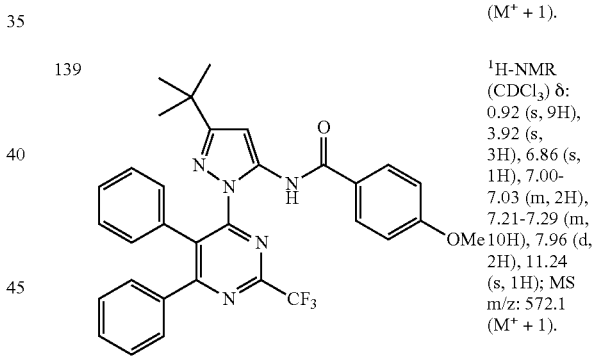 | $^1$H-NMR (CDCl$_3$) δ: 0.92 (s, 9H), 3.92 (s, 3H), 6.86 (s, 1H), 7.00-7.03 (m, 2H), 7.21-7.29 (m, 10H), 7.96 (d, 2H), 11.24 (s, 1H); MS m/z: 572.1 (M$^+$ + 1). |
| 140 | 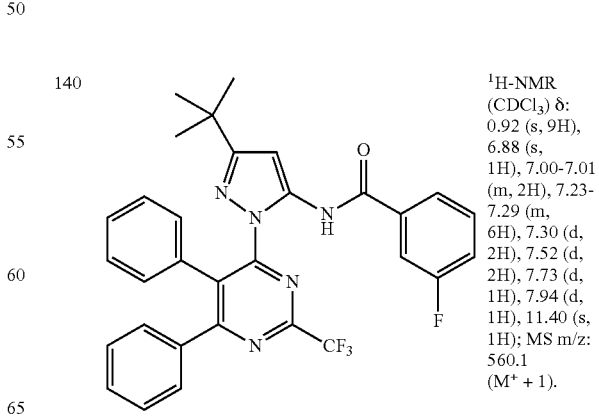 | $^1$H-NMR (CDCl$_3$) δ: 0.92 (s, 9H), 6.88 (s, 1H), 7.00-7.01 (m, 2H), 7.23-7.29 (m, 6H), 7.30 (d, 2H), 7.52 (d, 2H), 7.73 (d, 1H), 7.94 (d, 1H), 11.40 (s, 1H); MS m/z: 560.1 (M$^+$ + 1). |

101
-continued

| Ex. | Structure | Analytical Data |
|---|---|---|
| 141 | 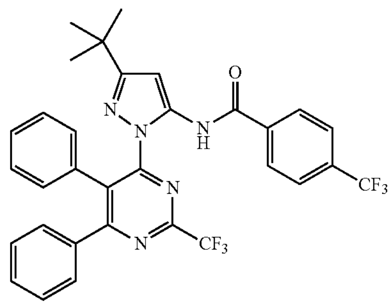 [SMILES: CC(C)(C)c1cc(NC(=O)c2ccc(C(F)(F)F)cc2)n(-c2nc(C(F)(F)F)nc(-c3ccccc3)c2-c2ccccc2)n1] | ¹H-NMR (CDCl₃) δ: 0.92 (s, 9H), 6.91 (s, 1H), 7.01-7.03 (m, 2H), 7.23-7.31 (m, 8H), 7.81 (d, 2H), 8.10 (d, 2H), 11.52 (s, 1H); MS m/z: 610.1 (M⁺ + 1). |
| 142 | 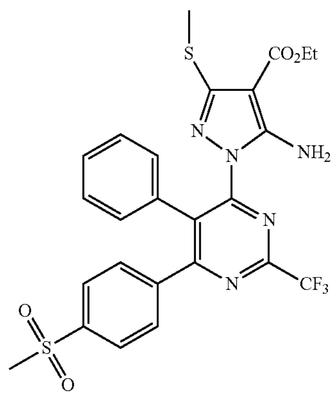 [SMILES: CCOC(=O)c1c(SC)nn(-c2nc(C(F)(F)F)nc(-c3ccc(S(C)(=O)=O)cc3)c2-c2ccccc2)c1N] | ¹H-NMR (CDCl₃) δ: 1.35 (t, 3H), 1.59 (s, 3H), 3.01 (s, 3H), 4.27-4.32 (dd, 2H), 7.02 (s, 2H), 7.38-7.41 (m, 5H), 7.78-7.81 (m, 2H); MS m/z: 578.0 (M⁺ + 1). |

Example 143

Synthesis of 5-amino-1-[5,6-diphenyl-2-(trifluoromethyl)pyrimidin-4-yl]-3-(methylthio)-N-phenyl-1H-pyrazole-4-carboxamide

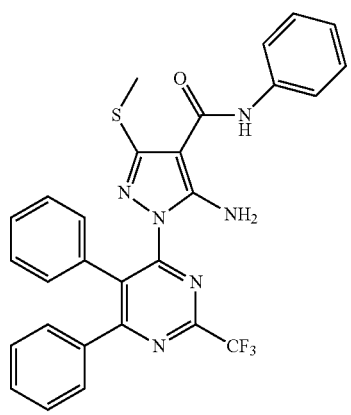 [SMILES: CSc1nn(-c2nc(C(F)(F)F)nc(-c3ccccc3)c2-c2ccccc2)c(N)c1C(=O)Nc1ccccc1]

Step 1

Preparation of 2-cyano-3,3-bis(methylthio)-N-phenylacrylamide

2-Cyano-N-phenylacetamide (1.0 g, 6.25 mmol) was treated with sodium hydride 60% (1.13 g, 28.13 mmol) in tetrahydrofuran under ice-cold conditions and stirring for 15 minutes. Carbon disulfide (0.9 mL, 15.65 mmol) was added to the above mixture and the stirring was continued at ice-cold condition for a further 15 minutes. Methyliodide (2.22 g, 15.65 mmol) was added to the above under the same ice-cold conditions and the stirring was continued at room temperature overnight. Subsequently the reaction mixture was acidified with dilute hydrochloric acid (5 ml) and extracted with ethyl acetate (50 ml). Evaporation of the organic layer yielded an oily crude material.

Step 2

Preparation of 5-amino-1-[5,6-diphenyl-2-(trifluoromethyl)pyrimidin-4-yl]-3-(methylthio)-N-phenyl-1H-pyrazole-4-carboxamide

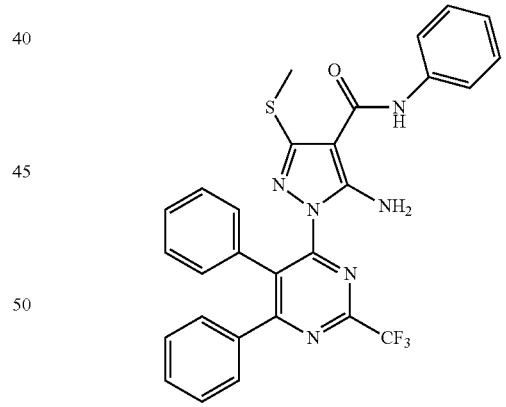

A solution of 4-hydrazino-5,6-diphenyl-2-(trifluoromethyl)pyrimidine (0.2 g, 0.63 mmol) in methanol (6 ml) was heated with 2-cyano-3,3-bis(methylthio)-N-phenylacrylamide (0.5 g, 1.89 mmol), overnight, at 60-65° C. The solid that separated out was filtered and washed with isopropyl alcohol (3 ml) to yield the required product. ¹H-NMR (CDCl₃) δ: 1.98 (s, 3H), 6.96-7.57 (m, 15H), 7.25-7.30 (2H, D₂O exchangeable), 8.86 (br, 1H, D₂O exchangeable); MS m/z: 547.1 (M⁺+1).

The following compound was made by the procedure mentioned above

| 144 | 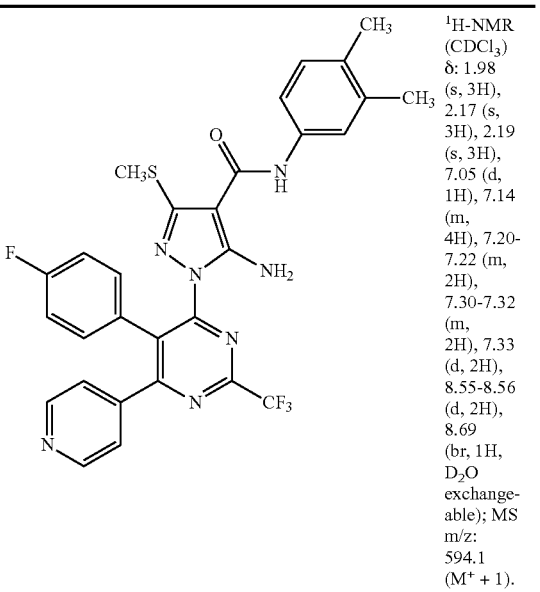 | ¹H-NMR (CDCl₃) δ: 1.98 (s, 3H), 2.17 (s, 3H), 2.19 (s, 3H), 7.05 (d, 1H), 7.14 (m, 4H), 7.20-7.22 (m, 2H), 7.30-7.32 (m, 2H), 7.33 (d, 2H), 8.55-8.56 (d, 2H), 8.69 (br, 1H, D₂O exchangeable); MS m/z: 594.1 (M⁺ + 1). |
|---|---|---|

Example 145

Synthesis of 1-(2,6-dichlorophenyl)-3-{1-[5,6-diphenyl-2-(trifluoromethyl)pyrimidin-4-yl]-3-t-butyl-1H-pyrazol-5-yl}urea

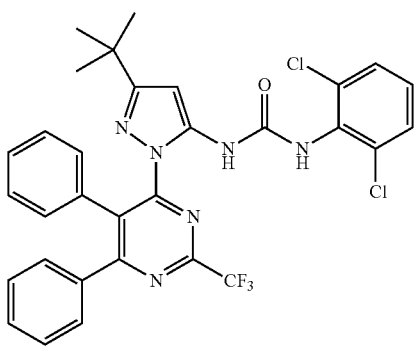 [SMILES: CC(C)(C)c1cc(NC(=O)Nc2c(Cl)cccc2Cl)n(-c2nc(C(F)(F)F)nc(-c3ccccc3)c2-c2ccccc2)n1]

The solution of 3-t-butyl-1-[5,6-diphenyl-2-(trifluoromethyl)pyrimidin-4-yl]-1H-pyrazol-5-amine (0.23 mmol) in dichloromethane (3 ml) was treated with 2,6-dichlorophenyl isocyanate (0.056 g, 0.3 mmol) in the presence of triethylamine (0.05 ml), and the reaction was mixture was stirred at room temperature, overnight. Subsequently water (15 ml) was added to above and it was extracted with ethyl acetate (25 ml). The organic layer was evaporated and the crude material purified by column chromatography; elution with 1.5% of ethyl acetate in hexane yielded the title compound. ¹H-NMR (CDCl₃) δ: 0.86 (s, 9H), 6.58 (s, 1H), 7.02-7.05 (m, 3H), 7.14 (d, 2H), 7.24-7.33 (m, 8H), 8.43-8.44 (br, 1H, D₂O exchangeable), 10.52 (br, 1H, D₂O exchangeable); MS m/z: 625 (M⁺).

Example 146

Synthesis of 4-[4-(methylthio)phenyl]-5,6-diphenyl-2-(trifluoromethyl)pyrimidine

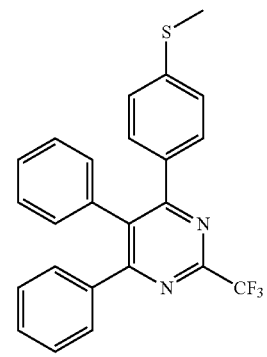 [SMILES: CSc1ccc(-c2nc(C(F)(F)F)nc(-c3ccccc3)c2-c2ccccc2)cc1]

4-Chloro-5,6-diphenyl-2-(trifluoromethyl)pyrimidine (0.2 g, 0.6 mmol, prepared according to the procedure described in PCT/IB03/02879) was heated to reflux with tetra-kis triphenyl palladium (0) (0.068 g, 0.058 mmol), aqueous solution of potassium carbonate (0.16 g in 0.16 ml water), 4-(methylthio)benzene boronic acid (0.168 g, 1 mmol) and toluene (20 ml) under a nitrogen atmosphere overnight. The reaction mixture was acidified with dilute hydrochloric acid 10 ml and extracted with ethyl acetate. The organic layer was concentrated; the crude material obtained was triturated with ether and filtered to yield the title compound. ¹H-NMR (DMSO-d₆) δ: 2.45 (s, 3H), 7.13-7.15 (m, 4H), 7.23-7.34 (m, 8H), 7.61 (d, 2H); MS m/z: 423.1 (M⁺+1).

The following compound was prepared by the above-mentioned procedure

| 147 | 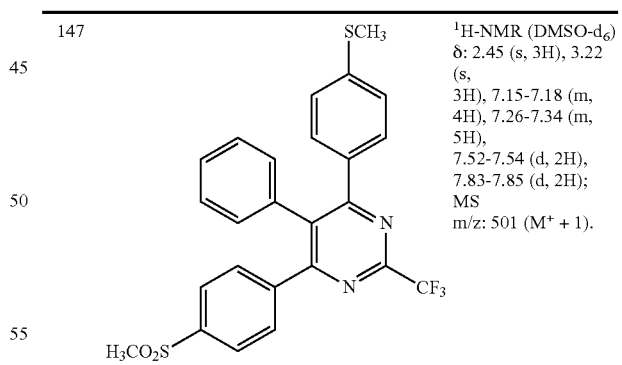 | ¹H-NMR (DMSO-d₆) δ: 2.45 (s, 3H), 3.22 (s, 3H), 7.15-7.18 (m, 4H), 7.26-7.34 (m, 5H), 7.52-7.54 (d, 2H), 7.83-7.85 (d, 2H); MS m/z: 501 (M⁺ + 1). |
|---|---|---|

Described below are the pharmacological assays used for finding out the efficacy of the compounds of the present invention.

In vitro Evaluation of Cyclooxygenase-2 (COX-2) Inhibition Activity

The compounds of this invention exhibited in vitro inhibition of COX-2. The COX-2 inhibition activities of the compounds illustrated in the examples were determined by the following method.

Human Whole Blood Assay

Human whole blood provides a protein and cell rich milieu appropriate for the study of the biochemical efficacy of anti-inflammatory compounds such as selective COX-2 inhibitors. Studies have shown that normal human blood does not contain the COX-2 enzyme. This correlates with the observation that COX-2 inhibitors have no effect on prostaglandin $E_2$ ($PGE_2$) production in normal blood. These inhibitors were active only after incubation of human blood with lipopolysaccharide (LPS), which induces COX-2 production in the blood.

Fresh blood was collected in tubes containing sodium heparin by vein puncture from healthy male volunteers. The subjects should have no apparent inflammatory conditions and should have not taken NSAIDs for at least 7 days prior to blood collection. Blood was preincubated with aspirin in vitro (12 μg/ml, at time zero) to inactivate COX-1 for 6 hours. Then test compounds (at various concentrations) or vehicle were added to blood, the blood was stimulated with LPS B:4 (10 μg/ml) and incubated for another 18 hours at 37° C. water bath. After which the blood was centrifuged, plasma was separated and stored at −80° C. (J. Pharmacol. Exp. Ther, 271, 1705, 1994; Proc. Natl. Acad. Sci. USA, 96, 7563, 1999). The plasma was assayed for $PGE_2$ using Cayman ELISA kit as per the procedure outlined by the manufacturer (Cayman Chemicals, Ann Arbor, USA). Representative results of PGE-2 inhibition are shown in the Table I.

TABLE I

| | % PGE-2 Inhibition in hWBA | | |
|---|---|---|---|
| Ex. | 0.25 μM | 1 μM | 10 μM |
| 4 | 6.10 | 22.85 | 35.63 |
| 7 | 26.17 | 1.90 | NA |
| 22 | 15.64 | 20.40 | 36.37 |

Wherein, NA indicates No activity and ND indicates Not Done.

COX-1 and COX-2 Enzyme Based Assay

COX-1 and COX-2 enzyme based assays were carried out to check the inhibitory potential of the test compounds on the production of prostaglandin by purified recombinant COX-1/COX-2 enzyme (Proc. Nat. Acad. Sci. USA, 88, 2692-2696, 1991; J. Clin. Immunoassay 15, 116-120, 1992). In this assay, the potential of the test compound to inhibit the production of prostaglandin either by COX-1 or COX-2 from arachidonic acid (substrate) was measured. This was an enzyme based in-vitro assay to evaluate selective COX inhibition with good reproducibility.

Arachidonic acid was converted to $PGH_2$ (Intermediate product) by COX1/COX-2 in the presence or absence of the test compound. The reaction was carried out at 37° C. and after 2 minutes it was stopped by adding 1M HCl. Intermediate product $PGH_2$ was converted to a stable prostanoid product $PGF_{2\alpha}$ by $SnCl_2$ reduction. The amount of $PGF_{2\alpha}$ produced in the reaction was inversely proportional to the COX inhibitory potential of the test compound. The prostanoid product was quantified via enzyme immunoassay (EIA) using a broadly specific antibody that binds to all the major forms of prostaglandin, using Cayman ELISA kit as per the procedure outlined by the manufacturer (Cayman Chemicals, Ann Arbor, USA). Representative results of inhibition are shown in the Table II.

TABLE II

| | % Inhibition in rEnzyme Assay | | | |
|---|---|---|---|---|
| | COX-1 | | COX-2 | |
| Ex. | 1 μM | 10 μM | 1 μM | 10 μM |
| 2 | 33.84 | 50.41 | 17.31 | 48.9 |
| 51 | 8.27 | 7.1 | NA | 12.29 |
| 53 | 46.29 | 56.85 | 20.04 | 26.70 |
| 54 | 34.42 | 45.53 | NA | 13.71 |
| 57 | NA | 5.7 | 8.29 | 0.66 |
| 58 | 10.22 | 9.59 | 11.24 | 2.62 |
| 59 | — | 32 | — | 31 |
| 80 | — | NA | — | 20 |
| 116 | 6.29 | 19.24 | NA | 7.03 |

In Vitro Measurement of TNF-α in Human Peripheral Blood Mononuclear Cells

This assay determines the effect of test compounds on the production of TNF α in human Peripheral Blood Mononuclear Cells (PBMC). Compounds were tested for their ability to inhibit the activity of TNF α in human PBMC. PBMC were isolated from blood (of healthy volunteers) using BD Vacutainer CPT™ (Cell preparation tube, BD Bio Science) and suspended in RPMI medium (Physiol. Res. 52, 593-598, 2003). The test compounds were pre-incubated with PBMC (0.5 million/incubation well) for 15 minutes at 37° C. and then stimulated with Lipopolysaccharide (*Escherichia coli*: B4; 1 μg/ml) for 18 hours at 37° C. in 5% $CO_2$. The levels of TNF-α in the cell culture medium were estimated using enzyme-linked immunosorbent assay performed in a 96 well format as per the procedure of the manufacturer (Cayman Chemical, Ann Arbor, USA). Representative results of TNF-α inhibition are shown in the Table IIIa.

TABLE IIIa

| | TNF-α Inhibition (%) at | |
|---|---|---|
| Ex. | Conc. (1 μM) | Conc. (10 μM) |
| 4 | 29.98 | 107.36 |
| 5 | 35.86 | 56.34 |
| 11 | 12.71 | 50.71 |
| 12 | 34.81 | 78.42 |
| 13 | 25.77 | 35.27 |
| 14 | 25.47 | 67.54 |
| 24 | 53.86 | 32.91 |
| 25 | 38.77 | 94.02 |
| 26 | 32.70 | 50.79 |
| 27 | 43.49 | 51.92 |
| 30 | 43.23 | 100 |
| 31 | 37.39 | 62.48 |
| 34 | NA | 80.88 |
| 35 | 17.13 | 86.57 |
| 36 | 51.26 | 26.92 |
| 55 | 81.46 | 91.61 |
| 57 | 84.50 | 88.86 |
| 59 | 87 | 92 |
| 80 | 50 | 78 |
| 98 | 94.1 | 94.6 |
| 116 | 37.84 | 58.28 |
| 66 | 57.85 | 80.68 |
| 118 | 69.71 | 86.49 |
| 120 | 88.92 | 91.50 |
| 158 | 33.5 | 91.31 |

In vitro Measurement of TNF-α in Human Whole Blood

This assay determines the effect of test compounds on the production of TNF-α in human whole blood. Compounds were tested for their ability to inhibit the activity of TNF-α in whole blood.

Heparanised blood from a healthy human volunteer was collected and diluted with RPMI 1640 incomplete medium (1:5 dilution). Diluted blood was aliquoted into 96 well plate 170 ul/well immediately. 20 ul of the drug of different concentrations was added to the respective wells with a control. The plate was incubated in 37° C. thermo mixer at 400 rpm for 60-70 minutes. After the incubation 10 ul of the LPS (from *E. coli* B4) was added to get the final concentration of 1 ug/well. The plate was again incubated in the 37° C. thermo mixer at 400 rpm 120 minutes in the thermo mixer and then left in the 37° C. $CO_2$ incubator for two more hours so that the total stimulation time is four hours. The plasma was collected carefully without disturbing the pellet at the bottom and stored at −20° C. Then TNF-α levels were estimated using the R&D systems ELISA kit duoset kit (DY210). Representative results of TNF-α inhibition are shown in the Table IIIb.

TABLE IIIb

| Ex. | TNF-α Inhibition (%) at | |
|---|---|---|
| | Conc. (1 μM) | Conc. (10 μM) |
| 98 | 40.6 | 62.0 |

In vitro Measurement of Interleukin-6 (IL-6)

This assay determines the effect of test compounds on the production of IL-6 in human PBMC (Physiol. Res. 52, 593-598, 2003). Compounds were tested for their ability to inhibit the activity of IL-6 in human PBMC. PBMC were isolated from blood using BD Vacutainer CPT™ Cell preparation tube (BD Bio Science) and suspended in RPMI medium. The test compounds were pre-incubated with PBMC (0.5 million/incubation well) for 15 minutes at 37° C. and then stimulated with Lipopolysaccharide (*Escherichia coli*: B4; 1 μg/ml) for 18 hours at 37° C. in 5% $CO_2$. The levels of IL-6 in cell culture medium were estimated using enzyme-linked immunosorbent assay performed in a 96 well format as per the procedure of the manufacturer (Cayman Chemical, Ann Arbor, USA). Representative results of inhibition are shown in the Table IV.

TABLE IV

| Ex. | IL-6 Inhibition (%) | |
|---|---|---|
| | Conc. (1 μM) | Conc. (10 μM) |
| 4 | 27.17 | 100 |
| 18 | 32.83 | 41.04 |
| 19 | 27.88 | 41.91 |
| 59 | 26.14 | 36.82 |
| 61 | 24.51 | 54.49 |
| 78 | 22.28 | 25.26 |
| 80 | — | NA |
| 158 | — | 65.71 |

TABLE V

| Ex. | IL-12 Inhibition (%) | |
|---|---|---|
| | Conc. (1 μM) | Conc. (10 μM) |
| 158 | 69.03 | 98.26 |

Carrageenan Induced Paw Edema Test in Rat

The carrageenan paw edema test was performed as described by Winter et al (Proc. Soc. Exp. Biol. Med, 111, 544, 1962). Male wistar rats were selected with body weights equivalent within each group. The rats were fasted for 18 hours with free access to water. The rats were dosed orally with the test compound suspended in the vehicle containing 0.25% carboxymethylcellulose and 0.5% Tween 80. The control rats were administered with vehicle alone. After an hour, the rats were injected with 0.1 ml of 1% Carrageenan solution in 0.9% saline into the sub-plantar surface of the right hind paw. Paw volume was measured using digital plethysmograph before and after 3 hours of carrageenan injection. The average of foot swelling in drug treated animals was compared with that of the control animals. Anti-inflammatory activity was expressed as the percentage inhibition of edema compared with control group (Arzneim-Forsch/Drug Res., 43 (I), 1, 44-50, 1993); Representative results of edema inhibition are shown in the Table VI.

TABLE VI

| Ex. | Inhibition of edema (%) at 5 mg/kg |
|---|---|
| 4 | 17.12 |
| 5 | 14.5 |

Ulcerogenic Potential

In order to evaluate the compound's role on the ulcer formation, the animals were sacrificed and the stomach was taken out and flushed with 1% formalin. Animals (male wistar 200 g) were fasted for 18 hours with free access to water and the test compounds were suspended in 0.5% Tween 80 and 0.25% CMC (carboxymethylcellulose) solution to make a uniform suspension. After 4 hours of oral administration of test compounds, all the animals were sacrificed by cervical dislocation. The stomach was dissected carefully and filled up with a sterile saline solution and embedded in 6% formalin solution. Finally the stomach was cut longitudinally and ulcer lesions were observed with computerized stereomicroscope. The test compound treated groups were compared with the vehicle treated groups. Doses selected: 50, 100, 200 mg/kg (Marco Romano et al, Journal of clinical Investigation, 1992; 2409-2421.) Representative results of ulcer incidence are shown in the Table VII

TABLE VII

| Ex. | Ulcer incidence at 5 mg/kg |
|---|---|
| 4 | Nil |
| 5 | Nil |

Inhibitory Action on Adjuvant Arthritis in Rats

Compounds were assayed for their activity on rat adjuvant induced arthritis model according to Theisen-Popp et al., (Agents Actions, 42, 50-55, 1994). 6 to 7 weeks old, wistar rats were weighed, marked and assigned to groups [a negative control group in which arthritis was not induced (non-adjuvant control), a vehicle-treated arthritis control group, test substance treated arthritis group]. Adjuvant induced arthritis was induced by an injection of 0.1 ml of *Mycobacterium butyricum* (Difco) suspended in mineral oil (5 mg/ml) into the sub-plantar region of the right hind paw (J. Pharmacol. Exp. Ther., 284, 714, 1998). Body weight, and paw volumes were measured at various days (0, 4, 14, 21) for all the groups. The test compound or vehicle was administered orally, beginning post injection of adjuvant ('0' day) and continued for 21 days (pre-treatment group). In the post-treatment group, the test compound or vehicle was administered starting from day $14^{th}$ to $21^{st}$ day. On day 21, body weight and paw volume of both right and left hind paws were taken. Spleen, and thymus weights were determined. In addition, the radiographs of both hind paws were taken to assess the tibio-tarsal joint integrity. Hind limb below the stifle joint was removed and fixed in 1% formalin saline for the histopathological assessment. At the end of the experiment, serum samples were analysed for inflammatory mediators. The presence or absence of lesions in the stomach was also observed.

Two-factor ('treatment' and 'time') analysis of variance with repeated measures on 'time' was applied to the percentage (%) changes for body weight and foot volumes. A post hoc Dunnett's test was conducted to compare the effect of treatments to vehicle control. A one-way analysis of variance was applied to the thymus and spleen weights followed by the Dunnett's test to compare the effect of treatments to vehicle. Dose-response curves for percentage inhibition in foot volumes on days 4, 14 and 21 were fitted by a 4-parameter logistic function using a nonlinear least Squares regression. $IC_{50}$ was defined as the dose corresponding to a 50% reduction compared to the vehicle control and was derived by interpolation from the fitted 4-parameter equation.

LPS Induced Sepsis for Measurement of TNF-α Inhibition in Mice

The LPS induced sepsis model in mice was performed as described by Les sekut et al (J Lab Clin Med 1994; 124, 813-20). Female Swiss albino mice were selected and the body weights were equivalent within each group. The mice were fasted for 20 hours with free access to water. The mice were dosed orally with the test compound suspended in vehicle containing 0.5% Tween 80 in 0.25% Carboxy-methylcellulose sodium salt. The control mice were administered the vehicle alone. After 30 minutes of oral dosing, mice were injected with 500 μg of Lipopolysaccharide (*Escherichia coli*, LPS: B4 from Siga) in phosphate buffer saline solution into the intraperitoneal cavity of the mice. After 90 minutes of LPS administration mice were bled via retro-orbital sinus puncture. Blood samples were stored overnight at 4° C. Serum samples were collected by centrifuging the samples at 4000 rpm for 15 minutes at 4° C. Immediately the serum samples were analysed for TNF-α levels using commercially available mouse TNF-α ELISA kit (Amersham Biosciences) and assay was performed by the manufacturer instruction. Representative results of TNF-α inhibition are shown in the Table VIII.

TABLE VIII

| Ex. | TNF-α Inhibition (%) at 50 mg/kg |
|---|---|
| 4 | 38.37 |
| 30 | 84.84 |
| 35 | 59.62 |
| 53 | 70.93 |
| 54 | 63.44 |
| 57 | 52.02 |
| 59 | 87.15 |
| 80 | 82.75 |
| 116 | 54.23 |

$ED_{50}$ Measurement of TNF Alpha Inhibition in Mice Sepsis Model

TABLE IX

| Ex. | Mice Sepsis ED50 mg/kg |
|---|---|
| 80 | 2.13 |
| 98 | 0.01 |

Inhibitory Activity in IBD-DSS Model

DSS Induced colitis test was performed as described by Axelsson et al., 1998. Male Balb/c mice were selected in the age of 7-8 weeks for the study. Colitis in mice was induced by providing DSS (2%) in the drinking water from day 1 to 6. Mice were dosed from Day 1 to 6 with test compound suspended in vehicle containing 0.25% carboxymethyl cellulose and 0.5% Tween 80. The control animals received vehicle alone. Body weight and disease activity index was recorded daily during the experiment. After 6 days of treatment, animals were sacrificed; colon weight and colon length was recorded. Representative results are shown in the table X.

TABLE X

| Ex. | IBD-DSS Model % Inhibition of DAI at 50 mg/kg |
|---|---|
| 80 | 35.94 |

Inhibitory Activity in Psoriasis Model

Oxazolone induced dermatitis in mice was performed as described in the literature. Female Balb/c were selected in the age of 6-7 weeks for the study and 20-25 g. Mice were sensitized with oxazolone (15%) from Day 1 to day 6 by applying it on the shaved abdomen. Elicitation was done with oxazolone (2%) on the ear on day 7. Test compounds were applied topically on the ear 15 minutes and 6 hours post oxazolone application on day 7. 24 hours after oxazolone application, ear thickness is measured and ear were excised under anesthesia and weighed. Representative results are shown in table XI.

TABLE XI

| | Psoriasis-acute-Oxazolone induced dermatitis % inhibition | |
|---|---|---|
| Ex. | Ear Wt | Ear Thick |
| 80 | 18.9 | 19.2 |

Inhibitory Activity in Psoriasis Model

TPA induced dermatitis in mice was performed using the protocol described in Eur J Pharmacol 507, 253-259, 2005. Balb/c mice were acclimatized to laboratory conditions 5-7 days prior to the start of the experiment. They were randomly distributed to various groups based on body weight. The baseline ear thickness of the animal's both ears using thickness gauge was measured. For each animal 20 μl of that contains 2.5 μg of TPA was applied with help of micropipettor with disposable tips. Test compound was applied topically to both inner and outer surface of the both the ears i.e. left and right ear with acetone as control after 30 minutes 6 hours and 24 hours after application of TPA (20 μl). Ear thickness was measured after 6 and 24 hours in animals, while for ear weight ears were excised under anesthesia and weighed. Representative result are shown in the table

TABLE XI

| | Psoriasis-acute TPA induced dermatitis % inhibition | |
|---|---|---|
| Ex | Ear Wt | Ear thickness |
| 80 | 18.9 | 19.2 |
| 98 | 11.84 | 41.10 |

LPS Induced Neutrophilia Model for Asthma and COPD

LPS induced neutrophilia in Wistar rats was performed using the protocol described in Pulm Pharmacol & Ther 17, 3, 133-140, 2004. Male Wistar rats were acclimatized to laboratory conditions five to seven days prior to the start of the experiment. They were randomly distributed to various groups based on body weight. Except normal group all the animals were exposed to LPS 100 µg/ml for 40 min. The rats were dosed with the test compound suspended in the vehicle containing 0.25% carboxymethylcellulose before half an hour of LPS exposure. BAL was performed 4 h after LPS exposure, total cell count and DLC was done and compared with control and the standard drug. Percentage Inhibition for neutrophilia was calculated.

TABLE XII

| Ex | LPS induced neutrophilia % inhibition at 10 mg/kg |
|---|---|
| 98 | 31.73 |

Anti-Cancer Screen

Experimental drugs are screened for anti-cancer activity in three cell lines for their $GI_{50}$, TGI and $LC_{50}$ values (using 5 concentrations for each compound). The cell lines are maintained in DMEM containing 10% fetal bovine serum. 96 well microtiter plates are inoculated with cells in 100 µM for 24 hours at 37° C., 5% $CO_2$, 95% air and 100% relative humidity. 5000 HCT116 cells/well, 5000 NCIH460 cells/well, 10000 U251 cells/well and 5000 MDAMB231 cells/well are plated. A separate plate with these cell lines is also inoculated to determine cell viability before the addition of the compounds ($T_0$).

Addition of Experimental Drugs

Following 24-hour incubation, experimental drugs are added to the 96 well plates. Each plate contains one of the above cell lines and the following in triplicate: 5 different concentrations (0.01, 0.1, 1, 10 and 100 µM) of 4 different compounds, appropriate dilutions of a cytotoxic standard and control (untreated) wells. Compounds are dissolved in dimethylsulfoxide (DMSO) to make 20 mM stock solutions, on the day of drug addition and frozen at −20° C. Serial dilutions of these 20 mM stock solutions are made in complete growth medium such that 100 µL of these drug solutions in medium, of final concentrations equaling 0.01, 0.1, 1, 10 and 100 µM can be added to the cells in triplicate. Standard drugs whose anti-cancer activity has been well documented and which are regularly used are doxorubicin and SAHA.

End-Point Measurement

Cells are incubated with compounds for 48 hours followed by the addition of 10 µL 3-(4,5-Dimethyl-2-thiazolyl)-2,5-diphenyl-2H-tetrazolium (MTT) solution per well and a subsequent incubation at 37° C., 5% $CO_2$, 95% air and 100% relative humidity, protected from light. After 4 hours, well contents are aspirated carefully followed by addition of 150 µL DMSO per well. Plates are agitated to ensure solution of the formazan crystals in DMSO and absorbance read at 570 nm.

Calculation of $GI_{50}$, TGI and $LC_{50}$

Percent growth is calculated for each compound's concentration relative to the control and zero measurement wells ($T_0$; viability right before compound addition). If a test well's O.D. value is greater than the $T_0$ measurement for that cell line % Growth=(test−zero)/(control−zero)×100

If a test well's O.D. value is lower than the $T_0$ measurement for that cell line, then: % Growth=(test−zero)/zero×100

Plotting % growth versus experimental drug concentration, $GI_{50}$ is the concentration required to decrease % growth by 50%; TGI is the concentration required to decrease % growth by 100% and $LC_{50}$ is the concentration required to decrease % growth by 150%. Representative results of growth are shown in the Table XIII.

TABLE XIII

| | $GI_{50}$ (µM) | | |
|---|---|---|---|
| Ex. | DU-145 | HCT-116 | NCI-H460 |
| 2 | 3.5 | 2.5 | 8.5 |
| 4 | 1.93 | 2 | 1.65 |
| 38 | 4 | 6 | 3.75 |
| 40 | ND | 3.5 | 3.8 |
| 41 | ND | 7 | 4 |
| 44 | ND | 26 | 4.5 |
| 51 | ND | 30 | 4.0 |
| 59 | ND | >100 | 10.5 |
| 73 | ND | 9.2 | 9.0 |
| 80 | ND | >100 | >100 |
| 144 | ND | 20 | 0.1 |

PDE4 Activity

PDE4 inhibition was measured by following a literature assay procedure (Cortizo J et al., Br J Pharmacol., 1993, 108: 562-568. The assay method involves the following conditions.

Source: Human U937 cells
Substrate: 1.01 µM [$^3$H] camp+camp
Vehicle: 1% DMSO
Pre-Incubation Time/Temperature: 15 minutes at 25° C.
Incubation Time/Temperature. 20 minutes at 25° C.
Incubation buffer: 50 mM Tris-HCl, pH 7.5, 5 mM $MgCl_2$
Quantitation method: Quantitation of [$^3$H] Adenosine
Significance criteria: ≥50% of max stimulation or inhibition
The results are tabulated as shown in the tables XIVa and XIVb.

TABLE XIVa

| Ex. | PDE4 inhibition at 10 µM (%) |
|---|---|
| 59 | 93 |
| 77 | 94 |
| 80 | 87 |
| 98* | 76.1 |
| 109 | 90 |
| 100 | 92 |
| 167 | 82 |
| 173 | 87 |
| 175 | 88 |
| 179 | 84 |

*In this case assay is done with pure PDE4B enzyme (Calbiochem)

TABLE XIVb

| Ex | PDE4 inhibition IC50 (nm) |
|---|---|
| 98 | 7 |

The Tables XVa and XVb contain the disclosed compounds that show the common inhibitory effects on PDE4 inhibitors, TNF-α, IL-12, and IL-6 etc.,

TABLE XVa

| Ex | TNF-α IC$_{50}$ nm | TNF-α in vivo (mice) | COX1 at 10 μm | COX2 at 10 μm | IL-1β at 10 μm | IL-6 at 10 μm | IL-12 at 10 μm |
|---|---|---|---|---|---|---|---|
| 80 | 78 | 87 | NA | 20 | 36 | NA | ND |
| 59 | 64 | 82 | 32 | 31 | 29 | 37 | ND |

TABLE XVb

| Ex | PDE4 at 10 μm | Arthritis | IBD DAI | Psoriasis Ear thickness | Cancer cell lines DU, HCT, NCI (Mean GI50, μm) |
|---|---|---|---|---|---|
| 80 | 93 | ND | 35 | 19 | >100 (for HCT and NCI) |
| 59 | 87 | ND | ND | ND | >100 (for HCT); 10.5 (for NCI) |

We claim:

1. A compound having the formula:

[chemical structure: 3-sulfamoylphenyl group attached to pyrimidine bearing morpholine, phenyl, and CF$_3$ substituents]

or its tautomeric forms, polymorphs, solvates, or pharmaceutically acceptable salts thereof.

2. A compound having the formula:

[chemical structure similar to claim 1]

as claimed in claim 1.

3. A composition comprising a compound having the formula:

[chemical structure similar to claim 1]

or its tautomeric forms, polymorphs, solvates, or pharmaceutically acceptable salts thereof, and a pharmaceutically acceptable carrier, diluent, excipient or solvate.

4. The composition of claim 3 in the form of a tablet, capsule, powder, syrup, solution or suspension.

5. A method of treatment of rheumatoid arthritis in a mammal comprising administering an effective amount of a compound as claimed in claim 1 to the mammal in need thereof.

6. A method of treatment of osteoporosis in a mammal comprising administering an effective amount of a compound as claimed in claim 1 to the mammal in need thereof.

7. A method of treatment of multiple myeloma in a mammal comprising administering an effective amount of a compound as claimed in claim 1 to the mammal in need thereof.

8. A method of treatment of uveitis in a mammal comprising administering an effective amount of a compound as claimed in claim 1 to the mammal in need thereof.

9. A method of treatment of atherosclerosis in a mammal comprising administering an effective amount of a compound as claimed in claim 1 to the mammal in need thereof.

10. A method of treatment of osteoarthritis in a mammal comprising administering an effective amount of a compound as claimed in claim 1 to the mammal in need thereof.

11. A method of treatment of rheumatoid spondylitis in a mammal comprising administering an effective amount of a compound as claimed in claim 1 to the mammal in need thereof.

12. A method of treatment of inflammatory bowel disease in a mammal comprising administering an effective amount of a compound as claimed in claim 1 to the mammal in need thereof.

13. A method of treatment of psoriasis in a mammal comprising administering an effective amount of a compound as claimed in claim 1 to the mammal in need thereof.

14. A method of treatment of adult respiratory distress syndrome (ARDS) in a mammal comprising administering an effective amount of a compound as claimed in claim 1 to the mammal in need thereof.

15. A method of treatment of multiple sclerosis in a mammal comprising administering an effective amount of a compound as claimed in claim 1 to the mammal in need thereof.

16. A method of treatment of allergic rhinitis in a mammal comprising administering an effective amount of a compound as claimed in claim 1 to the mammal in need thereof.

17. A method of treatment of contact dermatitis in a mammal comprising administering an effective amount of a compound as claimed in claim 1 to the mammal in need thereof.

18. A method of treatment of asthma in a mammal comprising administering an effective amount of a compound as claimed in claim 1 to the mammal in need thereof.

19. A method of treatment of Crohn's disease in a mammal comprising administering an effective amount of a compound as claimed in claim 1 to the mammal in need thereof.

* * * * *